(12) United States Patent
Klun et al.

(10) Patent No.: US 11,104,758 B2
(45) Date of Patent: *Aug. 31, 2021

(54) ORTHODONTIC ARTICLES PREPARED USING A POLYCARBONATE DIOL, AND METHODS OF MAKING SAME

(71) Applicant: 3M INNOVATIVE PROPERTIES COMPANY, St. Paul, MN (US)

(72) Inventors: Thomas P. Klun, Lakeland, MN (US); Zeba Parkar, Marietta, GA (US); John M. Riedesel, San Jose, CA (US); Richard J. Pokorny, Maplewood, MN (US); Chad M. Amb, Roberts, WI (US); Benjamin R. Coonce, South St. Paul, MN (US); Robert S. Clough, St. Paul, MN (US); Tianyu Wu, St. Paul, MN (US); Saswata Chakraborty, Cottage Grove, MN (US); Yongshang Lu, Woodbury, MN (US); Benjamin C. MacMurray, St. Paul, MN (US); Ian Dailey, Maplewood, MN (US); David B. Olson, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/042,384

(22) PCT Filed: May 21, 2019

(86) PCT No.: PCT/US2019/033252
§ 371 (c)(1),
(2) Date: Sep. 28, 2020

(87) PCT Pub. No.: WO2020/005413
PCT Pub. Date: Jan. 2, 2020

(65) Prior Publication Data
US 2021/0163664 A1  Jun. 3, 2021

Related U.S. Application Data

(60) Provisional application No. 62/692,456, filed on Jun. 29, 2018, provisional application No. 62/736,031, (Continued)

(51) Int. Cl.
*C08G 18/44* (2006.01)
*A61C 7/08* (2006.01)
(Continued)

(52) U.S. Cl.
CPC .............. *C08G 18/44* (2013.01); *A61C 7/002* (2013.01); *A61C 7/08* (2013.01); *A61C 13/0019* (2013.01);
(Continued)

(58) Field of Classification Search
None
See application file for complete search history.

(56) References Cited

U.S. PATENT DOCUMENTS

| 3,429,722 A | 2/1969 | Economy |
| 3,795,524 A | 3/1974 | Sowman |

(Continued)

FOREIGN PATENT DOCUMENTS

| CN | 103374260 | 10/2013 |
| CN | 104380150 | 2/2015 |

(Continued)

OTHER PUBLICATIONS

Fang, The influence of monobutyl itaconate and β-carboxyethyl acrylate on acrylic latex pressure sensitive adhesives, International Journal of Adhesion and Adhesives, Aug. 2018, vol. 84, pp. 387-393.

(Continued)

*Primary Examiner* — Tae H Yoon
(74) *Attorney, Agent, or Firm* — Adrian L. Pishko

(57) ABSTRACT

The present disclosure provides an orthodontic article including the reaction product of the photopolymerizable composition. The photopolymerizable composition includes i) a monofunctional (meth)acrylate monomer whose cured homopolymer has a glass transition temperature of 90 degrees Celsius or greater; ii) a photoinitiator; and iii) a polymerization reaction product of components. The components include 1) an isocyanate; 2) a (meth)acrylate mono-ol; 3) a polycarbonate diol; and 4) a catalyst. Further, the present disclosure provides a method of making an orthodontic article. The method includes obtaining a photopolymerizable composition and selectively curing the photopolymerizable composition to form an orthodontic article. Further, methods are provided, including receiving, by a manufacturing device having one or more processors, a digital object comprising data specifying an orthodontic article; and generating, with the manufacturing device by an additive manufacturing process, the orthodontic article based on the digital object. A system is also provided, including a display that displays a 3D model of an orthodontic article; and one or more processors that, in response to the 3D model selected by a user, cause a 3D printer to create a physical object of an orthodontic article.

39 Claims, 7 Drawing Sheets

Related U.S. Application Data filed on Sep. 25, 2018, provisional application No. 62/769,421, filed on Nov. 19, 2018.

(51) Int. Cl.

| | | |
|---|---|---|
| *A61C 13/00* | (2006.01) | |
| *A61C 7/00* | (2006.01) | |
| *B33Y 10/00* | (2015.01) | |
| *B33Y 70/00* | (2020.01) | |
| *B33Y 80/00* | (2015.01) | |
| *B33Y 40/20* | (2020.01) | |
| *B29C 71/00* | (2006.01) | |
| *B29C 71/02* | (2006.01) | |
| *B29C 71/04* | (2006.01) | |
| *C08G 18/22* | (2006.01) | |
| *C08G 18/24* | (2006.01) | |
| *C08G 18/32* | (2006.01) | |
| *C08G 18/67* | (2006.01) | |
| *C08G 64/30* | (2006.01) | |
| *C08K 5/3437* | (2006.01) | |
| *B33Y 30/00* | (2015.01) | |

(52) U.S. Cl.
CPC .......... *B29C 71/0009* (2013.01); *B29C 71/02* (2013.01); *B29C 71/04* (2013.01); *B33Y 10/00* (2014.12); *B33Y 40/20* (2020.01); *B33Y 70/00* (2014.12); *B33Y 80/00* (2014.12); *C08G 18/222* (2013.01); *C08G 18/227* (2013.01); *C08G 18/246* (2013.01); *C08G 18/3206* (2013.01); *C08G 18/672* (2013.01); *C08G 64/305* (2013.01); *C08K 5/3437* (2013.01); *B29C 2071/0027* (2013.01); *B33Y 30/00* (2014.12); *C08G 2650/16* (2013.01)

(56) References Cited

U.S. PATENT DOCUMENTS

| | | | |
|---|---|---|---|
| 4,047,965 | A | 9/1977 | Karst |
| 4,255,243 | A | 3/1981 | Coqueugniot |
| 4,264,752 | A | 4/1981 | Watson, Jr. |
| 4,591,626 | A | 5/1986 | Kawai |
| 4,954,462 | A | 9/1990 | Wood |
| 5,185,299 | A | 2/1993 | Wood |
| 5,476,749 | A | 12/1995 | Steinmann |
| 5,780,154 | A | 7/1998 | Okano |
| 5,849,270 | A | 12/1998 | Podszun |
| 5,981,621 | A | 11/1999 | Clark |
| 6,183,593 | B1 | 2/2001 | Narang |
| 6,200,732 | B1 | 3/2001 | Tamura |
| 6,376,571 | B1 | 4/2002 | Chawla |
| 6,379,866 | B2 | 4/2002 | Lawton |
| 8,044,235 | B2 | 10/2011 | Nozawa |
| 9,205,601 | B2 | 12/2015 | DeSimone |
| 9,360,757 | B2 | 6/2016 | DeSimone |
| 9,695,338 | B2 | 7/2017 | Egashira |
| 10,316,130 | B2 * | 6/2019 | Kusano .................. C09J 175/06 |
| 2007/0031791 | A1 | 2/2007 | Cinader, Jr. |
| 2008/0248442 | A1 | 10/2008 | Raby |
| 2011/0091832 | A1 | 4/2011 | Kim |
| 2012/0046376 | A1 | 2/2012 | Loccufier |
| 2013/0095446 | A1 | 4/2013 | Andreiko |
| 2014/0356799 | A1 | 12/2014 | Cinader, Jr. |
| 2015/0044623 | A1 | 2/2015 | Rundlett |
| 2015/0072083 | A1 | 3/2015 | Nebioglu |
| 2016/0167301 | A1 | 6/2016 | Cole |
| 2016/0184189 | A1 | 6/2016 | Hagiwara |
| 2016/0332367 | A1 * | 11/2016 | Sun ........................ C08L 33/08 |
| 2017/0007362 | A1 | 1/2017 | Chen |
| 2017/0158803 | A1 | 6/2017 | Amin |

FOREIGN PATENT DOCUMENTS

| | | |
|---|---|---|
| CN | 104684953 | 6/2015 |
| CN | 104765251 | 7/2015 |
| GB | 2 163 443 | 2/1986 |
| JP | 61-021117 | 1/1986 |
| JP | H08-188630 | 7/1996 |
| JP | H09-216924 | 8/1997 |
| JP | 3115792 | 12/2000 |
| JP | 3301447 | 7/2002 |
| JP | 2004-217809 | 8/2004 |
| JP | 2009-203362 | 9/2009 |
| JP | 2010-037411 A * | 2/2010 |
| JP | 2010-043194 | 2/2010 |
| JP | 4526056 | 6/2010 |
| JP | 4682544 | 2/2011 |
| JP | 4880248 | 12/2011 |
| JP | 5055764 | 8/2012 |
| JP | 5068513 | 8/2012 |
| JP | 2012-184385 | 9/2012 |
| JP | 5224965 | 3/2013 |
| JP | 5445215 | 1/2014 |
| JP | 2014-114444 | 6/2014 |
| JP | 2014-116295 | 6/2014 |
| JP | 2016-112824 | 6/2016 |
| JP | 2017-048288 | 3/2017 |
| JP | 2017-210579 | 11/2017 |
| JP | 2017-537687 | 12/2017 |
| KR | 20000065218 | 11/2000 |
| WO | WO 1991-003503 | 3/1991 |
| WO | 1996-15179 | 5/1996 |
| WO | WO 1998-021157 | 5/1998 |
| WO | WO 2007-129704 | 11/2007 |
| WO | WO 2009-045752 | 4/2009 |
| WO | WO 2012-045660 | 4/2012 |
| WO | WO 2014-077688 | 5/2014 |
| WO | WO 2015-094842 | 6/2015 |
| WO | 2016-075528 | 5/2016 |
| WO | WO 2016-109660 | 7/2016 |
| WO | WO 2016-148960 | 9/2016 |
| WO | WO 2016-149007 | 9/2016 |
| WO | WO 2016-182444 | 11/2016 |
| WO | WO 2017-208959 | 12/2017 |
| WO | WO 2018-005501 | 1/2018 |
| WO | WO 2018-119026 | 6/2018 |
| WO | WO 2019-023009 | 1/2019 |
| WO | WO 2019-103855 | 5/2019 |
| WO | WO 2019-104072 | 5/2019 |
| WO | WO 2019-104079 | 5/2019 |
| WO | WO 2019-175716 | 9/2019 |
| WO | WO 2020-005411 | 1/2020 |
| WO | WO 2020-104873 | 5/2020 |
| WO | WO 2020-157598 | 8/2020 |

OTHER PUBLICATIONS

Fleischhaker, "Glass-Transition-, Melting-, and Decomposition Temperatures of Tailored Polyacrylates and Polymethacrylates: General Trends and Structure-Property Relationships" Macromolecular Chemistry and Physics, Jun. 2014, vol. 215, No. 12, pp. 1192-1200.

Hopfinger, "Molecular Modeling of Polymers. IV. Estimation of Glass Transition Temperatures", Journal of Polymer Science: Part B: Polymer Physics, Sep. 1988, vol. 26, No. 10, pp. 2007-2028.

Jakubowski, "Comparison of thermomechanical properties of statistical, gradient and block copolymers of isobornyl acrylate and n-butyl acrylate with various acrylate homopolymers", Polymer, Mar. 2008, vol. 49, No. 06, pp. 1567-1578.

Matsumoto, "Radical Polymerization of 4-tert-Butylcyclohexyl Methacrylate: Polymerization Kinetics and Polymer Properties", Macromolecules, Mar. 1993, vol. 26 No. 7, pp. 1659-1665.

Matsumoto, "Synthesis and Characterization of Poly(1-adamantyl methacrylate): Effects of the Adamantyl Group on Radical Polymerization Kinetics and Thermal Properties of the Polymer", Macromolecules, Jul. 1991, vol. 24, No. 14, pp. 4017-4024.

Matsumoto, "Synthesis and Thermal Properties of Poly (cycloalkyl methacrylate) s Bearing Bridged- and Fused-Ring Structures",

(56) References Cited

OTHER PUBLICATIONS

Journal of Polymer Science: Part A Polymer Chemistry, Sep. 1993, vol. 31, No. 10, pp. 2531-2539.
"Methacrylate Resins", By E. I. du Pont de Nemours & Company, Inc., at the Ninety-second Meeting of the American Chemical Society at Pittsburgh, Pa., Industrial and Engineering Chemistry, Sep. 1936, vol. 28, No. 10, pp. 1160-1163.
Russell, "Thermal and Dynamic Mechanical Relaxation Behavior of Stereoregular Poly(2-Hydroxyethyl Methacrylate)", Journal of Polymer Science: Polymer Physics Edition, Jun. 1980, vol. 18, No. 06, pp. 1271-1283.
Song, "In Vitro Evaluation of Chemically Cross-Linked Shape-Memory Acrylate-Methacrylate Copolymer Networks as Ocular Implants", The Journal of Physical Chemistry B, Jun. 2010, vol. 114, No. 21, pp. 7172-7178.
Turner, "The glass transition temperature of poly(N-vinyl pyrrolidone) by differential scanning calorimetry", Polymer, May 1985, vol. 26, No. 5, pp. 757-762.
Wilson, "Thermal Expansion of Amorphous Polymers at Atmospheric Pressure. I. Experimental", Macromolecules, Nov. 1973, vol. 6, No. 6, pp. 902-908.
International Search Report for PCT International Application No. PCT/US2019/033241, dated Aug. 7, 2019, 5 pages.
International Search Report for PCT International Application No. PCT/US2019/033252, dated Aug. 20, 2019, 2 pages.

\* cited by examiner

ORTHODONTIC ARTICLES PREPARED USING A POLYCARBONATE DIOL, AND METHODS OF MAKING SAME

CROSS REFERENCE TO RELATED APPLICATIONS

This application is a national stage filing under 35 U.S.C. 371 of PCT/US2019/033252, filed May 21, 2019, which claims the benefit of U.S. Application No. 62/692,456, filed Jun. 29, 2018, U.S. Application No. 62/736,031, filed Sep. 25, 2018 and U.S. Application No. 62/769,421, filed Nov. 19, 2018, the disclosures of which are incorporated by reference in their entirety herein.

TECHNICAL FIELD

The present disclosure broadly relates to orthodontic articles and methods of making the orthodontic articles, such as additive manufacturing methods.

BACKGROUND

The use of stereolithography and inkjet printing to produce three-dimensional articles has been known for a relatively long time, and these processes are generally known as methods of so called 3D printing (or additive manufacturing). In vat polymerization techniques (of which stereolithography is one type), the desired 3D article is built up from a liquid, curable composition with the aid of a recurring, alternating sequence of two steps: in the first step, a layer of the liquid, curable composition, one boundary of which is the surface of the composition, is cured with the aid of appropriate radiation within a surface region which corresponds to the desired cross-sectional area of the shaped article to be formed, at the height of this layer, and in the second step, the cured layer is covered with a new layer of the liquid, curable composition, and the sequence of steps is repeated until a so-called green body (i.e., gelled article) of the desired shape is finished. This green body is often not yet fully cured and must, usually, be subjected to post-curing. The mechanical strength of the green body immediately after curing, otherwise known as green strength, is relevant to further processing of the printed articles.

Other 3D printing techniques use inks that are jetted through a print head as a liquid to form various three-dimensional articles. In operation, the print head may deposit curable photopolymers in a layer-by-layer fashion. Some jet printers deposit a polymer in conjunction with a support material or a bonding agent. In some instances, the build material is solid at ambient temperatures and converts to liquid at elevated jetting temperatures. In other instances, the build material is liquid at ambient temperatures.

SUMMARY

Existing printable/polymerizable resins tend to be too brittle (e.g., low elongation, short-chain crosslinked bonds, thermoset composition, and/or high glass transition temperature) for a resilient oral appliance such as an aligner. An aligner or other appliance prepared from such resins could easily break in the patient's mouth during treatment, creating material fragments that may abrade or puncture exposed tissue or be swallowed. These fractures at the very least interrupt treatment and could have serious health consequences for the patient. Thus, there is a need for curable liquid resin compositions that are tailored and well suited for creation of resilient articles using 3D printing (e.g., additive manufacturing) method. Preferably, curable liquid resin compositions to be used in the vat polymerization 3D printing process have low viscosity, a proper curing rate, and excellent mechanical properties in the final cured article. In contrast, compositions for inkjet printing processes need to be much lower viscosity to be able to be jetted through nozzles, which is not the case for most vat polymerization resins.

In a first aspect, an orthodontic article is provided. The orthodontic article includes a) a polymerized reaction product of a photopolymerizable composition. The photopolymerizable composition includes i) a monofunctional (meth)acrylate monomer whose cured homopolymer has a $T_g$ of 90° C. or greater; ii) a photoinitiator; and iii) a polymerization reaction product of components. The components of iii) include 1) an isocyanate; 2) a (meth)acrylate mono-ol; a polycarbonate diol of Formula (I): $H(O-R_1-O-C(=O))_m-O-R_2-OH$ (I); and 3) a catalyst. Each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is (an integer of) 2 to 23. The polymerized reaction product of the photopolymerizable composition has a shape of the orthodontic article.

In a second aspect, a method of making an orthodontic article is provided. The method includes a) obtaining a photopolymerizable composition according to the first aspect; b) selectively curing the photopolymerizable composition; and c) repeating steps a) and b) to form multiple layers and create the orthodontic article.

In a third aspect, a non-transitory machine readable medium is provided. The non-transitory machine readable medium includes data representing a three-dimensional model of an orthodontic article, when accessed by one or more processors interfacing with a 3D printer, causes the 3D printer to create an orthodontic article comprising a reaction product of a photopolymerizable composition according to the first aspect.

In a fourth aspect, a method is provided. The method includes a) retrieving, from a non-transitory machine readable medium, data representing a 3D model of an article; b) executing, by one or more processors, a 3D printing application interfacing with a manufacturing device using the data; and c) generating, by the manufacturing device, a physical object of the orthodontic article. The orthodontic article includes a reaction product of a photopolymerizable composition according to the first aspect.

In a fifth aspect, another method is provided. The method includes a) receiving, by a manufacturing device having one or more processors, a digital object comprising data specifying a plurality of layers of an orthodontic article; and b) generating, with the manufacturing device by an additive manufacturing process, the orthodontic article based on the digital object. The orthodontic article includes a reaction product of a photopolymerizable composition according to the first aspect.

In a sixth aspect, a system is provided. The system includes a) a display that displays a 3D model of an orthodontic article; and b) one or more processors that, in response to the 3D model selected by a user, cause a 3D printer to create a physical object of an orthodontic article. The orthodontic article includes a reaction product of a photopolymerizable composition.

In a seventh aspect, a compound is provided. The compound is of Formula (V):

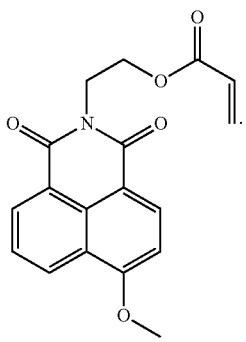

(V)

The compound of the seventh aspect can advantageously be used as a UV absorber in orthodontic articles and methods according to the first through fifth aspects.

Clear tray aligners and tensile bars made according to at least certain embodiments of this disclosure were found to show low brittleness, good resistance to water, and good toughness.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
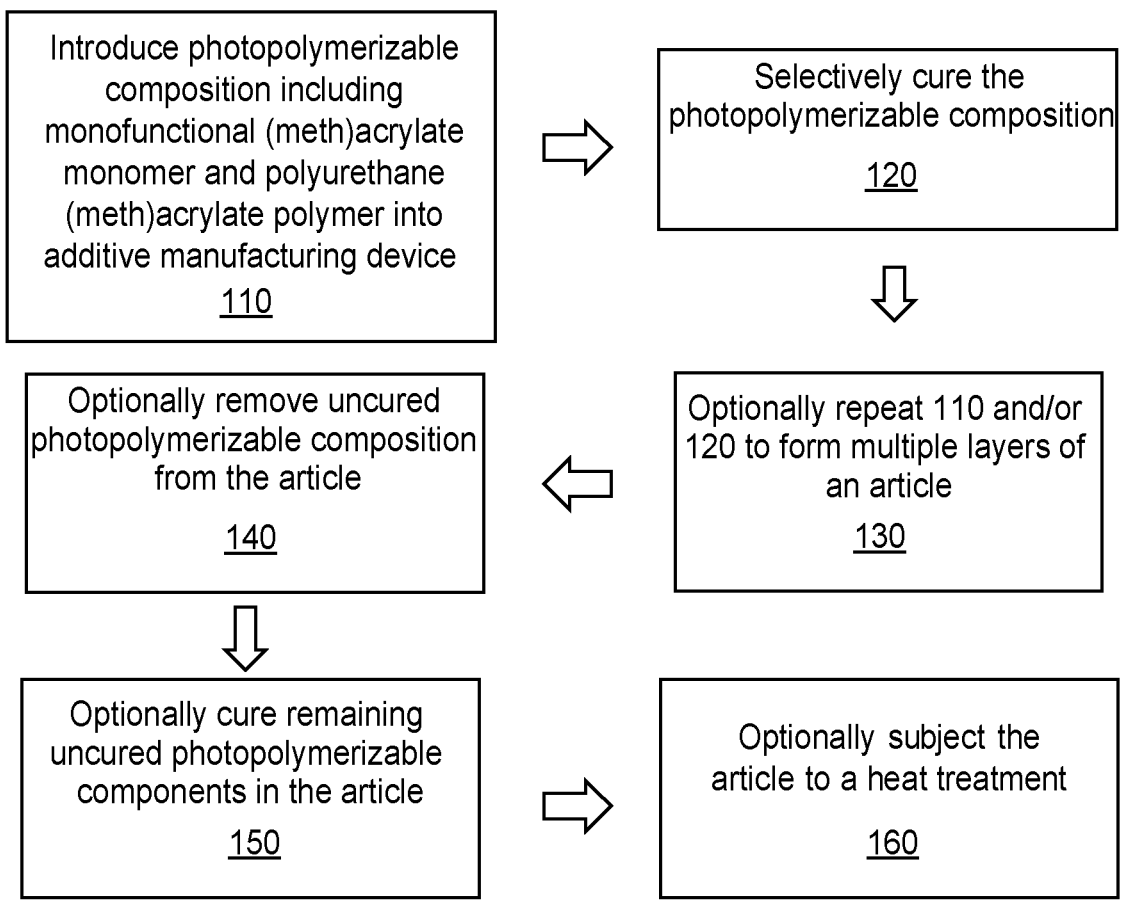
FIG. 1 is a flowchart of a process for building an article using the photopolymerizable compositions disclosed herein.

While the above-identified figures set forth several embodiments of the disclosure other embodiments are also contemplated, as noted in the description. The figures are not necessarily drawn to scale. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

As used herein, "aliphatic group" means a saturated or unsaturated linear, branched, or cyclic hydrocarbon group. This term is used to encompass alkyl, alkenyl, and alkynyl groups, for example.

As used herein, "alkyl" means a linear or branched, cyclic or acyclic, saturated monovalent hydrocarbon having from one to thirty-two carbon atoms, e.g., methyl, ethyl, 1-propyl, 2-propyl, pentyl, and the like.

As used herein, "alkylene" means a linear saturated divalent hydrocarbon having from one to twelve carbon atoms or a branched saturated divalent hydrocarbon radical having from three to twelve carbon atoms, e.g., methylene, ethylene, propylene, 2-methylpropylene, pentylene, hexylene, and the like.

As used herein, "alkenyl" refers to a monovalent linear or branched unsaturated aliphatic group with one or more carbon-carbon double bonds, e.g., vinyl. Unless otherwise indicated, the alkenyl groups typically contain from one to twenty carbon atoms.

As used herein, the term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

As used herein, "aralkylene" refers to a divalent group that is an alkylene group substituted with an aryl group or an alkylene group attached to an arylene group. The term "alkarylene" refers to a divalent group that is an arylene group substituted with an alkyl group or an arylene group attached to an alkylene group. Unless otherwise indicated, for both groups, the alkyl or alkylene portion typically has from 1 to 20 carbon atoms, 1 to 10 carbon atoms, 1 to 6 carbon atoms, or 1 to 4 carbon atoms. Unless otherwise indicated, for both groups, the aryl or arylene portion typically has from 6 to 20 carbon atoms, 6 to 18 carbon atoms, 6 to 16 carbon atoms, 6 to 12 carbon atoms, or 6 to 10 carbon atoms.

As used herein, the term "essentially free" in the context of a composition being essentially free of a component, refers to a composition containing less than 1% by weight (wt. %), 0.5 wt. % or less, 0.25 wt. % or less, 0.1 wt. % or less, 0.05 wt. % or less, 0.001 wt. % or less, or 0.0001 wt. % or less of the component, based on the total weight of the composition.

As used herein, the term "glass transition temperature" ($T_g$), of a polymer refers to the transition of a polymer from a glassy state to a rubbery state and can be measured using Differential Scanning calorimetry (DSC), such as at a heating rate of 10° C. per minute in a nitrogen stream. When the $T_g$ of a monomer is mentioned, it is the $T_g$ of a homopolymer of that monomer. The homopolymer must be sufficiently high molecular weight such that the $T_g$ reaches a limiting value, as it is generally appreciated that a $T_g$ of a homopolymer will increase with increasing molecular weight to a limiting value. The homopolymer is also understood to be substantially free of moisture, residual monomer, solvents, and other contaminants that may affect the $T_g$. A suitable DSC method and mode of analysis is as described in Matsumoto, A. et. al., J. Polym. Sci. A., Polym. Chem. 1993, 31, 2531-2539.

As used herein, the terms "hardenable" refers to a material that can be cured or solidified, e.g., by heating to remove solvent, heating to cause polymerization, chemical crosslinking, radiation-induced polymerization or crosslinking, or the like.

As used herein, "curing" means the hardening or partial hardening of a composition by any mechanism, e.g., by heat, light, radiation, e-beam, microwave, chemical reaction, or combinations thereof.

As used herein, "cured" refers to a material or composition that has been hardened or partially hardened (e.g., polymerized or crosslinked) by curing.

As used herein, "integral" refers to being made at the same time or being incapable of being separated without damaging one or more of the (integral) parts.

As used herein, the term "(meth)acrylate" is a shorthand reference to acrylate, methacrylate, or combinations thereof, "(meth)acrylic" is a shorthand reference to acrylic, methacrylic, or combinations thereof, and "(meth)acryl" is a shorthand reference to acryl and methacryl groups. "Acryl" refers to derivatives of acrylic acid, such as acrylates, methacrylates, acrylamides, and methacrylamides. By "(meth)acryl" is meant a monomer or oligomer having at least one acryl or methacryl groups, and linked by an aliphatic segment if containing two or more groups. As used herein, "(meth)acrylate-functional compounds" are compounds that include, among other things, a (meth)acrylate moiety.

As used herein, "polymerizable composition" means a hardenable composition that can undergo polymerization upon initiation (e.g., free-radical polymerization initiation). Typically, prior to polymerization (e.g., hardening), the polymerizable composition has a viscosity profile consistent with the requirements and parameters of one or more 3D printing systems. In some embodiments, for instance, hardening comprises irradiating with actinic radiation having sufficient energy to initiate a polymerization or cross-linking reaction. For instance, in some embodiments, ultraviolet (UV) radiation, e-beam radiation, or both, can be used. When actinic radiation can be used, the polymerizable composition is referred to as a "photopolymerizable composition".

As used herein, a "resin" contains all polymerizable components (monomers, oligomers and/or polymers) being present in a hardenable composition. The resin may contain only one polymerizable component compound or a mixture of different polymerizable compounds.

As used herein, the "residue of a diisocyanate", is the structure of the diisocyanate after the —NCO groups are removed. For example, 1,6-hexamethylene diisocyanate has the structure OCN—$(CH_2)_6$—NCO, and its residue, $R_{di}$, after removal of the isocyanate groups is —$(CH_2)_6$—.

As used herein, the "residue of a polycarbonate polyol", is the structure of the polycarbonate polyol after the —OH groups are removed. For example, a polycarbonate diol having the structure H(O—$R_1$—O—C(=O))$_m$—O—$R_2$—OH, has a residue, $R_{dOH}$, after removal of the end —OH groups, of —$R_1$—O—C(=O)—(O—$R_1$—O—C(=O))$_{m-1}$—O—$R_2$—, wherein each $R_1$ in each repeat unit and $R_2$ is independently an aliphatic, cycloaliphatic, or aliphatic/cycloaliphatic alkylene group and m is 2 to 23. Examples of $R_1$ and $R_2$ groups include —$CH_2$—$CH_2$—CH($CH_3$)—$CH_2$—$CH_2$—, —$CH_2$—C($CH_3$)$_2$—$CH_2$—, —$(CH_2)_6$—, —$(CH_2)_9$—, and —$(CH_2)_{10}$—.

As used herein, "thermoplastic" refers to a polymer that flows when heated sufficiently above its glass transition point and become solid when cooled.

As used herein, "thermoset" refers to a polymer that permanently sets upon curing and does not flow upon subsequent heating. Thermoset polymers are typically cross-linked polymers.

As used herein, "occlusal" means in a direction toward the outer tips of the patient's teeth; "facial" means in a direction toward the patient's lips or cheeks; and "lingual" means in a direction toward the patient's tongue.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a", "an", and "the" are not intended to refer to only a singular entity, but include the general class of which a specific example may be used for illustration. The terms "a", "an", and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

In a first aspect, the present disclosure provides an orthodontic article. The orthodontic article includes:

a) a polymerized reaction product of a photopolymerizable composition comprising:

i) a monofunctional (meth)acrylate monomer whose cured homopolymer has a $T_g$ of 90° C. or greater;

ii) a photoinitiator; and iii) a polymerization reaction product of components, the components comprising:
  1) an isocyanate;
  2) a (meth)acrylate mono-ol;
  3) a polycarbonate diol of Formula (I):

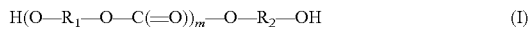
$$H(O-R_1-O-C(=O))_m-O-R_2-OH \qquad (I)$$

wherein each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23; and
  4) a catalyst;
wherein the polymerized reaction product has a shape of the orthodontic article.

The components (i) through (iii) (and 1) through 4)) are discussed in detail below.

Monofunctional (Meth)Acrylate Monomer

In any embodiment, the photopolymerizable composition comprises a monofunctional (meth)acrylate monomer having a high glass transition temperature ($T_g$), i.e., whose cured homopolymer has a $T_g$ of 90° C. or greater. In some embodiments, a monofunctional (meth)acrylate monomer is present whose cured homopolymer has a $T_g$ of 100° C. or greater, 110° C. or greater, 120° C. or greater, 125° C. or greater, 130° C. or greater, 135° C. or greater, 140° C. or greater, 145° C. or greater, 150° C. or greater, 155° C. or greater, 160° C. or greater, 165° C. or greater, 170° C. or greater, 175° C. or greater, 180° C. or greater, 185° C. or greater, 190° C. or greater, or even 195° C. or greater. In select embodiments, a monofunctional (meth)acrylate monomer is present whose cured homopolymer has a $T_g$ of 150° C. or greater, 170° C. or greater, or 180° C. or greater. The $T_g$ of the homopolymer of the monofunctional (meth) acrylate monomer is typically no greater than about 260° C. For example, 1-adamantyl methacrylate decomposes at about 260° C. In some embodiments, the $T_g$ of the homopolymer of the monofunctional (meth)acrylate monomer is no greater than 255° C., 250° C., 245° C., 240° C., 235° C., 230° C., 225° C., 220° C., 215° C., 210° C., 205° C. or 200° C. The inclusion of one or more monofunctional (meth) acrylate monomers whose cured homopolymer has a $T_g$ of 90° C. or greater in a photopolymerizable composition contributes to increasing the relaxation modulus of a photopolymerization reaction product of the composition as measured after soaking in deionized water. Often, the $T_g$ of a homopolymer of a monomer can be found in the literature, such as in Table 1 below. Table 1 includes the reported $T_g$ of the homopolymer of a number of monofunctional (meth) acrylate monomers and the literature source of the reported $T_g$.

In some embodiments, the monofunctional (meth)acrylate monomer comprises a cycloaliphatic monofunctional (meth) acrylate. Suitable monofunctional (meth)acrylate monomers include for instance and without limitation, dicyclopentadienyl acrylate, dicyclopentanyl acrylate, dimethyl-1-adamantyl acrylate, cyclohexyl methacrylate, butyl methacrylate (e.g., tert-butyl methacrylate), 3,3,5-trimethylcyclohexyl methacrylate, butyl-cyclohexylmethacrylate (e.g., cis-4-tert-butyl-cyclohexylmethacrylate, 73/27 trans/cis-4-tert-butyl-cyclohexylmethacrylate, or trans-4-tert-butylcyclohexyl methacrylate), 2-decahydronapthyl methacrylate, 1-adamantyl acrylate, dicyclopentadienyl methacrylate, dicyclopentanyl methacrylate, isobornyl methacrylate (e.g., d,l-isobornyl methacrylate), dimethyl-1-adamantyl methacrylate, bornyl methacrylate (e.g., d,l-bornyl methacrylate), 3-tetracyclo[4.4.0.1.1]dodecyl methacrylate, 1-adamantyl methacrylate, isobornyl acrylate, or combinations thereof. In an embodiment, the monofunctional (meth) acrylate monomer comprises isobornyl methacrylate.

In certain embodiments, the weight ratio of the monofunctional (meth)acrylate monomer to the polyurethane (meth)acrylate polymer is 60:40 to 40:60, 55:45 to 45:55, or 50:50. Often, the monofunctional (meth)acrylate monomer is present in an amount of 40 parts or more by weight per 100 parts of the total photopolymerizable composition, 45 parts or more, 46 parts or more, 47 parts or more, 48 parts or more, 49 parts or more, or 50 parts or more; and 65 parts or less, 64 parts or less, 63 parts or less, 62 parts or less, 61 parts or less, 60 parts or less, 59 parts or less, 58 parts or less, 57 parts or less, 56 parts or less, or 55 parts or less, by weight per 100 parts of the total photopolymerizable composition.

In some embodiments of the invention, the cured material will be in contact with an aqueous environment. In those cases, it is advantageous to utilize materials which have low affinity for water. The affinity for water of certain (meth) acrylate monomers can be estimated by the calculation of a partition coefficient (P) between water and an immiscible solvent, such as octanol. This can serve as a quantitative descriptor of hydrophilicity or lipophilicity. The octanol/ water partition coefficient can be calculated by software programs such as ACD ChemSketch, (Advanced Chemistry Development, Inc., Toronto, Canada) using the log of octanol/water partition coefficient (log P) module. In embodiments of the present invention, the calculated log P value is greater than 1, 1.5, 2, 2.5, 3, 3.5, or 4. The calculated log P value is typically no greater than 12.5. In some embodiments, the calculated log P value is no greater than 12, 11.5, 11, 10.5, 10, 9.5, 9, 8.5, 8, 7.5, 7, 6.5, 6, or 5.5. Moreover, in some embodiments, photopolymerizable compositions exclude the presence of a significant amount of hydrophilic (meth)acrylate monomers by being essentially free of any monofunctional (meth)acrylate monomer having a log P value of less than 3, less than 2, or less than 1.

In some embodiments, photopolymerizable compositions contain hydrophilic (meth)acrylate monomers or polymers (e.g., hydrophilic urethane (meth)acrylate polymer) having a log P value of less than 3, less than 2, or less than 1, in an amount of 25% by weight or less, based on the total weight of the photopolymerizable composition, such as 23%, 21%, 20%, 19%, 17%, 15%, 13%, or 11% or less of hydrophilic components; and 1% by weight or more, 2%, 3%, 4%, 5%, 7%, 9%, or 10% or more hydrophilic components, for example 1% to 25% by weight, based on the total weight of the photopolymerizable composition. In some embodiments, the combination of a hydrophilic component and a monofunctional (meth)acrylate monomer whose cured homopolymer has a $T_g$ of 150° C. or greater can impart advantageous properties to an article, for instance, 20% by weight or more, 22%, 25%, 27%, 30%, 32%, 35%, 37%, 40%, 42%, 45%, 47%, or 50% by weight or more of a monofunctional (meth)acrylate monomer whose cured homopolymer has a $T_g$ of 150° C. may be included when 1% to 25% by weight of a hydrophilic component is present, each based on the total weight of the photopolymerizable composition.

TABLE 1

Reported glass transition temperature ($T_g$) and calculated log P (log of octanol/water partition coefficient) of homopolymers of monofunctional (meth)acrylate monomers.

| Monomer | $T_g$ (° C.) | $T_g$ Reference | Calculated log P |
|---|---|---|---|
| 3,3,5-trimethylcyclohexyl acrylate | 15 | Hopfinger et. al.; J. Polym. Sci. B., Polym. Phys. 1988, 26, 2007 | 4.38 |
| d,l-isobornyl acrylate | 94 | Jakubowski et. al. Polymer, 2008, 49, 1567 | 4.22 |
| dicyclopentanyl acrylate | 103 | U.S. Pat. No. 4,591,626 | 3.69 |
| 3,5-dimethyl-1-adamantyl acrylate | 105 | Matsumoto, A. et. al. Macromolecules 1991, 24, 4017 | 4.63 |
| cyclohexyl methacrylate | 107 | Wilson, P. S., Simha, R.; Macromolecules, 1973, 95, 3, 902 | 3.41 |
| tert-butyl methacrylate | 113 | Matsumoto, A. et. al. Macromolecules 1991, 24, 4017 | 2.57 |
| 3,3,5-trimethylcyclohexyl methacrylate | 125 | Hopfinger et. al.; J. Polym. Sci. B., Polym. Phys. 1988, 26, 2007 | 4.93 |
| cis-4-tert-butyl-cyclohexylmethacrylate | 132 | Matsumoto, A. et. al. Macromolecules 1993, 26, 7, 1659 | 5.13 |
| 2-decahydronapthyl methacrylate | 145 | Matsumoto, A. et. al., J. Polym. Sci. A., Polym. Chem. 1993, 31, 2531 | 4.95 |
| 1-adamantyl acrylate | 153 | Matsumoto, A. et. al. Macromolecules 1991, 24, 4017 | 3.68 |
| Mixture of 73% trans-4-tert-butylcyclohexylmethacrylate/27% cis-4-tert-butylcyclohexylmethacrylate | 163 | Matsumoto, A. et. al. Macromolecules 1993, 26, 7, 1659 | 5.13 |
| dicyclopentanyl methacrylate | 173 | U.S. Pat. No. 4,591,626 | 4.24 |
| trans-4-tert-butylcyclohexyl methacrylate | 178 | Matsumoto, A. et. al. Macromolecules 1993, 26, 7, 1659 | 5.13 |
| d,l-isobornyl methacrylate | 191 | Matsumoto, A. et. al., J. Polym. Sci. A., Polym. Chem. 1993, 31, 2531 | 4.77 |
| 3,5-dimethyl-1-adamantyl methacrylate | 194 | Matsumoto, A. et. al. Macromolecules 1991, 24, 4017 | 5.19 |
| d,l-bornyl methacrylate | 194 | Matsumoto, A. et. al., J. Polym. Sci. A., Polym. Chem. 1993, 31, 2531 | 4.77 |
| 3-tetracyclo[4.4.0.1.1]dodecyl methacrylate | 199 | Matsumoto, A. et. al., J. Polym. Sci. A., Polym. Chem. 1993, 31, 2531 | 4.66 |
| 1-adamantyl methacrylate | >253 | Matsumoto, A. et. al. Macromolecules 1991, 24, 4017 | 4.23 |
| 2-ethylhexyl methacrylate | −10 | Fleischhaker et. al., Macromol. Chem. Phys. 2014, 215, 1192. | 4.88 |
| tetrahydrofurfuryl methacrylate | 60 | E. I. du Pont de Nemours & Co., Ind. Eng. Chem., 1936, 28, 1160, | 1.38 |
| 2-phenoxyethyl methacrylate | 47 | Song et. al.; J. Phys. Chem. B 2010, 114, 7172 | 3.26 |
| N-vinyl pyrrolidone | 180 | Turner et. al; Polymer, 1985, 26, 757 | 0.37 |
| carboxyethyl acrylate | <30 | Fang et. al.; Int. J. Adhes. and Adhes. 84 (2018) 387-393 | 0.60 |
| 2-hydroxyethyl methacrylate | 105 | Russell et. al.; J. Polym. Sci. Polym. Phys, 1980, 18, 1271 | 0.50 |
| acryloyl morpholine | 147 | Elles, J.; Chimie Moderne, 1959, 4, 26, 53 | −0.94 |

Photoinitiator

Photopolymerizable compositions of the present disclosure include at least one photoinitiator. Suitable exemplary photoinitiators are those available under the trade designations OMNIRAD from IGM Resins (Waalwijk, The Netherlands) and include 1-hydroxycyclohexyl phenyl ketone (OMNIRAD 184), 2,2-dimethoxy-1,2-diphenylethan-1-one (OMNIRAD 651), bis(2,4,6 trimethylbenzoyl)phenylphosphineoxide (OMNIRAD 819), 1-[4-(2-hydroxyethoxy)phenyl]-2-hydroxy-2-methyl-1-propane-1-one (OMNIRAD 2959), 2-benzyl-2-dimethylamino-1-(4-morpholinophenyl) butanone (OMNIRAD 369), 2-Dimethylamino-2-(4-methyl-benzyl)-1-(4-morpholin-4-yl-phenyl)-butan-1-one (OMNIRAD 379), 2-methyl-1-[4-(methylthio)phenyl]-2-morpholinopropan-1-one (OMNIRAD 907), Oligo[2-hydroxy-2-methyl-1-[4-(1-methylvinyl)phenyl]propanone] ESACURE ONE (Lamberti S.p.A., Gallarate, Italy), 2-hydroxy-2-methyl-1-phenyl propan-1-one (DAROCUR 1173), 2, 4, 6-trimethylbenzoyldiphenylphosphine oxide (OMNIRAD TPO), and 2, 4, 6-trimethylbenzoylphenyl phosphinate (OMNIRAD TPO-L). Additional suitable photoinitiators include for example and without limitation, benzyl dimethyl ketal, 2-methyl-2-hydroxypropiophenone, benzoin methyl ether, benzoin isopropyl ether, anisoin methyl ether, aromatic sulfonyl chlorides, photoactive oximes, and combinations thereof.

In some embodiments, a photoinitiator is present in a photopolymerizable composition in an amount of up to about 5% by weight, based on the total weight of polymerizable components in the photopolymerizable composition. In some cases, a photoinitiator is present in an amount of 0.1 wt. % or more, 0.2 wt. % or more, 0.3 wt. % or more, 0.4 wt. % or more, 0.5 wt. % or more, 0.6 wt. % or more, 0.7 wt. % or more, 0.8 wt. % or more, 0.9 wt. % or more, 1.0 wt. % or more, 1.25 wt. % or more, or 1.5 wt. % or more; and 5 wt. % or less, 4.8 wt. % or less, 4.6 wt. % or less, 4.4 wt. % or less, 4.2 wt. % or less, 4.0 wt. % or less, 3.8 wt. % or less, 3.6 wt. % or less, 3.4 wt. % or less, 3.2 wt. % or less, 3.0 wt. % or less, 2.8 wt. % or less, 2.6 wt. % or less, 2.4 wt. % or less, 2.2 wt. % or less, 2.0 wt. % or less, 1.8 wt. % or less, or 1.6 wt. % or less. Stated another way, the photoinitiator may be present in an amount of about 0.1-5% by weight, 0.2-5% by weight, or 0.5-5% by weight, based on the total weight of the photopolymerizable composition.

Further, a thermal initiator can optionally be present in a photopolymerizable composition described herein. In some embodiments, a thermal initiator is present in a photopolymerizable composition or in an amount of up to about 5% by weight, based on the total weight of polymerizable components in the photopolymerizable composition. In some cases, a thermal initiator is present in an amount of about 0.1-5% by weight, based on the total weight of polymerizable components in the photopolymerizable composition. Suitable thermal initiators include for instance and without limitation, peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2-azo-bis(isobutyronitrile), and t-butyl perbenzoate. Examples of commercially available thermal initiators include initiators available from DuPont Specialty Chemical (Wilmington, Del.) under the VAZO trade designation including VAZO 67 (2,2'-azo-bis(2-methybutyronitrile)) VAZO 64 (2,2'-azo-bis(isobutyronitrile)) and VAZO 52 (2,2'-azo-bis(2,2-dimethyvaleronitrile)), and LUCIDOL 70 from Elf Atochem North America, Philadelphia, Pa.

In certain aspects, the use of more than one initiator assists in increasing the percentage of monomer that gets incorporated into the reaction product of polymerizable components and thus decreasing the percentage of the monomer that remains uncured.

Components

Orthodontic articles according to the present disclosure comprise a polymerized reaction product of components. The components include at least one isocyanate, at least one (meth)acrylate mono-ol, at least one polycarbonate diol, and at least one catalyst. Each of these components is discussed in detail below.

Suitable amounts of each of the isocyanate, (meth)acrylate mono-ol, and polycarbonate diol present in the components are based on molar ratios of each of these components to the others. For instance, a ratio of the isocyanate (e.g., a diisocyanate, which has 2 isocyanate equivalents per mole of isocyanate compound) to the polycarbonate diol typically ranges from 4 molar equivalents of the isocyanate to 1 molar equivalent of the alcohol of the polycarbonate diol, to 4 molar equivalents of the isocyanate to 3 molar equivalents of the alcohol of the polycarbonate diol. Stated another way, a ratio of the isocyanate (e.g., a diisocyanate) to the polycarbonate diol typically ranges from 4 molar equivalents of the isocyanate to 1 molar equivalent of the alcohol of the polycarbonate diol, to 1.3 molar equivalents of the isocyanate to 1 molar equivalent of the alcohol of the polycarbonate diol. In select embodiments, a ratio of the isocyanate to the polycarbonate diol is 4 molar equivalents of isocyanate to 2 molar equivalents of the alcohol of the polycarbonate diol, or stated another way, 2 molar equivalents of isocyanate to 1 molar equivalent of alcohol of the polycarbonate diol. The closer the ratio of the isocyanate to the polycarbonate diol is to 1 molar equivalent of isocyanate to 1 molar equivalent of the alcohol of the polycarbonate diol, the higher the weight average molecular weight of the resulting polyurethane (meth)acrylate polymer produced in the polymerization reaction product of components.

A ratio of the isocyanate (e.g., a diisocyanate) to the (meth)acrylate mono-ol typically ranges from 4 molar equivalents of the isocyanate to 3 molar equivalents of the (meth)acrylate mono-ol, to 4 molar equivalents of the isocyanate to 1 molar equivalent of the (meth)acrylate mono-ol. Stated another way, a ratio of the isocyanate (e.g., a diisocyanate) to the (meth)acrylate mono-ol typically ranges from 1.3 molar equivalents of the isocyanate to 1 molar equivalent of the (meth)acrylate mono-ol, to 4 molar equivalents of the isocyanate to 1 molar equivalent of the (meth)acrylate mono-ol. In select embodiments, a ratio of the isocyanate to the (meth)acrylate mono-ol is 4 molar equivalents of the isocyanate to 2 molar equivalents of the (meth)acrylate mono-ol, or stated another way, 2 molar equivalents of the isocyanate to 1 molar equivalents of the (meth)acrylate mono-ol.

A ratio of the polycarbonate diol to the (meth)acrylate mono-ol typically ranges from 1 molar equivalent of the alcohol of the polycarbonate diol to 3 molar equivalents of the (meth)acrylate mono-ol, to 3 molar equivalents of the polycarbonate diol to 1 molar equivalents of the (meth)acrylate mono-ol. Stated another way, a ratio of the polycarbonate diol to the (meth)acrylate mono-ol typically ranges from 1 molar equivalent of the alcohol of the polycarbonate diol to 3 molar equivalents of the (meth)acrylate mono-ol, to 1 molar equivalent of the alcohol of the polycarbonate diol to 0.3 molar equivalents of the (meth)acrylate mono-ol. In select embodiments, a ratio of the polycarbonate diol to the (meth)acrylate mono-ol is 1 molar equivalent of the alcohol of the polycarbonate diol to 1 molar equivalent of the (meth)acrylate mono-ol.

Isocyanate

The components (e.g., included in the polymerization reaction product of components) comprise at least one isocyanate. Polyisocyanates which can be employed in the components can be any organic isocyanate having at least two free isocyanate groups. Included are aliphatic, cycloaliphatic, aromatic and araliphatic isocyanates. Any of the known polyisocyanates such as alkyl and alkylene polyisocyanates, cycloalkyl and cycloalkylene polyisocyanates, and combinations such as alkylene and cycloalkylene polyisocyanates can be employed.

In some embodiments, diisocyanates having the formula $R_{di}(NCO)_2$ can be used, with $R_{di}$ as defined above.

Specific examples of suitable diisocyanates include for instance and without limitation, 2,6-toluene diisocyanate (TDI), 2,4-toluene diisocyanate, methylenedicyclohexylene-4,4'-diisocyanate (H12MDI), 3-isocyanatomethyl-3,5, 5-trimethylcyclohexyl isocyanate (IPDI), 1,6-diisocyanatohexane (HDI), tetramethyl-m-xylene diisocyanate, a mixture of 2,2,4- and 2,4,4-trimethyl-1,6-diisocyanatohexane (TMXDI), trans-1,4-hydrogenated xylylene diisocyanates (H6XDI), cyclohexyl-1,4-diisocyanate, 4,4'-methylene diphenyl diisocyanate, 2,4'-methylene diphenyl diisocyanate, a mixture of 4,4'-methylene diphenyl diisocyanate and 2,4'-methylene diphenyl diisocyanate, 1,5- naphthalene diisocyanate, 1,4-tetramethylene diisocyanate, 1,4-phenylene diisocyanate, 2,6- and 2,4-toluene diisocyanate, 1,5-naphthylene diisocyanate, 2,4' and 4,4'-diphenylmethane diisocyanate, pentamethylene diisocyanate, dodecamethylene diisocyanate, 1,3-cyclopentane diisocyanate, 1,3-cyclohexane diisocyanate, methyl 2,4-cyclohexane diisocyanate, methyl-2,6-cyclohexane diisocyanate, 1,4-bis (isocyanatomethyl) cyclohexane, 1,3-bis (isocyanatomethyl) cyclohexane, 4,4'-toluidine diisocyanate, 4,4'-diphenyl ether diisocyanate, 1,3- or 1,4-xylylene diisocyanate, lysine diisocyanate methyl ester, 3,3'-dimethyl-4,4'-diphenylmethane diisocyanate, 3,3'-dimethyl-phenylene diisocyanate, 2,5-bis (isocyanate methyl)-bicyclo[2.2.1]heptane, 2,6-bis (isocyanate methyl)-bicyclo[2.2.1]heptane, bis (2-isocyanate ethyl) fumarate, 4-diphenylpropane diisocyanate, trans-cyclohexane-1,4-diisocyanatehydrogenated dimer acid diisocyanate, a norbornene diisocyanate, methylenebis 6-isopropyl-1,3-phenyl diisocyanate, and any combination thereof. In select embodiments, the diisocyanate comprises IPDI.

It is also possible to use higher-functional polyisocyanates known from polyurethane chemistry or else modified polyisocyanates, for example containing carbodiimide groups, allophanate groups, isocyanurate groups and/or biuret groups.

(Meth)Acrylate Mono-Ol

The components (e.g., included in the polymerization reaction product of components) comprise a (meth)acrylate mono-ol. Typically, the (meth)acrylate mono-ol comprises a hydroxy functional (meth)acrylate of Formula (II):

$$HO-Q-(A)_p \qquad (II)$$

wherein Q is a polyvalent organic linking group, A is a (meth)acryl functional group of the formula —XC(=O)C($R_3$)=$CH_2$, wherein X is O, S, or $NR_4$, $R_4$ is H or alkyl of 1 to 4 carbon atoms, $R_3$ is a lower alkyl of 1 to 4 carbon atoms or H, and wherein p is 1 or 2.

Q can be a straight or branched chain or cycle-containing connecting group. Q can include a covalent bond, an alkylene, an arylene, an aralkylene, an alkarylene. Q can optionally include heteroatoms such as O, N, and S, and combinations thereof. Q can also optionally include a heteroatom-containing functional group such as carbonyl or sulfonyl, and combinations thereof. In some embodiments, Q is a straight chain, branched chain, or cycle-containing connecting group selected from arylene, aralkylene, and alkarylene. In yet other embodiments, Q is a straight chain, branched chain, or cycle-containing connecting group containing heteroatoms such as O, N, and S and/or a heteroatom containing functional group such as carbonyl and sulfonyl. In other embodiments, Q is a branched or cycle-containing alkylene group that optionally contains heteroatoms selected from O, N, S, and/or a heteroatom-containing functional group such as carbonyl and sulfonyl.

In some embodiments, in the hydroxy functional (meth) acrylate of Formula (II), Q is an alkylene group, p is 1, and in the (meth)acryl functional group A, X is O and $R_2$ is methyl or H. In certain preferred embodiments, in the hydroxy functional (meth)acrylate of Formula (II), Q is an alkylene group, p is 1, and in the (meth)acryl functional group A, X is O and $R_2$ is methyl.

Suitable example (meth)acrylate mono-ols include for instance and without limitation, 2-hydroxyethyl (meth)acrylate, hydroxypropyl acrylate (all isomers), hydroxybutyl acrylate (all isomers), poly(e-caprolactone) mono[2-(meth) acryloxy ethyl] esters such as caprolactone monoacrylate available under the trade designation "SR-495" from Sartomer USA (Arkema Group) (Exton, Pa.), glycerol dimethacrylate, 1-(acryloxy)-3-(methacryloxy)-2-propanol, 2-hydroxy-3-phenyloxypropyl (meth)acrylate, 2-hydroxyalkyl (meth)acryloyl phosphate, 4-hydroxycyclohexyl (meth) acrylate, trimethylolpropane di(meth)acrylate, trimethylolethane di(meth)acrylate, 1,4-butanediol mono(meth)acrylate, neopentyl glycol mono(meth)acrylate, 1,6-hexanediol mono (meth)acrylate, 3-chloro-2-hydroxypropyl (meth)acrylate, 2-hydroxy-3-alkyloxy(meth)acrylate, polyethylene glycol mono(meth)acrylate, polypropylene glycol mono(meth) acrylate, ethylene oxide-modified phthalic acid (meth)acrylate, and 4-hydroxycyclohexyl (meth)acrylate.

Polycarbonate Diol

The components (e.g., included in the polymerization reaction product of components) comprise a polycarbonate diol, which was found to contribute to less water being absorbed during contact with water than orthodontic articles containing polyurethanes having alternate linking groups, such as polyethers. As orthodontic articles are used in the moisture-rich environment of a patient's mouth, the extent of water absorption is relevant to the composition of an orthodontic article. Select articles absorb less than 3%, less than 2.5%, less than 2%, less than 1.5%, or even less than 1% water when soaked in deionized water for 7 days at 37° C. The polycarbonate diol is of Formula (I):

$$H(O-R_1-O-C(=O))_m-O-R_2-OH \qquad (I)$$

wherein each of $R_1$ in each (O—$R_1$—O—C(=O)) repeat unit, and $R_2$ are independently an aliphatic, cycloaliphatic, or aliphatic/cycloaliphatic alkylene group and an average number of carbon atoms in a combination of all the $R_1$ and $R_2$ groups is 4 to 10, and m is (an integer of) 2 to 23. Stated another way, while some repeat units of $R_1$ and/or $R_2$ may have a carbon number of less than 4 (e.g., 2 or 3), enough of the repeat units have a sufficiently high carbon number that when the carbon numbers of all the repeat units of $R_1$ and $R_2$ in the polycarbonate diol of Formula (I) are averaged, that average falls within the range of 4 to 10, or any of 4 to 6, 4 to 7, 4 to 8, 4 to 9, 5 to 7, 5 to 8, 5 to 9, 5 to 10, 6 to 8, 6 to 9, 6 to 10, 7 to 9, 7 to 10, or 8 to 10. In select embodiments, at least one of $R_1$ or $R_2$ is —$CH_2CH_2CH(CH_3)CH_2CH_2$—, —$(CH_2)_6$—, or —$(CH_2)_4$—, and preferably a combination of —$CH_2CH_2CH(CH_3)CH_2CH_2$—, and —$(CH_2)_6$—.

In some embodiments, either the polycarbonate diol has a number average molecular weight (Mn) of greater than 1,000 grams per mole (g/mol) or a weighted average of all polycarbonate diols present in the components has a Mn of greater than 1,000 g/mol, wherein Mn is determined by OH value. Stated a different way, when the components contain a single polycarbonate diol of Formula (I), the polycarbonate diol has a Mn higher than 1,000 g/mol. When the components contain two or more polycarbonate diols (e.g., one or more being of Formula (I)), the Mn of at least one of the polycarbonate diols may be 1,000 g/mol or less with the proviso that a weighted average of all the Mn values of the two or more polycarbonate diols is higher than 1,000 g/mol. For instance, components containing two polycarbonate diols could include a molar ratio of a first polycarbonate diol having a Mn of about 500 g/mol of 1 to a second polycarbonate diol having a Mn of about 1,500 g/mol of 2, resulting in a weighted average Mn of 1,167 g/mol. In certain embodiments, a polycarbonate diol (or a weighted average of all the polycarbonate diols present in the components) has a number average molecular weight of 1,500 g/mol or higher.

In some embodiments, one or more polycarbonate diols are present having a Mn of 450 grams per mole (g/mol) or greater, 500 g/mol or greater, 550 g/mol or greater, 600 g/mol or greater, 650 g/mol or greater, 700 g/mol or greater, 750 g/mol or greater, 800 g/mol or greater, 850 g/mol or greater, 900 g/mol or greater, 950 g/mol or greater, or 1,000 g/mol or greater; and 3,200 g/mol or less, 3,100 g/mol or less, 3,000 g/mol or less, 2,900 g/mol or less, 2,800 g/mol or less, 2,700 g/mol or less, 2,600 g/mol or less, 2,500 g/mol or less, 2,400 g/mol or less, 2,300 g/mol or less, 2,200 g/mol or less, 2,100 g/mol or less, 2,000 g/mol or less, 1,900 g/mol or less, 1,800 g/mol or less, or 1,700 g/mol or less. Stated another way, the polycarbonate diol may have a Mn of 450 g/mol to 3,200 g/mol, 800 g/mol to 3,200 g/mol, 1,000 g/mol to 3,200 g/mol, 1,500 g/mol to 3,200 g/mol, 1,800 g/mol to 3,200 g/mol, 450 g/mol to 2,200 g/mol, 800 g/mol to 2,200 g/mol, 1,000 g/mol to 2,200 g/mol, 1,500 g/mol to 2,200 g/mol, or 1,800 g/mol to 2,200 g/mol. Inclusion of a polycarbonate diol having a Mn of greater than 3,200 g/mol, on the other hand, may negatively impact the stiffness of a photopolymerization reaction product of the photopolymerization composition, by increasing the elastomeric character of the photopolymerization reaction product. In select embodiments, the photopolymerizable composition is essentially free of any diols that have a Mn lower than the one or more polycarbonate diols present in the components.

Suitable polycarbonate diols for use in the components include for instance and without limitation, those commercially available from Kuraray Co. Ltd. (Tokyo, JP) under the trade designation "KURARAY POLYOL", e.g., specifically, each of the KURARAY POLYOL C series: C-590, C-1090, C-2050, C-2090, and C-3090; from Covestro LLC (Pittsburgh, Pa.) under the trade designation "DESMOPHEN", e.g., specifically, each of the DESMOPHEN C series: C-2100, C-2200, and C XP-2613.

Catalyst

The components (e.g., included in the polymerization reaction product of components) comprise a catalyst to catalyze the reaction of the at least one isocyanate, at least one (meth)acrylate mono-ol, and at least one polycarbonate diol. Typically, catalyst is included in an amount of 0.01 wt. % to 5 wt. %, based on the total weight of the polymerizable components.

Examples of suitable catalysts include for instance and without limitation, dioctyl dilaurate (DOTDL), stannous octoate, dibutyltin diacetate, dibutyltin dilaurate, dibutyltin mercaptide, dibutyltin thiocarboxylate, dibutyltin dimaleate, dioctyltin mercaptide, dioctyltin thiocarboxylate, lead 2-ethylhexanoate, tetra-alkyl titanates such as tetrabutyl titanate (TBT), triethylamine, N, N-dimethylcyclohexylamine, N-methylmorpholine, N-ethylmorpholine, N, N-dimethyl-p-toluidine, beta-(dimethylamino) propionitrile, N-methylpyrrolidone, N, N-dicyclohexylmethylamine, dimethylaminoethanol, dimethylamino-ethoxyethanol, triethylenediamine, N, N, N'-trimethyl aminoethyl ethanol amine, N, N, N', N'-tetramethylethylenediamine, N, N, N', N'-tetramethyl-1, 3-diamine, N, N, N', N'-tetramethyl-1,6-hexanediol-diamine, bis(N, N-dimethylaminoethyl) ether, N'-cyclohexyl-N, N-dimethyl-formamidine, N, N'-dimethylpiperazine, trimethyl piperazine, bis(aminopropyl) piperazine, N—(N, N'-dimethylaminoethyl) morpholine, bis(morpholinoethyl) ether, 1,2-dimethyl imidazole, N-methylimidazole, 1,4-di-amidines, diazabicyclo-[2.2.2]-octane (DABCO), 1,4-diazabicyclo [3.3.0]-oct-4-ene (DBN), 1,8-diazabicyclo-[4.3.0]-non-5-ene (DBN), 1,8-diazabicyclo[5.4.0]-undec-7-ene (DBU), and phenol salts, salts such as octyl acid salts, N, N, N', N"-pentamethyldiethylenetriamine, N, N, N', N"-pentamethyl dipropylenetriamine, tetramethylguanidine, N-cyclohexyl-N', N', N", N"-tetramethyl guanidine, N-methyl-N'-(2-dimethyl amino ethyl) piperazine, 1,3,5-tris (N, N-dimethyl-propyl)-hexahydro-1,3,5-triazine. In any embodiment, the catalyst comprises zinc, an amine, tin, zirconium, or bismuth. The catalyst can comprise tin, such as dibutyltin diacrylate. Preferably, however, the catalyst is free of tin, as tin catalysts may not be desirable to include in orthodontic articles that will be in contact with a patient's mouth.

The catalyst may comprise an organometallic zinc complex that is free of 2-ethylhexyl carboxylate and 2-ethylhexanoic acid, such as the zinc catalyst commercially available from King Industries, Inc. (Norwalk, Conn.) under the trade designation K-KAT XK-672, and/or other zinc catalysts available from King Industries, such as K-KAT XK-661, and K-KAT XK-635. Another suitable catalyst is bismuth neodecanoate, for instance commercially available from Sigma-Aldrich (St. Louis, Mo.), as well as bismuth catalysts available from King Industries under the trade designations K-KAT XK-651 and K-KAT 348. Available aluminum based catalysts include K-KAT 5218 from King Industries. Further, zirconium based catalysts include K-KAT 4205 and K-KAT 6212 available from King Industries.

Polymerized Reaction Product of Components

Orthodontic articles according to the present disclosure comprise a polymerized reaction product of components, which were described above. The polymerized reaction product of components contains at least one polyurethane (meth)acrylate polymer. Urethanes are prepared by the reaction of an isocyanate with an alcohol to form carbamate linkages. The polyurethane (meth)acrylate polymer typically provides toughness (e.g., at least a minimum tensile strength and/or modulus and flexibility, (e.g., at least a minimum elongation at break)) to the final orthodontic article. In addition to the urethane functionality, the polyurethane (meth)acrylate polymer further comprises a polycarbonate linking group. The linking group is a functional group that connects two or more urethane groups, and may be divalent, trivalent, or tetravalent, and preferably divalent. In addition, the polyurethane (meth)acrylate polymer optionally further comprises one or more functional groups selected from hydroxyl groups, carboxyl groups, amino groups, and siloxane groups. These functional groups can be reactive with other components of the photopolymerizable composition during polymerization. The polyurethane (meth)acrylate polymer preferably has a weight average molecular weight (Mw) of 3,000 g/mol or greater, 4,000 g/mol or greater, 5,000 g/mol or greater, 6,000 g/mol or greater, 6,000 g/mol or greater, 7,000 g/mol or greater, 8,000 g/mol or greater, 9,000 g/mol or greater, 10,000 g/mol or greater, 11,000 g/mol or greater, or 12,000 g/mol or greater; and 50,000 g/mol or less, 45,000 g/mol or less, 40,000 g/mol or less, 35,000 g/mol or less, 32,000 g/mol or less, 30,000 g/mol or less, 28,000 g/mol or less, 25,000 g/mol or less, 23,000 g/mol or less, 20,000 g/mol or less, or 18,000 g/mol or less. Stated another way, the polyurethane (meth)acrylate polymer may have a Mw of 3,000 g/mol to 50,000 g/mol, 6,000 g/mol to 40,000 g/mol, 6,000 g/mol to 18,000 g/mol, 6,000 g/mol to 35,000 g/mol, or 8,000 g/mol to 32,000 g/mol. Weight average molecular weight may be measured using gel permeation chromatography (GPC), for instance using the method described in the Examples below. Higher molecular weight of the polyurethane (meth)acrylates will result in higher viscosity resin formulations with comparable compositions and loadings, which makes them less flowable; lower molecular weight of the polyurethane (meth) acrylates will reduce their toughening effect on the cured orthodontic articles.

In some embodiments, the polyurethane (meth)acrylate is of Formula (VI):

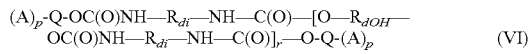
$$(A)_p\text{-Q-OC(O)NH}—R_{di}—\text{NH}—C(O)—[O—R_{dOH}—OC(O)NH—R_{di}—NH—C(O)]_r—O\text{-Q-}(A)_p \quad \text{(VI)}$$

wherein, A has the formula $—OC(=O)C(R_3)=CH_2$ wherein $R_3$ is an alkyl of 1 to 4 carbon atoms (e.g. methyl) or H, p is 1 or 2, Q is a polyvalent organic linking group as described above, $R_{di}$ is the residue of a diisocyanate, $R_{dOH}$ is the residue of a polycarbonate polyol, and r averages from 1 to 15. In some embodiments, r is no greater than 15, 14, 13, 12, 11, or 10. In some embodiments, r averages at least 2, 3, 4, or 5. In some embodiments, A is a methacryl functional group, such as methacrylate.

In some embodiments, the polymerized reaction product of components further comprises one or more side reaction products in addition to the polyurethane (meth)acrylate polymer. Depending on the selectivity of the catalyst and/or the weight ratios of the components, oligomers of the reactants may be produced. The order of addition of components in preparing the photopolymerizable composition affects the relative amounts of polymers and oligomers produced in the photopolymerized reaction product. For instance, adding the isocyanate to the polycarbonate diol first, followed by adding the monofunctional (meth)acrylate results in a higher ratio of polyurethane (meth)acrylate polymer to side products such as oligomers, than instead adding the monofunctional (meth)acrylate to the isocyanate first, followed by adding the polycarbonate diol.

Oligomers having a structure of monofunctional (meth) acrylate monomer-isocyanate-monofunctional (meth)acrylate monomer have been found to be a byproduct of the polymerization reaction of components in certain embodiments. It is possible to purify the polyurethane (meth) acrylate polymer to remove such side products. Alternatively, additional side products such as oligomers may be added to the polymerized reaction product, particularly when a specific reaction generates a small amount of one or more side products. It has been discovered that some side product components can improve at least one of modulus or extent of crosslinking after the photopolymerizable composition has been cured.

For example, photopolymerizable compositions optionally comprise a compound of Formula (III):

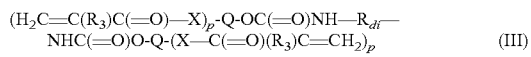
$$(H_2C=C(R_3)C(=O)—X)_p\text{-Q-OC}(=O)NH—R_{di}—NHC(=O)O\text{-Q-}(X—C(=O)(R_3)C=CH_2)_p \quad \text{(III)}$$

wherein X, Q, p, and $R_3$ are as defined for Formula (II), and $R_{di}$ is the residue of a diisocyanate as defined above. Typically, the compound of Formula (III) is produced during the polymerization of the components, as described above. The specific formulation of the components will affect how much of a compound of Formula (III) is made during the polymerization of components. For instance, the specificity of the catalyst towards catalyzing the formation of the polyurethane (meth)acrylate polymer can affect the amount of the compound of Formula (III) generated during the polymerization of the components. In certain embodiments, the compound of Formula (III) is added to the photopolymerizable composition, particularly when a smaller amount of the compound of Formula (III) is produced by the polymerization of components than desired. In any embodiment, the compound may advantageously improve crosslinking during the photopolymerization reaction, increase the modulus or the photopolymerization reaction product, or both. Regardless of if the compound of Formula (III) is formed during the polymerization of the components, added separately to the photopolymerizable composition, or both, in some embodiments the compound of Formula (III) is present in an amount of 0.05 weight percent (wt. %) or greater, based on the weight of the polymerizable composition, 0.1 wt. % or greater, 0.5 wt. % or greater, 1 wt. % or greater, 1.5 wt. % or greater, 2.5 wt. % or greater, 2 wt. % or greater, 3 wt. % or greater, 4 wt. % or greater, 5 wt. % or greater, 6 wt. % or greater, 7 wt. % or greater, 8 wt. % or greater, or 9 wt. % or greater; and 20 wt. % or less, 18 wt. % or less, 16 wt. % or less, 15 wt. % or less, 14 wt. % or less, 12 wt. % or less, or 10 wt. % or less, based on the weight of the polymerizable composition. Stated another way, the compound of Formula (III) may be present in the photopolymerizable composition in an amount of 0.05 to 20 weight percent (wt. %), 1.5 to 12 wt. %, 2.5 to 12 wt. %, 5 to 15 wt. %, 5 to 12 wt. %, 7 to 15 wt. %, 7 to 12 wt. %, or 5 to 20 wt. %, based on the weight of the polymerizable composition. Optionally, X is O in the compound of Formula (III). In select embodiments, the compound of Formula (III) is of Formula (IV):

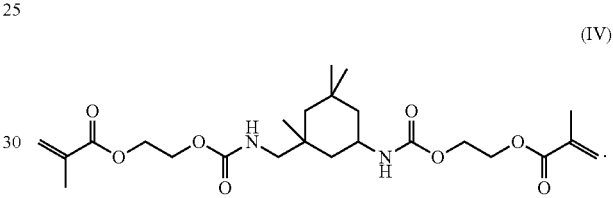

(IV)

Second Polymerization Reaction Product of Components:

In any embodiment, the photopolymerizable composition further comprises a second polymerization reaction product of components. The use of a second polyurethane(meth) acrylate polymer may provide somewhat different mechanical properties to the orthodontic article than using a single polyurethane(meth)acrylate polymer in the photopolymerizable composition. The components of the second polymerization reaction product comprise:

1) an isocyanate functional (meth)acrylate compound of the Formula (VII):

$$(A)_p\text{-Q-NCO} \quad \text{(VII)},$$

wherein A, p, and Q are as defined for Formula (II);

2) a polycarbonate diol of Formula (I):

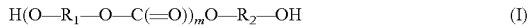
$$H(O—R_1—O—C(=O))_mO—R_2—OH \quad \text{(I)}$$

wherein each of $R_1$ in each $(O—R_1—O—C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23; and 3) a catalyst.

The second polymerization reaction product comprises a polyurethane (meth)acrylate polymer that is different from the first polyurethane (meth)acrylate polymer. In select embodiments, the second polymerization reaction product comprises a compound of Formula (VIII):

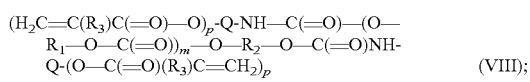
$$(H_2C=C(R_3)C(=O)—O)_p\text{-Q-NH}—C(=O)—(O—R_1—O—C(=O))_m—O—R_2—O—C(=O)NH\text{-Q-}(O—C(=O)(R_3)C=CH_2)_p \quad \text{(VIII)};$$

wherein Q, p, and $R_3$ are as defined for Formula (II) and $R_1$ and $R_2$ are as defined for Formula (I).

The compound of Formula (VIII) is typically obtained by reaction of a polycarbonate diol with an isocyanate functional (meth)acrylate compound in the presence of a catalyst. Examples of the isocyanate functional (meth)acrylate include isocyanatoethyl methacrylate, isocyanatoethoxyethyl methacrylate, isocyanatoethyl acrylate, and 1,1-(bisacryloyloxnethyl) ethyl isocyanate, which are for instance commercially available from Showa Denko (Tokyo, Japan). As an example, the compound of Formula (VIII) may, in select embodiments, be a compound of Formula (IX):

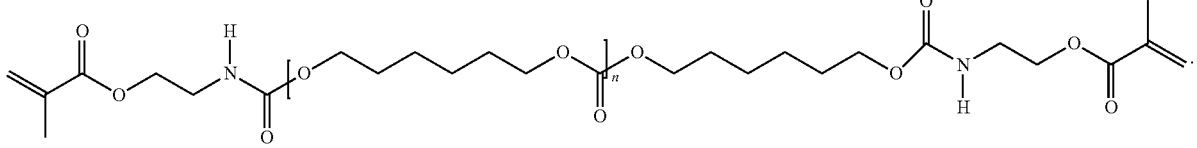

(IX)

In Formula (IX), n is about 6.7 for a 1000 molecular weight polycarbonate diol based on hexane diol.

In some embodiments, the second polymerization reaction product comprises a compound of Formula (XII):

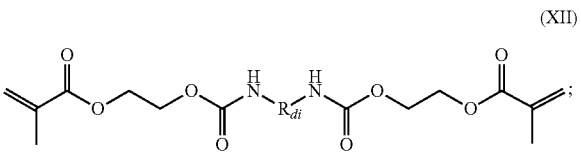

(XII)

wherein $R_{di}$ is a residue of a diisocyanate as defined above. In embodiments in which the diisocyanate is asymmetric, during polymerization the orientation of attachment of the residue of the diisocyanate to the nitrogen atoms of the carbamate linkages will vary and the polymerized reaction product will accordingly contain multiple polyurethane methacrylate structures.

Difunctional Component

The photopolymerizable compositions of the present disclosure optionally include at least one difunctional component, such as a difunctional (meth)acrylate monomer or oligomer. A difunctional component present in a photopolymerizable composition can co-react with the polyurethane (meth)acrylate polymer (e.g., is capable of undergoing addition polymerization).

A difunctional component (e.g., monomer) is optionally present in an amount of up to 15 wt. %, based on the total weight of the photopolymerizable composition, up to 12 wt. %, up to 10 wt. %, or up to 8 wt. %, based on the total weight of the photopolymerizable composition. Including more than 15 wt. % difunctional components may lead to more crosslinking than desired and decrease the elongation of the orthodontic article.

Suitable difunctional monomers include for instance and without limitation, compounds having the Formula (X):

H$_2$C=C(R$_3$)C(=O)X-Q-O—C(=O)NH—R$_{di}$—
NHC(=O)—O-Q-XC(=O)C(R$_3$)=CH$_2$ (X);

wherein $R_3$ is as defined for Formula (II) and Rai is the residue of a diisocyanate, or compounds having the Formula (XI):

H$_2$C=C(R$_3$)C(=O)—O-Q-NH—C(=O)—(O—
R$_1$—O—C(=O))$_m$—O—R$_2$—O—C(=O)NH-
Q-O—C(=O)C(R$_3$)=CH$_2$ (XI), wherein Q, X, and $R_3$ are as defined for Formula (II) and $R_1$ and $R_2$ are as defined for Formula (I). Additional suitable difunctional monomers include hydroxyethyl methacrylate diester of terephthalic acid, 1,12-dodecanediol dimethacrylate, alkoxylated hexanediol diacrylate, alkoxylated neopentyl glycol diacrylate, caprolactone modified neopentylglycol hydroxypivalate diacrylate, caprolactone modified neopentylglycol hydroxypivalate diacrylate, cyclohexanedimethanol diacrylate, diethylene glycol diacrylate, dipropylene glycol diacrylate, ethoxylated (10) bisphenol A diacrylate, ethoxylated (3) bisphenol A diacrylate, ethoxylated (30) bisphenol A diacrylate, ethoxylated (4) bisphenol A diacrylate, hydroxypivalaldehyde modified trimethylolpropane diacrylate, neopentyl glycol diacrylate, polyethylene glycol (200) diacrylate, polyethylene glycol (400) diacrylate, polyethylene glycol (600) diacrylate, propoxylated neopentyl glycol diacrylate, tetraethylene glycol diacrylate, tricyclodecanedimethanol diacrylate, triethylene glycol diacrylate, tripropylene glycol diacrylate, or any combination thereof. Further suitable difunctional monomers include the dimethacrylates of each of the above listed diacrylates.

Typically, the photopolymerizable compositions are essentially free of trihydric alcohols, which are alcohols having three hydroxyl groups. This is due to such alcohols increasing the hydrophilicity of the photopolymerizable composition, which may result in an undesirably high water absorption during use of an orthodontic article prepared from the photopolymerizable composition.

Additives

Photopolymerizable compositions described herein, in some instances, further comprise one or more additives, such as one or more additives selected from the group consisting of inhibitors, stabilizing agents, sensitizers, absorption modifiers, fillers and combinations thereof.

In addition, a photopolymerizable material composition described herein can further comprise one or more sensitizers to increase the effectiveness of one or more photoinitiators that may also be present. In some embodiments, a sensitizer comprises isopropylthioxanthone (ITX) or 2-chlorothioxanthone (CTX). Other sensitizers may also be used. If used in the photopolymerizable composition, a sensitizer can be present in an amount ranging of about 0.01% by weight or about 1% by weight, based on the total weight of the photopolymerizable composition.

A photopolymerizable composition described herein optionally also comprises one or more polymerization inhibitors or stabilizing agents. A polymerization inhibitor is often included in a photopolymerizable composition to provide additional thermal stability to the composition. A stabilizing agent, in some instances, comprises one or more anti-oxidants. Any anti-oxidant not inconsistent with the objectives of the present disclosure may be used. In some embodiments, for example, suitable anti-oxidants include various aryl compounds, including butylated hydroxytoluene (BHT), which can also be used as a polymerization inhibitor in embodiments described herein. In addition to or as an alternative, a polymerization inhibitor comprises methoxyhydroquinone (MEHQ).

In some embodiments, a polymerization inhibitor, if used, is present in an amount of about 0.001-2% by weight, 0.001 to 1% by weight, or 0.01-1% by weight, based on the total weight of the photopolymerizable composition. Further, if used, a stabilizing agent is present in a photopolymerizable composition described herein in an amount of about 0.1-5% by weight, about 0.5-4% by weight, or about 1-3% by weight, based on the total weight of the photopolymerizable composition.

A photopolymerizable composition as described herein can also comprise one or more UV absorbers including dyes, optical brighteners, pigments, particulate fillers, etc., to control the penetration depth of actinic radiation. One particularly suitable UV absorber is Tinuvin 326 (2-(5-chloro-2H-benzotriazol-2-yl)-6-(1,1-dimethylethyl)-4-methylphenol, obtained from BASF Corporation, Florham Park, N.J. Another particularly suitable UV absorber that is an optical brightener that is Tinopal OB, a benzoxazole, 2,2'-(2,5-thiophenediyl)bis[5-(1,1-dimethylethyl)], also available from BASF Corporation. Another suitable UV absorber is an optical brightener comprising a compound of Formula (V):

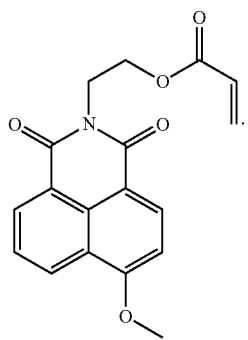

(V)

The compound of Formula V may be synthesized as described in detail in the Examples below.

The UV absorber, if used, can be present in an amount of about 0.001-5% by weight, about 0.01-1% by weight, about 0.1-3% by weight, or about 0.1-1% by weight, based on the total weight of the photopolymerizable composition.

Photopolymerizable compositions may include fillers, including nano-scale fillers. Examples of suitable fillers are naturally occurring or synthetic materials including, but not limited to: silica ($SiO_2$ (e.g., quartz)); alumina ($Al_2O_3$), zirconia, nitrides (e.g., silicon nitride); glasses and fillers derived from, for example, Zr, Sr, Ce, Sb, Sn, Ba, Zn, and Al; feldspar; borosilicate glass; kaolin (china clay); talc; zirconia; titania; and submicron silica particles (e.g., pyrogenic silicas such as those available under the trade designations AEROSIL, including "OX 50," "130," "150" and "200" silicas from Degussa Corp., Akron, Ohio and CAB-O-SIL M5 and TS-720 silica from Cabot Corp., Tuscola, Ill.). Organic fillers made from polymeric materials are also possible, such as those disclosed in International Publication No. WO09/045752 (Kalgutkar et al.).

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593 (Narang et al.). Examples of suitable colorants as described in U.S. Pat. No. 5,981,621 (Clark et al.) include 1-hydroxy-4-[4-methylphenylamino]-9,10-anthracenedione (FD&C violet No. 2); disodium salt of 6-hydroxy-5[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

Discontinuous fibers are also suitable fillers, such as fibers comprising carbon, ceramic, glass, or combinations thereof. Suitable discontinuous fibers can have a variety of compositions, such as ceramic fibers. The ceramic fibers can be produced in continuous lengths, which are chopped or sheared to provide the discontinuous ceramic fibers. The ceramic fibers can be produced from a variety of commercially available ceramic filaments. Examples of filaments useful in forming the ceramic fibers include the ceramic oxide fibers sold under the trademark NEXTEL (3M Company, St. Paul, Minn.). NEXTEL is a continuous filament ceramic oxide fiber having low elongation and shrinkage at operating temperatures, and offers good chemical resistance, low thermal conductivity, thermal shock resistance, and low porosity. Specific examples of NEXTEL fibers include NEXTEL 312, NEXTEL 440, NEXTEL 550, NEXTEL 610 and NEXTEL 720. NEXTEL 312 and NEXTEL 440 are refractory aluminoborosilicate that includes $Al_2O_3$, $SiO_2$ and $B_2O_3$. NEXTEL 550 and NEXTEL 720 are aluminosilica and NEXTEL 610 is alumina. During manufacture, the NEXTEL filaments are coated with organic sizings or finishes which serves as aids in textile processing. Sizing can include the use of starch, oil, wax or other organic ingredients applied to the filament strand to protect and aid handling. The sizing can be removed from the ceramic filaments by heat cleaning the filaments or ceramic fibers as a temperature of 700° C. for one to four hours.

The ceramic fibers can be cut, milled, or chopped so as to provide relatively uniform lengths, which can be accomplished by cutting continuous filaments of the ceramic material in a mechanical shearing operation or laser cutting operation, among other cutting operations. Given the highly controlled nature of certain cutting operations, the size distribution of the ceramic fibers is very narrow and allow to control the composite property. The length of the ceramic fiber can be determined, for instance, using an optical microscope (Olympus MX61, Tokyo, Japan) fit with a CCD Camera (Olympus DP72, Tokyo, Japan) and analytic software (Olympus Stream Essentials, Tokyo, Japan). Samples may be prepared by spreading representative samplings of the ceramic fiber on a glass slide and measuring the lengths of at least 200 ceramic fibers at 10× magnification.

Suitable fibers include for instance ceramic fibers available under the trade name NEXTEL (available from 3M Company, St. Paul, Minn.), such as NEXTEL 312, 440, 610 and 720. One presently preferred ceramic fiber comprises polycrystalline α-$Al_2O_3$. Suitable alumina fibers are described, for example, in U.S. Pat. No. 4,954,462 (Wood et al.) and U.S. Pat. No. 5,185,299 (Wood et al.). Exemplary alpha alumina fibers are marketed under the trade designation NEXTEL 610 (3M Company, St. Paul, Minn.). In some embodiments, the alumina fibers are polycrystalline alpha alumina fibers and comprise, on a theoretical oxide basis, greater than 99 percent by weight $Al_2O_3$ and 0.2-0.5 percent by weight $SiO_2$, based on the total weight of the alumina fibers. In other embodiments, some desirable polycrystalline, alpha alumina fibers comprise alpha alumina having an average grain size of less than one micrometer (or even, in some embodiments, less than 0.5 micrometer). In some embodiments, polycrystalline, alpha alumina fibers have an average tensile strength of at least 1.6 GPa (in some embodiments, at least 2.1 GPa, or even, at least 2.8 GPa). Suitable aluminosilicate fibers are described, for example, in U.S. Pat. No. 4,047,965 (Karst et al). Exemplary aluminosilicate fibers are marketed under the trade designations NEXTEL 440, and NEXTEL 720, by 3M Company (St. Paul, Minn.). Aluminoborosilicate fibers are described, for example, in U.S. Pat. No. 3,795,524 (Sowman). Exemplary aluminoborosilicate fibers are marketed under the trade designation NEXTEL 312 by 3M Company. Boron nitride fibers can be made, for example, as described in U.S. Pat. No. 3,429,722 (Economy) and U.S. Pat. No. 5,780,154 (Okano et al.).

Ceramic fibers can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers, which contain less than about 2% alkali or are substantially free of alkali (i.e., "E-glass" fibers). E-glass fibers are available from numerous commercial suppliers.

Examples of useful pigments include, without limitation: white pigments, such as titanium oxide, zinc phosphate, zinc sulfide, zinc oxide and lithopone; red and red-orange pigments, such as iron oxide (maroon, red, light red), iron/chrome oxide, cadmium sulfoselenide and cadmium mercury (maroon, red, orange); ultramarine (blue, pink and violet), chrome-tin (pink) manganese (violet), cobalt (violet); orange, yellow and buff pigments such as barium titanate, cadmium sulfide (yellow), chrome (orange, yellow), molybdate (orange), zinc chromate (yellow), nickel titanate (yellow), iron oxide (yellow), nickel tungsten titanium, zinc ferrite and chrome titanate; brown pigments such as iron oxide (buff, brown), manganese/antimony/titanium oxide, manganese titanate, natural siennas (umbers), titanium tungsten manganese; blue-green pigments, such as chrome aluminate (blue), chrome cobalt-alumina (turquoise), iron blue (blue), manganese (blue), chrome and chrome oxide (green) and titanium green; as well as black pigments, such as iron oxide black and carbon black. Combinations of pigments are generally used to achieve the desired color tone in the cured composition.

The use of florescent dyes and pigments can also be beneficial in enabling the printed composition to be viewed under black-light. A particularly useful hydrocarbon soluble fluorescing dye is 2,5-bis(5-tert-butyl-2-benzoxazolyl) 1 thiophene. Fluorescing dyes, such as rhodamine, may also be bound to cationic polymers and incorporated as part of the resin.

If desired, the compositions of the disclosure may contain other additives such as indicators, accelerators, surfactants, wetting agents, antioxidants, tartaric acid, chelating agents, buffering agents, and other similar ingredients that will be apparent to those skilled in the art. Additionally, medicaments or other therapeutic substances can be optionally added to the photopolymerizable compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions.

Combinations of any of the above additives may also be employed. The selection and amount of any one such additive can be selected by one of skill in the art to accomplish the desired result without undue experimentation.

Photopolymerizable compositions materials herein can also exhibit a variety of desirable properties, non-cured, cured, and as post-cured articles. A photopolymerizable composition, when non-cured, has a viscosity profile consistent with the requirements and parameters of one or more additive manufacturing devices (e.g., 3D printing systems). Advantageously, in many embodiments the photopolymerizable composition contains a minimal amount of solvent. For instance, the composition may comprise 95% to 100% solids, preferably 100% solids. In some instances, a photopolymerizable composition described herein when non-cured exhibits a dynamic viscosity of about 0.1-1,000 Pa·s, about 0.1-100 Pa·s, or about 1-10 Pa·s using a TA Instruments AR-G2 magnetic bearing rheometer using a 40 mm cone and plate measuring system at 40 degrees Celsius and at a shear rate of 0.1 l/s. In some cases, a photopolymerizable composition described herein when non-cured exhibits a dynamic viscosity of less than about 10 Pa·s.

Orthodontic Articles

A polymerized reaction product of a photopolymerizable composition according to the above disclosure comprises a shape of an orthodontic article. The conformability and durability of a cured orthodontic article made from the photopolymerizable compositions of the present disclosure can be determined in part by standard tensile, modulus, and/or elongation testing. The photopolymerizable compositions can typically be characterized by at least one of the following parameters after hardening.

The orthodontic article preferably exhibits at least one desirable physical property. These physical properties include the following: initial relaxation modulus, elongation at break, tensile strength, relaxation modulus at 30 minutes, percent loss of relaxation modulus, weight percent extractable components, and exhibiting peaks in loss modulus and tan delta with large temperature separation, and percent weight of water absorption. Preferably, the orthodontic article exhibits at least two different desirable physical properties, more preferably at least three different desirable physical properties, and most preferably at least initial relaxation modulus, elongation at break, and tensile strength. The values of these different physical properties are described below.

An orthodontic article optionally exhibits an initial relaxation modulus of 100 megapascals (MPa) or greater measured at 37° C. and 2% strain, as determined by Dynamic Mechanical Analysis (DMA) following conditioning (i.e., soaking) of a sample of the material of the orthodontic article in deionized water for 48 hours at room temperature (i.e., 22 to 25° C.) ("Water Conditioning"). The DMA procedure is described in detail in the Examples below. Preferably, an orthodontic article exhibits an initial relaxation modulus of 200 MPa or greater, 300 MPa or greater, 400 MPa or greater, 500 MPa or greater, 600 MPa or greater, 700 MPa or greater, 800 MPa or greater, 900 MPa or greater, 1,000 MPa or greater, 1,100 MPa or greater, or even 1,200 MPa or greater. In some embodiments, the initial relaxation modulus is no greater than about 3000, 2500, 2000, or 1500 MPa.

An orthodontic article optionally exhibits a (e.g., 30 minute) relaxation modulus of 100 MPa or greater as determined by DMA following 30 minutes of soaking in water at 37° C. under a 2% strain. The DMA procedure for relaxation modulus is described in detail in the Examples below, and is performed on a sample of the material of the orthodontic article following Water Conditioning and initial relaxation modulus testing. Preferably, an orthodontic article exhibits a (e.g., 30 minute) relaxation modulus of 200 MPa or greater, 300 MPa or greater, 400 MPa or greater, 500 MPa or greater, 600 MPa or greater, 700 MPa or greater, 800 MPa or greater, 900 MPa or greater, or even 1,000 MPa or greater. In some embodiments, the (e.g., 30 minute) relaxation modulus is no greater than about 1500, 1200, 1000, or 800 MPa.

An orthodontic article optionally exhibits a percent loss of relaxation modulus of 70% or less as determined by DMA. The loss is determined by comparing the initial relaxation modulus to the (e.g., 30 minute) relaxation modulus at 37° C. and 2% strain. It was discovered that orthodontic articles according to at least certain embodiments of the present disclosure exhibit a smaller loss in relaxation modulus following exposure to water than articles made of different materials. Preferably, an orthodontic article exhibits loss of relaxation modulus of 65% or less, 60% or less, 55% or less, 50% or less, 45% or less 40% or less, or even 35% or less. In some embodiments, the loss of relaxation modulus is 10%, 15%, or 20% or greater.

An orthodontic article optionally exhibits an elongation at break of a printed article of 20% or greater, as determined according to the Examples section below, after conditioning (i.e., soaking) of a sample of the material of the orthodontic article in phosphate-buffered saline having a pH of 7.4, for 24 hours at a temperature of 37° C. ("PBS Conditioning"). High elongation at break helps prevent the orthodontic article from being too brittle and potentially breaking during use by a patient. Preferably, an orthodontic article exhibits an elongation at break of 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, 100% or greater, 110% or greater, or even 120% or greater. In some embodiments, the elongation at break is no greater than 250%, 240%, 230%, 220%, 210%, 200%, 190%, 180%, 170%, 160%, 150%, or 140%.

An orthodontic article optionally exhibits a tensile strength at yield (or maximum) of 14 MPa or greater as determined according to ASTM-D638-14, using test specimen V, after PBS Conditioning. Strength at yield (i.e., yield strength) is defined as the maximum tensile stress a material can handle before it is permanently deformed. Tensile strength at break refers to the point on the stress-strain curve where the material breaks. As used herein, samples that yield have a distinct peak in the stress-strain curve. The stress-strain curves for brittle materials, however, do not have a yield point and are often linear over the full range of strain, eventually terminating in fracture at a maximum tensile strength without appreciable plastic flow. High tensile strength contributes to the orthodontic article having sufficient strength to be resilient during use in a patient's mouth. Preferably, an orthodontic article exhibits a tensile strength of 15 MPa or greater, 17 MPa or greater, 20 MPa or greater, 25 MPa or greater, 30 MPa or greater, 35 MPa or greater, 40 MPa or greater, 45 MPa or greater, 50 MPa or greater, or even 55 MPa or greater. In some embodiments, the tensile strength is no greater than 100 MPa, 95 MPa, 90 MPa, 85 MPa, 80 MPa, 75 MPa, or 70 MPa.

In select embodiments, an orthodontic article exhibits an initial relaxation modulus of 100 MPa, an elongation at break of 20% or greater, and a tensile strength of 14 MPa or greater. Similarly, an article may exhibit any combination of the preferred values described above, of each of the initial relaxation modulus, elongation at break, and tensile strength at yield. It was unexpectedly found that photopolymerizable compositions according to at least certain embodiments are capable of forming articles simultaneously having all three of these physical properties.

In select embodiments, dynamic mechanical analysis of articles showed a specific type of response that gave high elongation with high relaxation modulus at 30 minutes. When measured at a frequency of 1 Hz and a temperature heating ramp rate of 2° C./min from below −40° C. to above 200° C., some embodiments according to the present disclosure display a peak in the loss modulus below 20° C., more preferably below 15° C., most preferably below 10° C. In some embodiments, the peak loss modulus temperature is at least −70° C., −60° C., or −50° C. The term peak does not necessarily mean the global maximum value in loss modulus, but can be a local maximum value, or a shoulder on a larger peak. These articles tend to display high levels of elongation at break. In other embodiments, articles may display a tan delta peak >60° C., >80° C., more preferably >100° C., most preferably >110° C. In some embodiments, the peak tan delta temperature is no greater than 150° C., 140° C., 135° C., or 130° C. Articles which displayed high 30 minute relaxation modulus displayed tan delta peaks >60° C. Articles which displayed both high elongation and high 30 minute relaxation modulus displayed a peak in the loss modulus below 20° C. and a tan delta peak greater than 60° C. Loss modulus and tan delta are explained, for instance, in Sepe, M. P. (1998 Dynamic Mechanical Analysis for Plastics Engineering. William Andrew Publishing/Plastics Design Library).

In at least certain embodiments of orthodontic articles of the present disclosure, the articles are advantageously more resistant to staining than articles made from different, more hydrophilic components. For instance, dyes and other colored materials in beverages are typically hydrophilic, thus they will have a greater affinity for a more hydrophilic composition than a more hydrophobic composition.

In certain embodiments, an orthodontic article comprises 2 wt. % or less extractable components, 1 wt. % or less, 0.75 wt. % or less, 0.5 wt. % or less, or even 0.1% or less extractable components, based on the total weight of the article. Either an organic solvent or water can be used to extract component, as described in detail in the Examples below. Post-processing of the orthodontic article to assist in achieving a low extractable component-containing article is discussed in more detail below.

The above mechanical properties are particularly well suited for orthodontic articles that require resiliency and flexibility, along with adequate wear strength and low hygroscopicity.

Methods

In a second aspect, the present disclosure provides a method of making an orthodontic article. The method comprises:

a) obtaining a photopolymerizable composition comprising:
  i) a monofunctional (meth)acrylate monomer whose cured homopolymer has a $T_g$ of 90° C. or greater;
  ii) a photoinitiator; and
  iii) a polymerization reaction product of components, the components comprising:
    1) an isocyanate;
    2) a (meth)acrylate mono-ol;
    3) a polycarbonate diol of Formula (I):

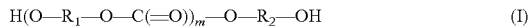
$$H(O-R_1-O-C(=O))_m-O-R_2-OH \quad (I)$$

wherein each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23; and
    4) a catalyst;
b) selectively curing the photopolymerizable composition; and
c) repeating steps a) and b) to form multiple layers and create the orthodontic article.

Photopolymerizable compositions described herein can be mixed by known techniques. In some embodiments, for instance, a method for the preparation of a photopolymerizable composition described herein comprises the steps of mixing all or substantially all of the components of the photopolymerizable composition, heating the mixture, and optionally filtering the heated mixture. Softening the mixture, in some embodiments, is carried out at a temperature of about 50° C. or in a range from about 50° C. to about 85° C. In some embodiments, a photopolymerizable composition described herein is produced by placing all or substantially all components of the composition in a reaction vessel and heating the resulting mixture to a temperature ranging from about 50° C. to about 85° C. with stirring. The heating and stirring are continued until the mixture attains a substantially homogenized state.

In many embodiments, the photopolymerizable composition is vat polymerized, as discussed in detail below.

The shape of the article is not limited, and typically comprises a shaped integral article, in which more than one variation in dimension is provided by a single integral article. For example, the article can comprise one or more channels, one or more undercuts, one or more perforations, or combinations thereof. Such features are typically not possible to provide in an integral article using conventional molding methods. Specific orthodontic articles are described in further detail below.

The components of the photopolymerizable composition are as discussed in detail above. In many embodiments, the photopolymerizable composition is cured using actinic radiation comprising UV radiation, e-beam radiation, visible radiation, or a combination thereof. Moreover, the method optionally further comprises post curing the orthodontic article using actinic radiation.

In certain embodiments, the method comprises vat polymerization of the photopolymerizable composition. When vat polymerization is employed, the radiation may be directed through a wall of a container (e.g., a vat) holding the photopolymerizable composition, such as a side wall or a bottom wall.

A photopolymerizable composition described herein in a cured state, in some embodiments, can exhibit one or more desired properties. A photopolymerizable composition in a "cured" state can comprise a photopolymerizable composition that includes a polymerizable component that has been at least partially polymerized and/or crosslinked. For instance, in some instances, a cured article is at least about 10% polymerized or crosslinked or at least about 30% polymerized or crosslinked. In some cases, a cured photopolymerizable composition is at least about 50%, at least about 70%, at least about 80%, or at least about 90% polymerized or crosslinked. A cured photopolymerizable composition can also be between about 10% and about 99% polymerized or crosslinked.

Fabricating an Orthodontic Article

Once prepared as set forth above, the photopolymerizable compositions of the present disclosure may be used in myriad additive manufacturing processes to create a variety of e.g., orthodontic articles. A generalized method 100 for creating three-dimensional articles is illustrated in FIG. 1. Each step in the method will be discussed in greater detail below. First, in Step 110 the desired photopolymerizable composition (e.g., comprising at least one polyurethane (meth)acrylate polymer) is provided and introduced into a reservoir, cartridge, or other suitable container for use by or in an additive manufacturing device. The additive manufacturing device selectively cures the photopolymerizable composition according to a set of computerized design instructions in Step 120. In Step 130, Step 110 and/or Step 120 is repeated to form multiple layers to create the article comprising a three-dimensional structure (i.e., an orthodontic article). Optionally uncured photopolymerizable composition is removed from the article in Step 140, further optionally, the article is subjected to additional curing to polymerize remaining uncured photopolymerizable components in the article in Step 150, and yet further optionally, the article is subjected to a heat treatment in Step 160.

Methods of printing a three-dimensional article or object described herein can include forming the article from a plurality of layers of a photopolymerizable composition described herein in a layer-by-layer manner. Further, the layers of a build material composition can be deposited according to an image of the three-dimensional article in a computer readable format. In some or all embodiments, the photopolymerizable composition is deposited according to preselected computer aided design (CAD) parameters.

Additionally, it is to be understood that methods of manufacturing a 3D article described herein can include so-called "stereolithography/vat polymerization" 3D printing methods. Other techniques for three-dimensional manufacturing are known, and may be suitably adapted to use in the applications described herein. More generally, three-dimensional fabrication techniques continue to become available. All such techniques may be adapted to use with photopolymerizable compositions described herein, provided they offer compatible fabrication viscosities and resolutions for the specified article properties. Fabrication may be performed using any of the fabrication technologies described herein, either alone or in various combinations, using data representing a three-dimensional object, which may be reformatted or otherwise adapted as necessary for a particular printing or other fabrication technology.

It is entirely possible to form a 3D article from a photopolymerizable composition described herein using vat polymerization (e.g., stereolithography). For example, in some cases, a method of printing a 3D article comprises retaining a photopolymerizable composition described herein in a fluid state in a container and selectively applying energy to the photopolymerizable composition in the container to solidify at least a portion of a fluid layer of the photopolymerizable composition, thereby forming a hardened layer that defines a cross-section of the 3D article. Additionally, a method described herein can further comprise raising or lowering the hardened layer of photopolymerizable composition to provide a new or second fluid layer of unhardened photopolymerizable composition at the surface of the fluid in the container, followed by again selectively applying energy to the photopolymerizable composition in the container to solidify at least a portion of the new or second fluid layer of the photopolymerizable composition to form a second solidified layer that defines a second cross-section of the 3D article. Further, the first and second cross-sections of the 3D article can be bonded or adhered to one another in the z-direction (or build direction corresponding to the direction of raising or lowering recited above) by the application of the energy for solidifying the photopolymerizable composition. Moreover, selectively applying energy to the photopolymerizable composition in the container can comprise applying actinic radiation, such as UV radiation, visible radiation, or e-beam radiation, having a sufficient energy to cure the photopolymerizable composition. A method described herein can also comprise planarizing a new layer of fluid photopolymerizable composition provided by raising or lowering an elevator platform. Such planarization can be carried out, in some cases, by utilizing a wiper or roller or a recoater. Planarization corrects the thickness of one or more layers prior to curing the material by evening the dispensed material to remove excess material and create a uniformly smooth exposed or flat up-facing surface on the support platform of the printer.

It is further to be understood that the foregoing process can be repeated a selected number of times to provide the 3D article. For example, in some cases, this process can be repeated "n" number of times. Further, it is to be understood that one or more steps of a method described herein, such as a step of selectively applying energy to a layer of photopolymerizable composition, can be carried out according to an image of the 3D article in a computer-readable format. Suitable stereolithography printers include the Viper Pro SLA, available from 3D Systems, Rock Hill, S.C. and the Asiga PICO PLUS 39, available from Asiga USA, Anaheim Hills, Calif.

Figure 2:
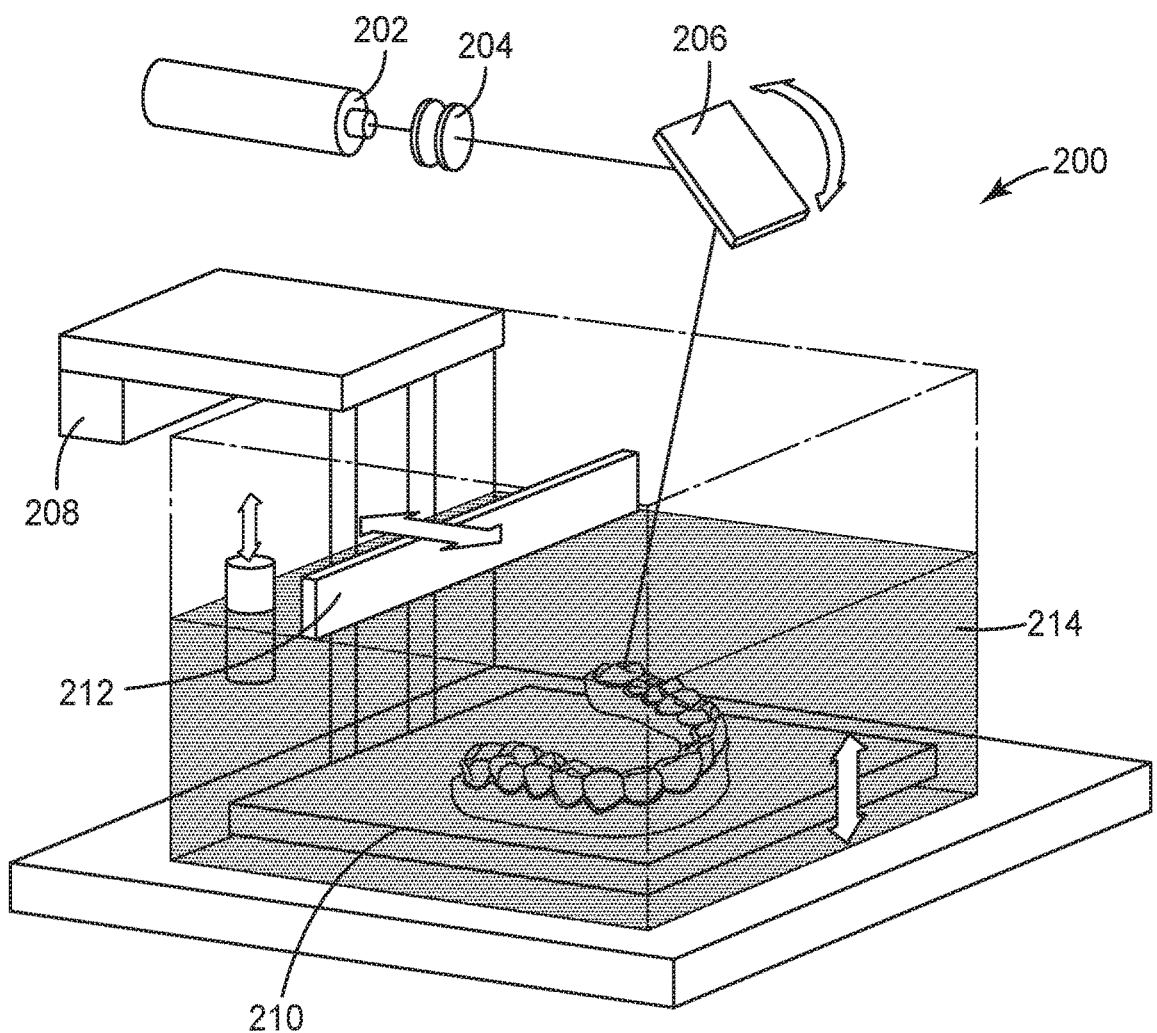
FIG. 2 is a generalized schematic of a stereolithography apparatus.

FIG. 2 shows an exemplary stereolithography apparatus ("SLA") that may be used with the photopolymerizable compositions and methods described herein. In general, the SLA 200 may include a laser 202, optics 204, a steering lens 206, an elevator 208, a platform 210, and a straight edge 212, within a vat 214 filled with the photopolymerizable composition. In operation, the laser 202 is steered across a surface of the photopolymerizable composition to cure a cross-section of the photopolymerizable composition, after which the elevator 208 slightly lowers the platform 210 and another cross section is cured. The straight edge 212 may sweep the surface of the cured composition between layers to smooth and normalize the surface prior to addition of a new layer. In other embodiments, the vat 214 may be slowly filled with liquid resin while an article is drawn, layer by layer, onto the top surface of the photopolymerizable composition.

A related technology, vat polymerization with Digital Light Processing ("DLP"), also employs a container of curable polymer (e.g., photopolymerizable composition). However, in a DLP based system, a two-dimensional cross section is projected onto the curable material to cure the desired section of an entire plane transverse to the projected beam at one time. All such curable polymer systems as may be adapted to use with the photopolymerizable compositions described herein are intended to fall within the scope of the term "vat polymerization system" as used herein. In certain embodiments, an apparatus adapted to be used in a continuous mode may be employed, such as an apparatus commercially available from Carbon 3D, Inc. (Redwood City, Calif.), for instance as described in U.S. Pat. Nos. 9,205,601 and 9,360,757 (both to De Simone et al.).

Figure 5:
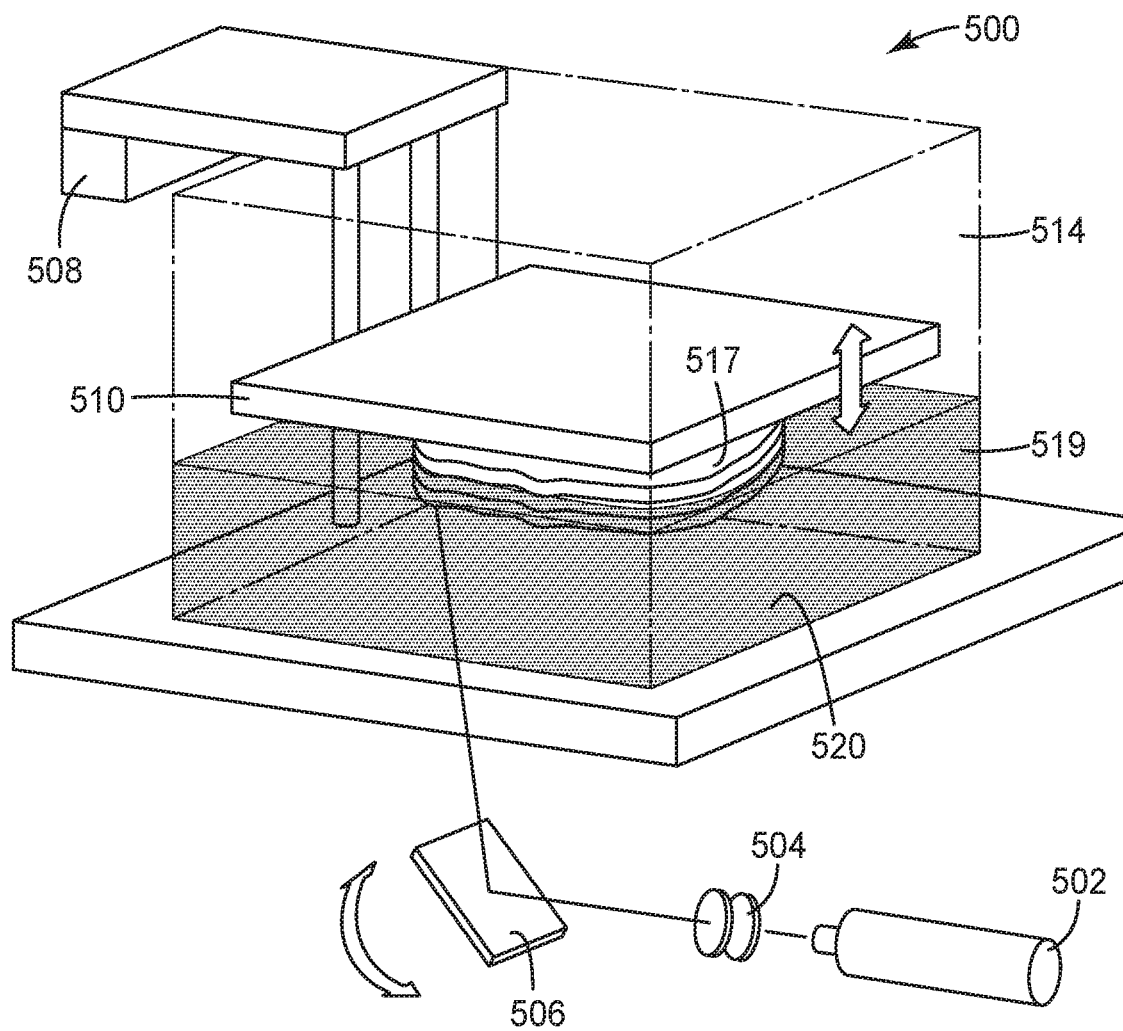
FIG. 5 is a generalized schematic of an apparatus in which radiation is directed through a container.

Referring to FIG. 5, a general schematic is provided of another SLA apparatus that may be used with photopolymerizable compositions and methods described herein. In general, the apparatus 500 may include a laser 502, optics 504, a steering lens 506, an elevator 508, and a platform 510, within a vat 514 filled with the photopolymerizable composition 519. In operation, the laser 502 is steered through a wall 520 (e.g., the floor) of the vat 514 and into the photopolymerizable composition to cure a cross-section of the photopolymerizable composition 519 to form an article 517, after which the elevator 508 slightly raises the platform 510 and another cross section is cured.

More generally, the photopolymerizable composition is typically cured using actinic radiation, such as UV radiation, e-beam radiation, visible radiation, or any combination thereof. The skilled practitioner can select a suitable radiation source and range of wavelengths for a particular application without undue experimentation.

After the 3D article has been formed, it is typically removed from the additive manufacturing apparatus and rinsed, (e.g., an ultrasonic, or bubbling, or spray rinse in a solvent, which would dissolve a portion of the uncured photopolymerizable composition but not the cured, solid state article (e.g., green body). Any other conventional method for cleaning the article and removing uncured material at the article surface may also be utilized. At this stage, the three-dimensional article typically has sufficient green strength for handling in the remaining optional steps of method 100.

It is expected in certain embodiments of the present disclosure that the formed article obtained in Step 120 will shrink (i.e., reduce in volume) such that the dimensions of the article after (optional) Step 150 will be smaller than expected. For example, a cured article may shrink less than 5% in volume, less than 4%, less than 3%, less than 2%, or even less than 1% in volume, which is contrast to other compositions that provide articles that shrink about 6-8% in volume upon optional post curing. The amount of volume percent shrinkage will not typically result in a significant distortion in the shape of the final object. It is particularly contemplated, therefore, that dimensions in the digital representation of the eventual cured article may be scaled according to a global scale factor to compensate for this shrinkage. For example, in some embodiments, at least a portion of the digital article representation can be at least 101% of the desired size of the printed appliance, in some embodiments at least 102%, in some embodiments at least 104%, in some embodiments, at least 105%, and in some embodiments, at least 110%.

A global scale factor may be calculated for any given photopolymerizable composition formulation by creating a calibration part according to Steps 110 and 120 above. The dimensions of the calibration article can be measured prior to post curing.

In general, the three-dimensional article formed by initial additive manufacturing in Step 120, as discussed above, is not fully cured, by which is meant that not all of the photopolymerizable material in the composition has polymerized even after rinsing. Some uncured photopolymerizable material is typically removed from the surface of the printed article during a cleaning process (e.g., optional Step 140). The article surface, as well as the bulk article itself, typically still retains uncured photopolymerizable material, suggesting further cure. Removing residual uncured photopolymerizable composition is particularly useful when the article is going to subsequently be post cured, to minimize uncured residual photopolymerizable composition from undesirably curing directly onto the article.

Further curing can be accomplished by further irradiating with actinic radiation, heating, or both. Exposure to actinic radiation can be accomplished with any convenient radiation source, generally UV radiation, visible radiation, and/or e-beam radiation, for a time ranging from about 10 to over 60 minutes. Heating is generally carried out at a temperature in the range of about 75-150° C., for a time ranging from about 10 to over 60 minutes in an inert atmosphere. So called post cure ovens, which combine UV radiation and thermal energy, are particularly well suited for use in the post cure processes of Step 150 and/or Step 160. In general, post curing improves the mechanical properties and stability of the three-dimensional article relative to the same three-dimensional article that is not post cured.

One particularly attractive opportunity for 3D printing is in the direct creation of orthodontic clear tray aligners. These trays, also known as aligners or polymeric or shell appliances, are provided in a series and are intended to be worn in succession, over a period of months, in order to gradually move the teeth in incremental steps towards a desired target arrangement. Some types of clear tray aligners have a row of tooth-shaped receptacles for receiving each tooth of the patient's dental arch, and the receptacles are oriented in slightly different positions from one appliance to the next in order to incrementally urge each tooth toward its desired target position by virtue of the resilient properties of the polymeric material. A variety of methods have been proposed in the past for manufacturing clear tray aligners and other resilient appliances. Typically, positive dental arch models are fabricated for each dental arch using additive manufacturing methods such as stereolithography described above. Subsequently, a sheet of polymeric material is placed over each of the arch models and formed under heat, pressure and/or vacuum to conform to the model teeth of each model arch. The formed sheet is cleaned and trimmed as needed and the resulting arch-shaped appliance is shipped along with the desired number of other appliances to the treating professional.

An aligner or other resilient appliance created directly by 3D printing would eliminate the need to print a mold of the dental arch and further thermoform the appliance. It also would allow new aligner designs and give more degrees of freedom in the treatment plan. Exemplary methods of direct printing clear tray aligners and other resilient orthodontic apparatuses are set forth in PCT Publication Nos. WO2016/109660 (Raby et al.), WO2016/148960 (Cinader et al.), and WO2016/149007 (Oda et al.) as well as US Publication Nos. US2011/0091832 (Kim, et al.) and US2013/0095446 (Kitching).

The following describes general methods for creating a clear tray aligner as printed appliance 300. However, other dental and orthodontic articles can be created using similar techniques and the photopolymerizable compositions of the present disclosure. Representative examples include, but are not limited to, the removable appliances having occlusal windows described in International Application Publication No. WO2016/109660 (Raby et al.), the removable appliances with a palatal plate described in US Publication No. 2014/0356799 (Cinader et al); and the resilient polymeric arch members described in International Application Nos. WO2016/148960 and WO2016/149007 (Oda et al.); as well as US Publication No. 2008/0248442 (Cinader et al.). Moreover, the photopolymerizable compositions can be used in the creation of indirect bonding trays, such as those described in International Publication No. WO2015/094842 (Paehl et al.) and US Publication No. 2011/0091832 (Kim, et al.) and other dental articles, including but not limited to crowns, bridges, veneers, inlays, onlays, fillings, and prostheses (e.g., partial or full dentures). Other orthodontic appliances and devices include, but not limited to, orthodontic brackets, buccal tubes, lingual retainers, orthodontic bands, class II and class III correctors, sleep apnea devices, bite openers, buttons, cleats, and other attachment devices.

Fabricating an Orthodontic Appliance with the Photopolymerizable Compositions

Figure 3:
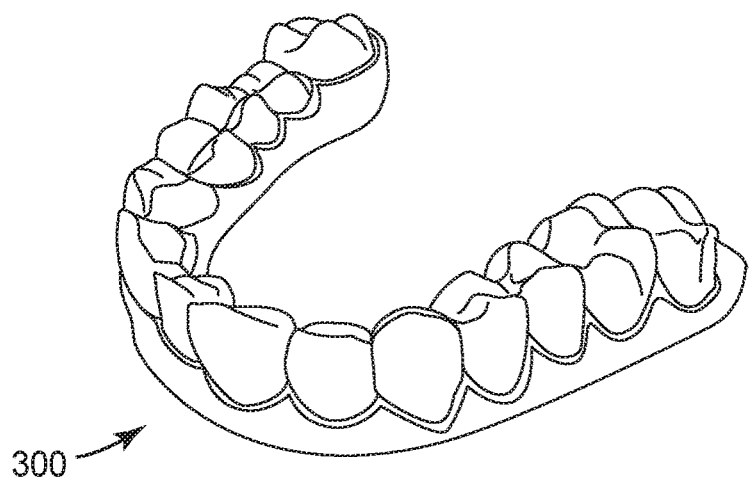
FIG. 3 is an isometric view of a printed clear tray aligner, according to one embodiment of the present disclosure.

One particularly interesting implementation of an article is generally depicted in FIG. 3. The additive manufactured article 300 is a clear tray aligner and is removably positionable over some or all of a patient's teeth. In some embodiments, the appliance 300 is one of a plurality of incremental adjustment appliances. The appliance 300 may comprise a shell having an inner cavity. The inner cavity is shaped to receive and resiliently reposition teeth from one tooth arrangement to a successive tooth arrangement. The inner cavity may include a plurality of receptacles, each of which is adapted to connect to and receive a respective tooth of the patient's dental arch. The receptacles are spaced apart from each other along the length of the cavity, although adjoining regions of adjacent receptacles can be in communication with each other. In some embodiments, the shell fits over all teeth present in the upper jaw or lower jaw. Typically, only certain one(s) of the teeth will be repositioned while others of the teeth will provide a base or anchor region for holding the dental appliance in place as it applies the resilient repositioning force against the tooth or teeth to be treated.

In order to facilitate positioning of the teeth of the patient, at least one of the receptacles may be aligned to apply rotational and/or translational forces to the corresponding tooth of the patient when the appliance 300 is worn by the patient in order to eventually align said tooth to a new desired position. In some particular examples, the appliance 300 may be configured to provide only compressive or linear forces. In the same or different examples, the appliance 300 may be configured to apply translational forces to one or more of the teeth within receptacles.

In some embodiments, the shell of the appliance 300 fits over some or all anterior teeth present in an upper jaw or lower jaw. Typically, only certain one(s) of the teeth will be repositioned while others of the teeth will provide a base or anchor region for holding the appliance in place as it applies the resilient repositioning force against the tooth or teeth to be repositioned. An appliance 300 can accordingly be designed such that any receptacle is shaped to facilitate retention of the tooth in a particular position in order to maintain the current position of the tooth.

Figure 4:
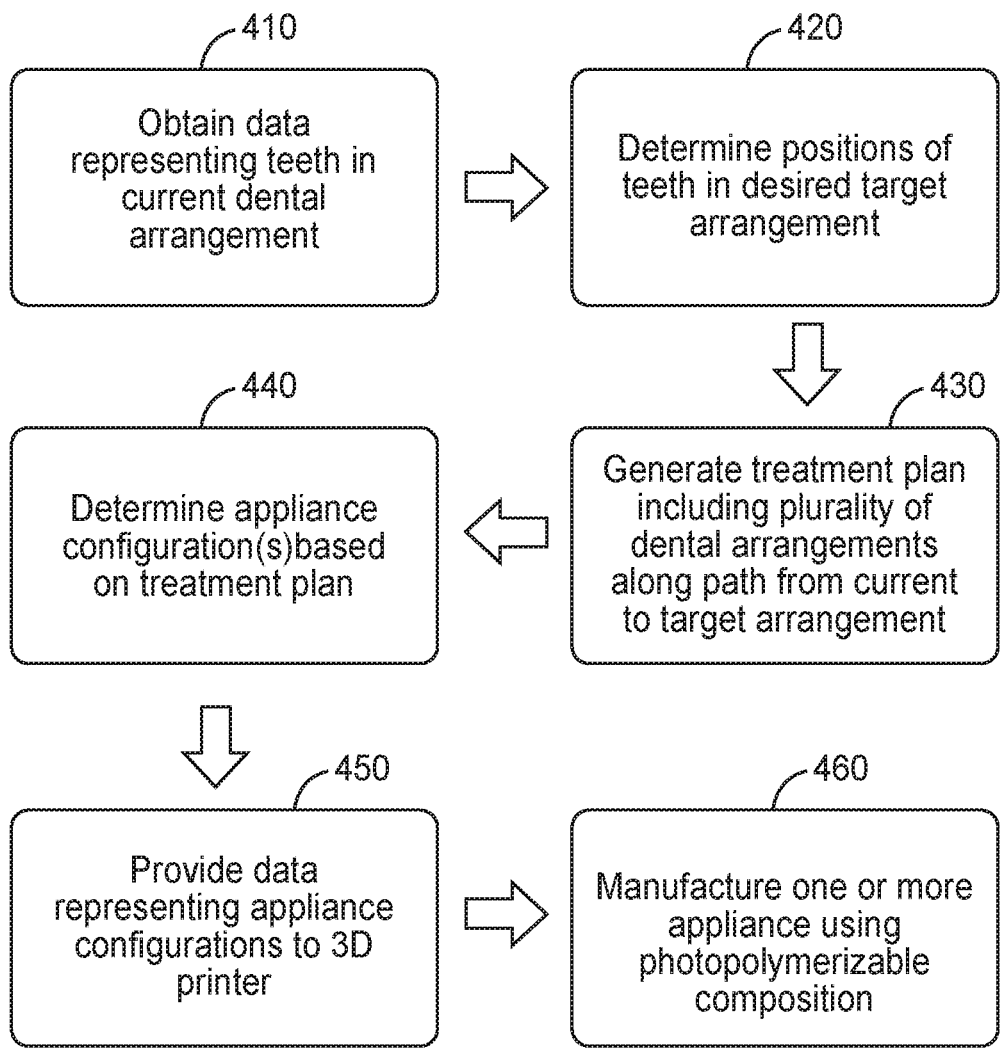
FIG. 4 is a flowchart of a process for manufacturing a printed orthodontic appliance according to the present disclosure.

A method 400 of creating an orthodontic appliance using the photopolymerizable compositions of the present disclosure can include general steps as outlined in FIG. 4. Individual aspects of the process are discussed in further detail below. The process includes generating a treatment plan for repositioning a patient's teeth. Briefly, a treatment plan can include obtaining data representing an initial arrangement of the patient's teeth (Step 410), which typically includes obtaining an impression or scan of the patient's teeth prior to the onset of treatment. The treatment plan will also include identifying a final or target arrangement of the patient's anterior and posterior teeth as desired (Step 420), as well as a plurality of planned successive or intermediary tooth arrangements for moving at least the anterior teeth along a treatment path from the initial arrangement toward the selected final or target arrangement (Step 430). One or more appliances can be virtually designed based on the treatment plan (Step 440), and image data representing the appliance designs can exported in STL format, or in any other suitable computer processable format, to an additive manufacturing device (e.g., a 3D printer system) (Step 450). An appliance can be manufactured using a photopolymerizable composition of the present disclosure retained in the additive manufacturing device (Step 460).

In some embodiments, a (e.g., non-transitory) machine-readable medium is employed in additive manufacturing of articles according to at least certain aspects of the present disclosure. Data is typically stored on the machine-readable medium. The data represents a three-dimensional model of an article, which can be accessed by at least one computer processor interfacing with additive manufacturing equipment (e.g., a 3D printer, a manufacturing device, etc.). The data is used to cause the additive manufacturing equipment to create an article comprising a reaction product of a photopolymerizable composition, the photopolymerizable composition includes a blend of: i) a monofunctional (meth) acrylate monomer whose cured homopolymer has a $T_g$ of 90° C. or greater; ii) a photoinitiator; and iii) a polymerization reaction product of components. The components include 1) an isocyanate; 2) a (meth)acrylate mono-ol; a polycarbonate diol of Formula (I): $H(O-R_1-O-C(=O))_m-O-R_2-OH$ (I); and 3) a catalyst. Each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is (an integer of) 2 to 23. The polymerized reaction product of the photopolymerizable composition has a shape of the orthodontic article. The details of the photopolymerizable composition are as described above.

Data representing an article may be generated using computer modeling such as computer aided design (CAD) data. Image data representing the (e.g., polymeric) article design can be exported in STL format, or in any other suitable computer processable format, to the additive manufacturing equipment. Scanning methods to scan a three-dimensional object may also be employed to create the data representing the article. One exemplary technique for acquiring the data is digital scanning. Any other suitable scanning technique may be used for scanning an article, including X-ray radiography, laser scanning, computed tomography (CT), magnetic resonance imaging (MRI), and ultrasound imaging. Other possible scanning methods are described, e.g., in U.S. Patent Application Publication No. 2007/0031791 (Cinader, Jr., et al.). The initial digital data set, which may include both raw data from scanning operations and data representing articles derived from the raw data, can be processed to segment an article design from any surrounding structures (e.g., a support for the article). In select embodiments, scanning techniques may include, for example, scanning a patient's mouth to customize an orthodontic article for the patient.

Figure 10:
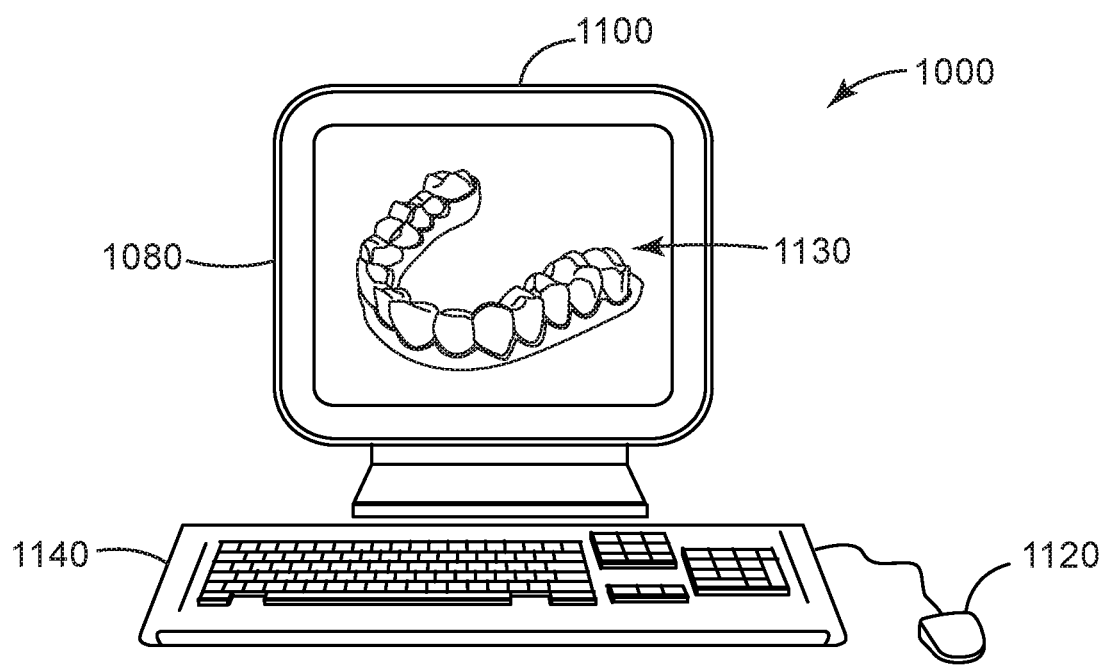
FIG. 10 is a schematic front view of an exemplary computing device 1000.

Often, machine-readable media are provided as part of a computing device. The computing device may have one or more processors, volatile memory (RAM), a device for reading machine-readable media, and input/output devices, such as a display, a keyboard, and a pointing device. Further, a computing device may also include other software, firmware, or combinations thereof, such as an operating system and other application software. A computing device may be, for example, a workstation, a laptop, a personal digital assistant (PDA), a server, a mainframe or any other general-purpose or application-specific computing device. A computing device may read executable software instructions from a computer-readable medium (such as a hard drive, a CD-ROM, or a computer memory), or may receive instructions from another source logically connected to computer, such as another networked computer. Referring to FIG. 10, a computing device 1000 often includes an internal processor 1080, a display 1100 (e.g., a monitor), and one or more input devices such as a keyboard 1140 and a mouse 1120. In FIG. 10, an aligner article 1130 is shown on the display 1100.

Figure 6:
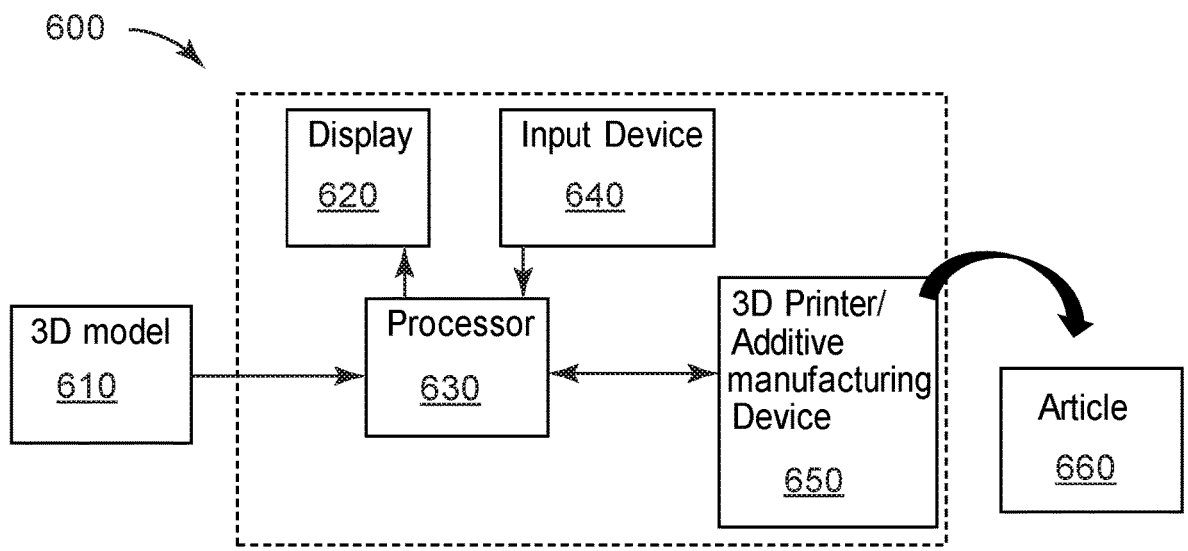
FIG. 6 is a block diagram of a generalized system 600 for additive manufacturing of an article.

Referring to FIG. 6, in certain embodiments, the present disclosure provides a system 600. The system 600 comprises a display 620 that displays a 3D model 610 of an article (e.g., an aligner 1130 as shown on the display 1100 of FIG. 10); and one or more processors 630 that, in response to the 3D model 610 selected by a user, cause a 3D printer/additive manufacturing device 650 to create a physical object of the article 660. Often, an input device 640 (e.g., keyboard and/or mouse) is employed with the display 620 and the at least one processor 630, particularly for the user to select the 3D model 610. The article 660 comprises a reaction product of a photopolymerizable composition, the photopolymerizable composition includes a blend of: i) a monofunctional (meth) acrylate monomer whose cured homopolymer has a $T_g$ of 90° C. or greater; ii) a photoinitiator; and iii) a polymerization reaction product of components. The components include 1) an isocyanate; 2) a (meth)acrylate mono-ol; a polycarbonate diol of Formula (I): $H(O-R_1-O-C(=O))_m-O-R_2-OH$ (I); and 3) a catalyst. Each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23. The polymerized reaction product of the photopolymerizable composition has a shape of the orthodontic article. The details of the photopolymerizable composition are as described above.

Figure 7:
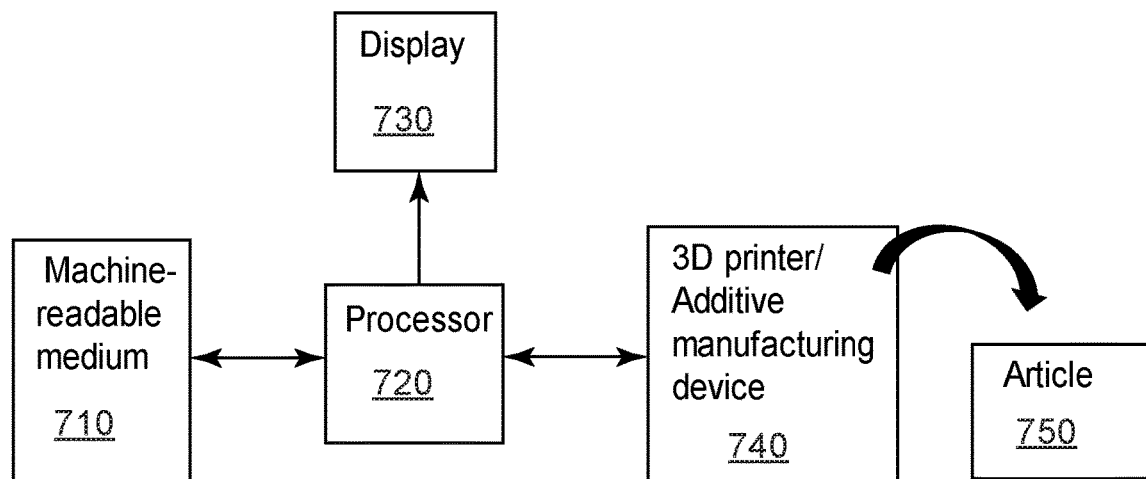
FIG. 7 is a block diagram of a generalized manufacturing process for an article.

Referring to FIG. 7, a processor 720 (or more than one processor) is in communication with each of a machine-readable medium 710 (e.g., a non-transitory medium), a 3D printer/additive manufacturing device 740, and optionally a display 730 for viewing by a user. The 3D printer/additive manufacturing device 740 is configured to make one or more articles 750 based on instructions from the processor 720 providing data representing a 3D model of the article 750 (e.g., an aligner article 1130 as shown on the display 1100 of FIG. 10) from the machine-readable medium 710.

Figure 8:
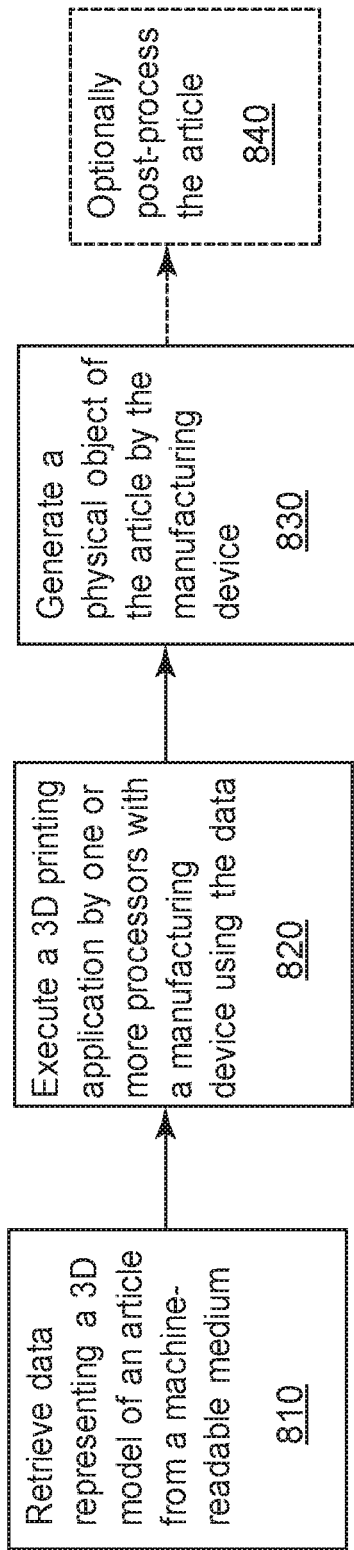
FIG. 8 is a high-level flow chart of an exemplary article manufacturing process.

Referring to FIG. 8, for example and without limitation, an additive manufacturing method comprises retrieving 810, from a (e.g., non-transitory) machine-readable medium, data representing a 3D model of an article according to at least one embodiment of the present disclosure. The method further includes executing 820, by one or more processors, an additive manufacturing application interfacing with a manufacturing device using the data; and generating 830, by the manufacturing device, a physical object of the article. The additive manufacturing equipment can selectively cure a photopolymerizable composition to form an article. The article comprises a reaction product of a photopolymerizable composition, the photopolymerizable composition includes a blend of: i) a monofunctional (meth)acrylate monomer whose cured homopolymer has a $T_g$ of 90° C. or greater; ii)

a photoinitiator; and iii) a polymerization reaction product of components. The components include 1) an isocyanate; 2) a (meth)acrylate mono-ol; a polycarbonate diol of Formula (I): H(O—R$_1$—O—C(=O))$_m$—O—R$_2$—OH (I); and 3) a catalyst. Each of R$_1$ in each (O—R$_1$—O—C(=O)) repeat unit and each R$_2$ are independently an aliphatic, cycloaliphatic, or aliphatic/cycloaliphatic alkylene group and an average number of carbon atoms in a combination of all the R$_1$ and R$_2$ groups is 4 to 10, and m is 2 to 23. The polymerized reaction product of the photopolymerizable composition has a shape of the orthodontic article. The details of the photopolymerizable composition are as described above. One or more various optional post-processing steps 840 may be undertaken. Typically, remaining unpolymerized photopolymerizable component may be cured. The article comprises an orthodontic article.

Figure 9:
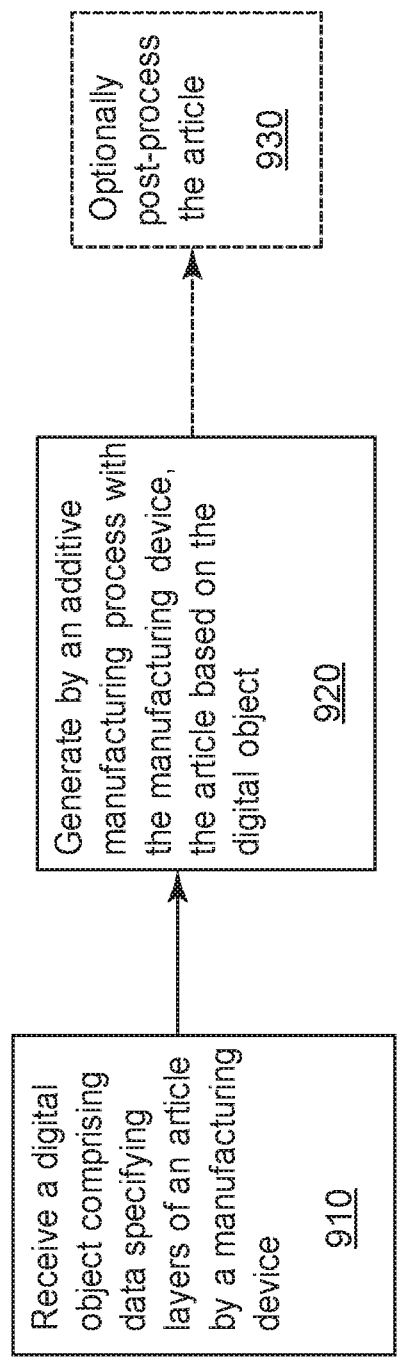
FIG. 9 is a high-level flow chart of an exemplary article additive manufacturing process.

Additionally, referring to FIG. 9, a method of making an article comprises receiving 910, by a manufacturing device having one or more processors, a digital object comprising data specifying a plurality of layers of an article; and generating 920, with the manufacturing device by an additive manufacturing process, the article based on the digital object. Again, the article may undergo one or more steps of post-processing 930.

Select Embodiments of the Disclosure

Embodiment 1 is an orthodontic article. The orthodontic article includes a reaction product of a photopolymerizable composition. The photopolymerizable composition includes a) a polymerized reaction product of a photopolymerizable composition. The photopolymerizable composition includes i) a monofunctional (meth)acrylate monomer whose cured homopolymer has a T$_g$ of 90° C. or greater; ii) a photoinitiator; and iii) a polymerization reaction product of components. The components include 1) an isocyanate; 2) a (meth)acrylate mono-ol; 3) a polycarbonate diol of Formula (I): H(O—R$_1$—O—C(=O))$_m$—O—R$_2$—OH (I); and 4) a catalyst. Each of R$_1$ in each (O—R$_1$—O—C(=O)) repeat unit and each R$_2$ are independently an aliphatic, cycloaliphatic, or aliphatic/cycloaliphatic alkylene group and an average number of carbon atoms in a combination of all the R$_1$ and R$_2$ groups is 4 to 10, and m is 2 to 23. The polymerized reaction product of the photopolymerizable composition has a shape of the orthodontic article.

Embodiment 2 is the orthodontic article of embodiment 1, wherein the (meth)acrylate mono-ol is of Formula (II): HO-Q-(A) (II). Q is a polyvalent organic linking group, A is a (meth)acryl functional group of the formula —XC(=O)C(R$_3$)=CH$_2$, wherein X is O, S, or NR$_4$, R$_4$ is H or alkyl of 1 to 4 carbon atoms, R$_3$ is a lower alkyl of 1 to 4 carbon atoms or H, and wherein p is 1 or 2.

Embodiment 3 is the orthodontic article of embodiment 2, wherein in the hydroxy functional (meth)acrylate of Formula (II), Q is an alkylene group, p is 1, and in the (meth)acryl functional group A, X is O and R$_3$ is methyl or H.

Embodiment 4 is the orthodontic article of embodiment 2 or embodiment 3, wherein in the hydroxy functional (meth)acrylate of Formula (II), Q is an alkylene group, p is 1, and in the (meth)acryl functional group A, X is O and R$_3$ is methyl.

Embodiment 5 is the orthodontic article of any of embodiments 1 to 4, wherein the photopolymerizable composition further includes a compound of Formula (III): (H$_2$C=C(R$_3$)C(=O)—X)$_p$-Q-OC(=O)NH—R$_{di}$—NHC(=O)O-Q-(X—C(=O)(R$_3$)C=CH$_2$)$_p$ (III). X, Q, p, and R$_3$ are as defined for Formula (II), and R$_{di}$ is the residue of a diisocyanate.

Embodiment 6 is the orthodontic article of embodiment 5, wherein the compound of Formula (III) is produced during the polymerization of the components.

Embodiment 7 is the orthodontic article of embodiment 5 or embodiment 6, wherein the compound of Formula (III) is added to the photopolymerizable composition.

Embodiment 8 is the orthodontic article of any of embodiments 5 to 7, wherein the compound of Formula (III) is present in an amount of 0.05 to 20 weight percent (wt. %), based on the weight of the polymerizable composition.

Embodiment 9 is the orthodontic article of any of embodiments 5 to 8, wherein the compound of Formula (III) is present in an amount of 1.5 to 12 wt. %, based on the weight of the polymerizable composition.

Embodiment 10 is the orthodontic article of any of embodiments 5 to 8, wherein the compound of Formula (III) is present in an amount of 5 to 20 wt. %, based on the weight of the polymerizable composition.

Embodiment 11 is the orthodontic article of any of embodiments 5 to 10, wherein X is O in the compound of Formula (III).

Embodiment 12 is the orthodontic article of any of embodiments 5 to 11, wherein the compound of Formula (III) is of Formula (IV):

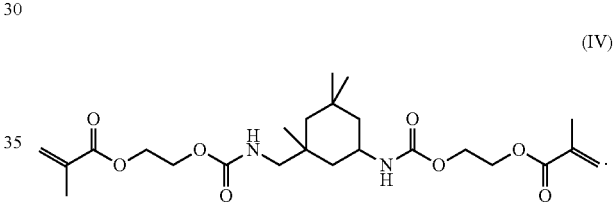

(IV)

Embodiment 13 is the orthodontic article of any of embodiments 1 to 12, wherein the photopolymerizable composition further includes a difunctional (meth)acrylate monomer or oligomer.

Embodiment 14 is the orthodontic article of any of embodiments 1 to 13, wherein the monofunctional (meth)acrylate monomer is selected from the group consisting of dicyclopentadienyl acrylate, dicyclopentanyl acrylate, isobornyl acrylate, dimethyl-1-adamantyl acrylate, cyclohexyl methacrylate, butyl methacrylate (e.g., tert-butyl methacrylate), 3,3,5-trimethylcyclohexyl methacrylate, butyl-cyclohexylmethacrylate (e.g., cis-4-tert-butyl-cyclohexylmethacrylate, 73/27 trans/cis-4-tert-butylcyclohexylmethacrylate, and/or trans-4-tert-butylcyclohexyl methacrylate) 2-decahydronapthyl methacrylate, 1-adamantyl acrylate, dicyclopentadienyl methacrylate, isobornyl methacrylate (e.g., d,l-isobornyl methacrylate), dimethyl-1-adamantyl methacrylate, bornyl methacrylate (e.g., d,l-bornyl methacrylate), 3-tetracyclo[4.4.0.1.1]dodecyl methacrylate, 1-adamantyl methacrylate, or combinations thereof.

Embodiment 15 is the orthodontic article of any of embodiments 1 to 14, wherein a weight ratio of the monofunctional (meth)acrylate monomer to the polyurethane (meth)acrylate polymer is 60:40 to 40:60.

Embodiment 16 is the orthodontic article of any of embodiments 1 to 15, wherein a weight ratio of the monofunctional (meth)acrylate monomer to the polyurethane (meth)acrylate polymer is 55:45 to 45:55.

Embodiment 17 is the orthodontic article of any of embodiments 1 to 16, wherein the isocyanate includes a diisocyanate selected from the group consisting of 2,6-toluene diisocyanate (TDI), methylenedicyclohexylene-4,4'-diisocyanate (H12MDI), 3-isocyanatomethyl-3,5,5-trimethylcyclohexyl isocyanate (IPDI), 1,6-diisocyanatohexane (HDI), tetramethyl-m-xylylene diisocyanate, a mixture of 2,2,4- and 2,4,4-trimethyl-1,6-diisocyanatohexame (TMXDI), trans-1,4-hydrogenated xylylene diisocyanates (H6XDI), or combinations thereof.

Embodiment 18 is the orthodontic article of any of embodiments 1 to 17, wherein the isocyanate includes IPDI.

Embodiment 19 is the orthodontic article of any of embodiments 1 to 18, wherein the polycarbonate diol has a molecular weight of 450 grams per mole (g/mol) to 3,200 g/mol, or 1,800 g/mol to 3,200 g/mol.

Embodiment 20 is the orthodontic article of any of embodiments 1 to 19, wherein the polycarbonate diol has a molecular weight of 800 g/mol to 2,200 g/mol or 1,800 g/mol to 2,200 g/mol Embodiment 21 is the orthodontic article of any of embodiments 1 to 20, wherein the photopolymerizable composition has a solids content of 95% to 100% solids.

Embodiment 22 is the orthodontic article of any of embodiments 1 to 21, wherein the photopolymerizable composition has a solids content of 100% solids.

Embodiment 23 is the orthodontic article of any of embodiments 1 to 22, wherein the photopolymerizable composition further includes a UV absorber comprising an optical brightener in an amount of 0.001 to 5% by weight, based on the total weight of the photopolymerizable composition.

Embodiment 24 is the orthodontic article of embodiment 23, wherein the optical brightener includes a compound of Formula (V):

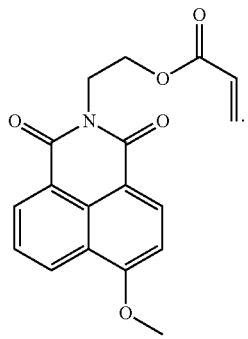

(V)

Embodiment 25 is the orthodontic article of any of embodiments 1 to 24, wherein the photopolymerizable composition further includes an inhibitor in an amount of 0.001 to 1 wt. %, based on the total weight of the photopolymerizable composition.

Embodiment 26 is the orthodontic article of any of embodiments 1 to 25, wherein the photoinitiator is present in an amount of 0.2 to 5 wt. %, based on the total weight of the photopolymerizable composition.

Embodiment 27 is the orthodontic article of any of embodiments 1 to 26, wherein the catalyst contains zinc.

Embodiment 28 is the orthodontic article of any of embodiments 1 to 27, wherein the catalyst includes an organometallic zinc complex and is free of 2-ethylhexyl carboxylate and 2-ethylhexanoic acid.

Embodiment 29 is the orthodontic article of any of embodiments 1 to 28, wherein the catalyst is free of tin.

Embodiment 30 is the orthodontic article of any of embodiments 1 to 29, wherein the catalyst contains bismuth.

Embodiment 31 is the orthodontic article of any of embodiments 1 to 30, wherein the polyurethane (meth) acrylate polymer has a weight average molecular weight (Mw) of 6,000 g/mol to 35,000 g/mol.

Embodiment 32 is the orthodontic article of any of embodiments 1 to 31, wherein the photopolymerizable composition further includes a difunctional monomer in an amount of up to 15 wt. %, based on the total weight of the photopolymerizable composition.

Embodiment 33 is the orthodontic article of embodiment 32, wherein the difunctional monomer includes a compound of Formula (X): $H_2C=C(R_3)C(=O)X-Q-O-C(=O)NH-R_{di}-NHC(=O)-O-Q-XC(=O)C(R_3)=CH_2$ (X), wherein $R_{di}$ is the residue of a diisocyanate, Q, X, and $R_3$ are as defined for Formula (II).

Embodiment 34 is the orthodontic article of embodiment 32, wherein the difunctional monomer includes a compound of Formula (XI): $H_2C=C(R_3)C(=O)-O-Q-NH-C(=O)-(O-R_1-O-C(=O))_m-O-R_2-O-C(=O)NH-Q-O-C(=O)C(R_3)=CH_2$ (XI) wherein Q and $R_3$ are as defined for Formula (II) and $R_1$ and $R_2$ are as defined for Formula (I).

Embodiment 35 is the orthodontic article of any of embodiments 1 to 34, wherein a ratio of the isocyanate to the polycarbonate diol ranges from 4 molar equivalents of the isocyanate to 1 molar equivalent of the alcohol of the polycarbonate diol, to 4 molar equivalents of the isocyanate to 3 molar equivalents of the alcohol of the polycarbonate diol.

Embodiment 36 is the orthodontic article of embodiment 35, wherein the ratio of the isocyanate to the alcohol of the polycarbonate diol is 4 molar equivalents of isocyanate to 2 molar equivalents of the alcohol of the polycarbonate diol.

Embodiment 37 is the orthodontic article of any of embodiments 1 to 36, wherein a ratio of the isocyanate to the (meth)acrylate mono-ol ranges from 4 molar equivalents of the isocyanate to 3 molar equivalents of the (meth)acrylate mono-ol to 4 molar equivalents of the isocyanate to 1 molar equivalent of the (meth)acrylate mono-ol.

Embodiment 38 is the orthodontic article of any of embodiments 1 to 37, wherein a ratio of the isocyanate to the (meth)acrylate mono-ol is 4 molar equivalents of the isocyanate to 2 molar equivalents of the (meth)acrylate mono-ol.

Embodiment 39 is the orthodontic article of any of embodiments 1 to 38, wherein a ratio of the polycarbonate diol to the (meth)acrylate mono-ol ranges from 1 molar equivalent of the alcohol of the polycarbonate diol to 3 molar equivalents of the (meth)acrylate mono-ol, to 3 molar equivalents of the alcohol of the polycarbonate diol to 1 molar equivalents of the (meth)acrylate mono-ol.

Embodiment 40 is the orthodontic article of any of embodiments 1 to 39, wherein a ratio of the polycarbonate diol to the (meth)acrylate mono-ol is 1 molar equivalent of the alcohol of the polycarbonate diol to 1 molar equivalent of the (meth)acrylate mono-ol.

Embodiment 41 is the orthodontic article of any of embodiments 1 to 40, wherein the polyurethane (meth) acrylate is of Formula (VI):

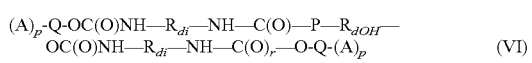

(VI)

wherein, A has the formula —OC(=O)C(R$_3$)=CH$_2$, wherein R$_3$ is an alkyl of 1 to 4 carbon atoms (e.g. methyl) or H, p is 1 or 2, Q is a polyvalent organic linking group as described above, R$_{di}$ is the residue of a diisocyanate, R$_{dOH}$ is the residue of a polycarbonate polyol, and r averages from 1 to 15.

Embodiment 42 is the orthodontic article of any of claims 1 to 41, wherein the photopolymerizable composition further includes a second polymerization reaction product of components. The components include 1) an isocyanate functional (meth)acrylate compound of Formula (VII): (A)$_p$-Q-NCO (VII), wherein A, p, and Q are as defined for Formula (II); 2) a polycarbonate diol of Formula (I): H(O—R$_1$—O—C(=O))$_m$O—R$_2$—OH (I); and 3) a catalyst. Each of R$_1$ in each (O—R$_1$—O—C(=O)) repeat unit and each R$_2$ are independently an aliphatic, cycloaliphatic, or aliphatic/cycloaliphatic alkylene group and an average number of carbon atoms in a combination of all the R$_1$ and R$_2$ groups is 4 to 10, and m is 2 to 23.

Embodiment 43 is the orthodontic article of any of embodiments 1 to 42, wherein the second polymerization reaction product includes a compound of Formula (VIII): (H$_2$C=C(R$_3$)C(=O)—O)$_p$-Q-NH—C(=O)—(O—R$_1$—O—C(=O))$_m$O—R$_2$—O—C(=O)NH-Q-(O—C(=O)(R$_3$)C=CH$_2$)$_p$ (VIII). Q, p, and R$_3$ are as defined for Formula (II) and R$_1$ and R$_2$ are as defined for Formula (I).

Embodiment 44 is the orthodontic article of embodiment 43, wherein the compound of Formula (VIII) is a compound of Formula (IX):

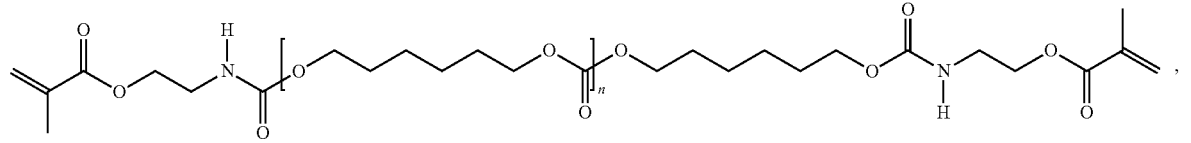

(IX)

wherein n is about 6.7 for a 1000 molecular weight polycarbonate diol based on hexane diol Embodiment 45 is the orthodontic article of any of embodiments 1 to 44, wherein a cured homopolymer of the monofunctional (meth)acrylate monomer has a T$_g$ of 100° C. or greater.

Embodiment 46 is the orthodontic article of any of embodiments 1 to 45, wherein the cured homopolymer of the monofunctional (meth)acrylate monomer has a T$_g$ of 170° C. or greater or 180° C. or greater.

Embodiment 47 is the orthodontic article of any of embodiments 1 to 46, wherein the monofunctional acrylate monomer includes a cycloaliphatic monofunctional (meth)acrylate.

Embodiment 48 is the orthodontic article of any of embodiments 1 to 47, wherein the monofunctional acrylate monomer includes isobornyl methacrylate.

Embodiment 49 is the orthodontic article of any of embodiments 1 to 48, exhibiting an initial relaxation modulus of 100 megapascals (MPa) or greater measured at 2% strain at 37° C.

Embodiment 50 is the orthodontic article of any of embodiments 1 to 49, exhibiting a percent loss of relaxation modulus of 70% or less.

Embodiment 51 is the orthodontic article of any of embodiments 1 to 50, exhibiting a percent loss of relaxation modulus of 40% or less.

Embodiment 52 is the orthodontic article of any of embodiments 1 to 51, exhibiting a relaxation modulus of 100 MPa or greater.

Embodiment 53 is the orthodontic article of any of embodiments 1 to 52, exhibiting an elongation at break of a printed article of 20% or greater.

Embodiment 54 is the orthodontic article of any of embodiments 1 to 53, exhibiting an elongation at break of a printed article of 70% or greater.

Embodiment 55 is the orthodontic article of any of embodiments 1 to 54, exhibiting a tensile strength at yield of 14 MPa or greater.

Embodiment 56 is the orthodontic article of any of embodiments 1 to 55, exhibiting a tensile strength at yield of 25 MPa or greater Embodiment 57 is the orthodontic article of any of embodiments 1 to 56, including 1 wt. % or less extractable components.

Embodiment 58 is the orthodontic article of any of embodiments 1 to 57, exhibiting a peak in loss modulus of 20° C. or less.

Embodiment 59 is the orthodontic article of embodiment 58, exhibiting a tan delta peak of 80° C. or greater.

Embodiment 60 is the orthodontic article of any of embodiments 1 to 57, wherein the orthodontic article includes a dental tray, a retainer, or an aligner.

Embodiment 61 is the orthodontic article of any of embodiments 1 to 58, wherein the orthodontic article includes an aligner.

Embodiment 62 is a method of making an orthodontic article. The method includes a) obtaining a photopolymerizable composition; b) selectively curing the photopolymerizable composition; and c) repeating steps a) and b) to form multiple layers and create the orthodontic article. The photopolymerizable composition includes i) a monofunctional (meth)acrylate monomer whose cured homopolymer has a T$_g$ of 90° C. or greater; ii) a photoinitiator; and iii) a polymerization reaction product of components. The components include 1) an isocyanate; 2) a (meth)acrylate monoool; 3) a polycarbonate diol of Formula (I): H(O—R$_1$—O—C(=O))$_m$—O—R$_2$—OH (I); and 4) a catalyst. Each of R$_1$ in each (O—R$_1$—O—C(=O)) repeat unit and each R$_2$ are independently an aliphatic, cycloaliphatic, or aliphatic/cycloaliphatic alkylene group and an average number of carbon atoms in a combination of all the groups R$_1$ and R$_2$ is 4 to 10, and m is 2 to 23.

Embodiment 63 is the method of embodiment 62, wherein the photopolymerizable composition is cured using actinic radiation including UV radiation, e-beam radiation, visible radiation, or a combination thereof.

Embodiment 64 is the method of embodiment 63, wherein the actinic radiation is directed through a wall of a container holding the photopolymerizable composition.

Embodiment 65 is the method of embodiment 63 or embodiment 64, wherein 90% or greater of the actinic radiation is absorbed over a distance of 150 micrometers of the photopolymerizable composition.

Embodiment 66 is the method of any of embodiments 62 to 65, wherein the photopolymerizable composition is cured through a floor of a container holding the photopolymerizable composition.

Embodiment 67 is the method of any of embodiments 62 to 66, further including post curing the orthodontic article using actinic radiation.

Embodiment 68 is the method of any of embodiments 62 to 67, wherein the method includes vat polymerization of the photopolymerizable composition.

Embodiment 69 is the method of any of embodiments 62 to 68, further including subjecting the orthodontic article to a heat treatment.

Embodiment 70 is the method of any of embodiments 62 to 69, wherein the photopolymerizable composition further includes at least one filler.

Embodiment 71 is the method of any of embodiments 62 to 70, wherein the photopolymerizable composition further includes at least one filler selected from silica, alumina, zirconia, and discontinuous fibers.

Embodiment 72 is the method of embodiment 71, wherein the discontinuous fibers include carbon, ceramic, glass, or combinations thereof.

Embodiment 73 is the method of any of embodiments 62 to 72, wherein the (meth)acrylate mono-ol is of Formula (II): HO-Q-(A)$_p$ (II). Q is a polyvalent organic linking group, A is a (meth)acryl functional group of the formula —XC(=O)C($R_3$)=CH$_2$, wherein X is O, S, or NR$_4$, R$_4$ is H or alkyl of 1 to 4 carbon atoms, R$_3$ is a lower alkyl of 1 to 4 carbon atoms or H, and wherein p is 1 or 2.

Embodiment 74 is the method of embodiment 73, wherein in the hydroxy functional (meth)acrylate of Formula (II), Q is an alkylene group, p is 1, and in the (meth)acryl functional group A, X is O and R$_3$ is methyl or H.

Embodiment 75 is the method of embodiment 73 or embodiment 74, wherein in the hydroxy functional (meth)acrylate of Formula (II), Q is an alkylene group, p is 1, and in the (meth)acryl functional group A, X is O and R$_3$ is methyl.

Embodiment 76 is the method of any of claims 62 to 75, wherein the photopolymerizable composition further includes a compound of Formula (III): (H$_2$C=C(R$_3$)C(=O)—X)$_p$-Q-OC(=O)NH—R$_{di}$—NHC(=O)O-Q-(X—C(=O)(R$_3$)C=CH$_2$)$_p$ (III). X, Q, p, and R$_3$ are as defined for Formula (II), and R$_{di}$ is the residue of a diisocyanate.

Embodiment 77 is the method of embodiment 76, wherein the compound of Formula (III) is produced during the polymerization of the components.

Embodiment 78 is the method of embodiment 76 or embodiment 77, wherein the compound of Formula (III) is added to the photopolymerizable composition.

Embodiment 79 is the method of any of claims 76 to 78, wherein the compound of Formula (III) is present in an amount of 0.05 to 20 weight percent (wt. %), based on the weight of the polymerizable composition.

Embodiment 80 is the method of any of embodiments 76 to 79, wherein the compound of Formula (III) is present in an amount of 1.5 to 12 wt. %, based on the weight of the polymerizable composition.

Embodiment 81 is the method of any of embodiments 76 to 79, wherein the compound of Formula (III) is present in an amount of 5 to 20 wt. %, based on the weight of the polymerizable composition.

Embodiment 82 is the method of any of embodiments 76 to 81, wherein X is O in the compound of Formula (III).

Embodiment 83 is the method of any of embodiments 76 to 82, wherein the compound of Formula (III) is of Formula (IV):

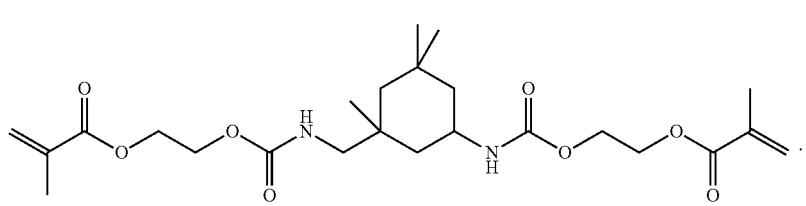

Embodiment 84 is the method of any of embodiments 62 to 83, wherein the photopolymerizable composition further includes a difunctional (meth)acrylate monomer or oligomer.

Embodiment 85 is the method of any of embodiments 62 to 84, wherein the monofunctional (meth)acrylate monomer is selected from the group consisting of dicyclopentadienyl acrylate, dicyclopentanyl acrylate, isobornyl acrylate, dimethyl-1-adamantyl acrylate, cyclohexyl methacrylate, butyl methacrylate (e.g., tert-butyl methacrylate), 3,3,5-trimethylcyclohexyl methacrylate, butyl-cyclohexylmethacrylate (e.g., cis-4-tert-butyl-cyclohexylmethacrylate, 73/27 trans/cis-4-tert-butylcyclohexylmethacrylate, and/or trans-4-tert-butylcyclohexyl methacrylate) 2-decahydronapthyl methacrylate, 1-adamantyl acrylate, dicyclopentadienyl methacrylate, isobornyl methacrylate (e.g., d,l-isobornyl methacrylate), dimethyl-1-adamantyl methacrylate, bornyl methacrylate (e.g., d,l-bornyl methacrylate), 3-tetracyclo[4.4.0.1.1]dodecyl methacrylate, 1-adamantyl methacrylate, or combinations thereof.

Embodiment 86 is the method of any of embodiments 62 to 85, wherein a weight ratio of the monofunctional (meth)acrylate monomer to the polyurethane (meth)acrylate polymer is 60:40 to 40:60.

Embodiment 87 is the method of any of embodiments 62 to 86, wherein a weight ratio of the monofunctional (meth)acrylate monomer to the polyurethane (meth)acrylate polymer is 55:45 to 45:55.

Embodiment 88 is the method of any of embodiments 62 to 87, wherein the isocyanate includes a diisocyanate selected from the group consisting of 2,6-toluene diisocyanate (TDI), methylenedicyclohexylene-4,4'-diisocyanate (H12MDI), 3-isocyanatomethyl-3,5,5-trimethylcyclohexyl isocyanate (IPDI), 1,6-diisocyanatohexane (HDI), tetramethyl-m-xylylene diisocyanate, a mixture of 2,2,4- and 2,4,4-trimethyl-1,6-diisocyanatohexame (TMXDI), trans-1,4-hydrogenated xylylene diisocyanates (H6XDI), or combinations thereof.

Embodiment 89 is the method of any of embodiments 62 to 88, wherein the isocyanate comprises IPDI.

Embodiment 90 is the method of any of embodiments 62 to 89, wherein the polycarbonate diol has a molecular weight of 450 grams per mole (g/mol) to 3,200 g/mol, or 1,800 g/mol to 3,200 g/mol.

Embodiment 91 is the method of any of embodiments 62 to 91, wherein the polycarbonate diol has a molecular weight of 800 g/mol to 2,200 g/mol, or 1,800 g/mol to 2,200 g/mol.

Embodiment 92 is the method of any of embodiments 62 to 91, wherein the photopolymerizable composition has a solids content of 95% to 100% solids.

Embodiment 93 is the method of any of embodiments 62 to 92, wherein the photopolymerizable composition has a solids content of 100% solids.

Embodiment 94 is the method of any of embodiments 62 to 93, wherein the photopolymerizable composition further comprises a UV absorber comprising an optical brightener in an amount of 0.001 to 5% by weight, based on the total weight of the photopolymerizable composition.

Embodiment 95 is the method of embodiment 94, wherein the optical brightener includes a compound of Formula (V):

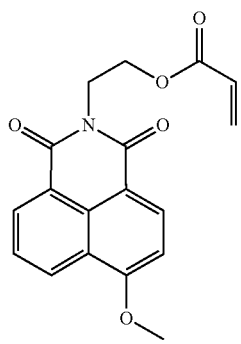

(V)

Embodiment 96 is the method of any of embodiments 62 to 95, wherein the photopolymerizable composition further includes an inhibitor in an amount of 0.001 to 1 wt. %, based on the total weight of the photopolymerizable composition.

Embodiment 97 is the method of any of embodiments 62 to 96, wherein the photoinitiator is present in an amount of 0.2 to 5 wt. %, based on the total weight of the photopolymerizable composition.

Embodiment 98 is the method of any of embodiments 62 to 97, wherein the catalyst contains zinc.

Embodiment 99 is the method of any of embodiments 62 to 98, wherein the catalyst includes an organometallic zinc complex and is free of 2-ethylhexyl carboxylate and 2-ethylhexanoic acid.

Embodiment 100 is the method of any of embodiments 62 to 99, wherein the catalyst is free of tin.

Embodiment 101 is the method of any of embodiments 62 to 100, wherein the catalyst contains bismuth.

Embodiment 102 is the method of any of embodiments 62 to 101, wherein the polyurethane (meth)acrylate polymer has a weight average molecular weight of 6,000 g/mol to 35,000 g/mol.

Embodiment 103 is the method of any of embodiments 62 to 102, wherein the photopolymerizable composition further includes a difunctional monomer in an amount of up to 15 wt. %, based on the total weight of the photopolymerizable composition.

Embodiment 104 is the method of embodiment 103, wherein the difunctional monomer includes a compound of Formula (X): $H_2C=C(R_3)C(=O)X-Q-O-C(=O)NH-R_{di}-NHC(=O)-O-Q-XC(=O)(R_3)=CH_2$ (X), wherein $R_{di}$ is the residue of a diisocyanate and $R_3$ is as defined for Formula (II).

Embodiment 105 is the method of embodiment 103, wherein the difunctional monomer includes a compound of Formula (XI): $H_2C=C(R_3)C(=O)-O-Q-NH-C(=O)-(O-R_1-O-C(=O))_m-O-R_2-O-C(=O)NH-Q-O-C(=O)C(R_3)=CH_2$ (XI) wherein Q and $R_3$ are as defined for Formula (II) and $R_1$ and $R_2$ are as defined for Formula (I).

Embodiment 106 is the method of any of embodiments 62 to 105, wherein a ratio of the isocyanate to the polycarbonate diol ranges from 4 molar equivalents of the isocyanate to 1 molar equivalent of the alcohol of the polycarbonate diol, to 4 molar equivalents of the isocyanate to 3 molar equivalents of the alcohol of the polycarbonate diol.

Embodiment 107 is the method of embodiment 106, wherein the ratio of the isocyanate to the polycarbonate diol is 4 molar equivalents of isocyanate to 2 molar equivalents of the alcohol of the polycarbonate diol.

Embodiment 108 is the method of any of embodiments 62 to 107, wherein a ratio of the isocyanate to the (meth)acrylate mono-ol ranges from 4 molar equivalents of the isocyanate to 3 molar equivalents of the (meth)acrylate mono-ol to 4 molar equivalents of the isocyanate to 1 molar equivalent of the (meth)acrylate mono-ol.

Embodiment 109 is the method of any of embodiments 62 to 108, wherein a ratio of the isocyanate to the (meth)acrylate mono-ol is 4 molar equivalents of the isocyanate to 2 molar equivalents of the (meth)acrylate mono-ol.

Embodiment 110 is the method of any of embodiments 62 to 109, wherein a ratio of the polycarbonate diol to the (meth)acrylate mono-ol ranges from 1 molar equivalent of the alcohol of the polycarbonate diol to 3 molar equivalents of the (meth)acrylate mono-ol, to 3 molar equivalents of the alcohol of the polycarbonate diol to 1 molar equivalents of the (meth)acrylate mono-ol.

Embodiment 111 is the method of any of embodiments 62 to 110, wherein a ratio of the polycarbonate diol to the (meth)acrylate mono-ol is 1 molar equivalent of the alcohol of the polycarbonate diol to 1 molar equivalent of the (meth)acrylate mono-ol.

Embodiment 112 is the method of any of embodiments 62 to 111, wherein the polyurethane (meth)acrylate is of Formula (VI):

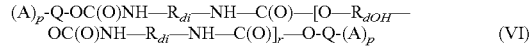

(VI)

wherein, A has the formula $-OC(=O)C(R_3)=CH_2$ wherein $R_3$ is an alkyl of 1 to 4 carbon atoms (e.g. methyl) or H, p is 1 or 2, Q is a polyvalent organic linking group as described above, Ra; is the residue of a diisocyanate, Ram is the residue of a polycarbonate polyol, and r averages from 1 to 15.

Embodiment 113 is the method of any of embodiments 62 to 112, the photopolymerizable composition further includes a second polymerization reaction product of components. The components include 1) an isocyanate functional (meth)acrylate compound of the Formula (VII): $(A)_p$-Q-NCO (VII), wherein A, p, and Q are as defined for Formula (II); 2) a polycarbonate diol of Formula (I): $H(O-R_1-O-C(=O))_m-O-R_2-OH$ (I); and 3) a catalyst. Each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23.

Embodiment 114 is the method of embodiment 113, wherein the second polymerization reaction product includes a compound of Formula (VIII): (H₂C=C(R₃)C(=O)—O)ₚ—O-Q-NH—C(=O)—(O—R₁—O—C(=O))ₘO—R₂—O—C(=O)NH-Q-(O—C(=O)(R₃)C=CH₂)ₚ (VIII). Q, p, and R₃ are as defined for Formula (II) and R₁ and R₂ are as defined for Formula (I).

Embodiment 115 is the method of embodiment 114, wherein the compound of Formula (VIII) is a compound of Formula (IX):

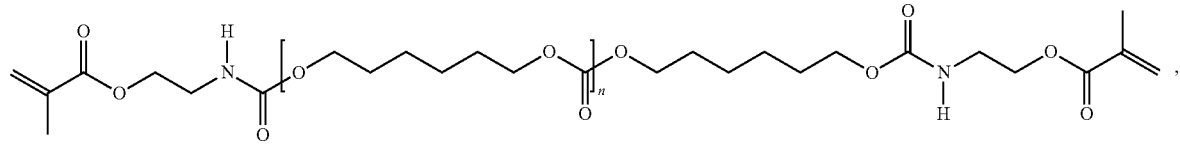

(IX)

wherein n is about 6.7 for a 1000 molecular weight polycarbonate diol based on hexane diol.

Embodiment 116 is the method of any of embodiments 62 to 115, wherein a cured homopolymer of the monofunctional (meth)acrylate monomer has a T$_g$ of 100° C. or greater.

Embodiment 117 is the method of any of embodiments 62 to 116, wherein the cured homopolymer of the monofunctional (meth)acrylate monomer has a T$_g$ of 170° C. or greater or 180° C. or greater.

Embodiment 118 is the method of any of embodiments 62 to 117, wherein the monofunctional acrylate monomer includes a cycloaliphatic monofunctional (meth)acrylate.

Embodiment 119 is the method of any of embodiments 62 to 118, wherein the monofunctional acrylate monomer includes isobornyl methacrylate.

Embodiment 120 is the method of any of embodiments 62 to 119, wherein the orthodontic article exhibits an initial relaxation modulus of 100 megapascals (MPa) or greater measured at 2% strain at 37° C.

Embodiment 121 is the method of any of embodiments 62 to 120, wherein the orthodontic article exhibits a percent loss of relaxation modulus of 70% or less.

Embodiment 122 is the method of any of claims 62 to 121, wherein the orthodontic article exhibits a percent loss of relaxation modulus of 40% or less.

Embodiment 123 is the method of any of embodiments 62 to 122, wherein the orthodontic article exhibits a relaxation modulus of 100 MPa or greater.

Embodiment 124 is the method of any of embodiments 62 to 123, wherein the orthodontic article exhibits an elongation at break of a printed article of 20% or greater.

Embodiment 125 is the method of any of embodiments 62 to 124, wherein the orthodontic article exhibits an elongation at break of a printed article of 70% or greater.

Embodiment 126 is the method of any of embodiments 62 to 125, wherein the orthodontic article exhibits a tensile strength at yield of 14 MPa or greater.

Embodiment 127 is the method of any of embodiments 62 to 126, wherein the orthodontic article exhibits a tensile strength at yield of 25 MPa or greater Embodiment 128 is the method of any of embodiments 62 to 127, wherein the orthodontic article contains 1 wt. % or less extractable components.

Embodiment 129 is the method of any of embodiments 62 to 128, wherein the orthodontic article exhibits a peak in loss modulus of 20° C. or less.

Embodiment 130 is the method of embodiment 129, exhibiting a tan delta peak of 80° C. or greater.

Embodiment 131 is the method of any of embodiments 62 to 130, wherein the orthodontic article includes a dental tray, a retainer, or an aligner.

Embodiment 132 is the method of any of embodiments 62 to 131, wherein the orthodontic article includes an aligner.

Embodiment 133 is a compound of Formula (V):

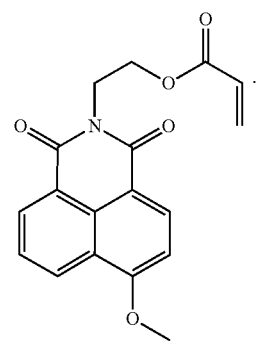

(V)

Embodiment 134 is an orthodontic article including a polymerized reaction product of a photopolymerizable composition. The photopolymerizable composition includes i) a monofunctional (meth)acrylate monomer whose cured homopolymer has a T$_g$ of 90° C. or greater; ii) a photoinitiator; iii) a UV absorber comprising a compound of Formula (V)

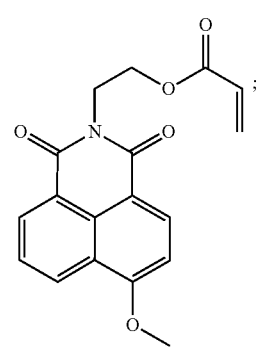

(V)

and
iv) a polymerization reaction product of components. The components include 1) an isocyanate; 2) a (meth)acrylate mono-ol; 3) a polycarbonate diol of Formula (I): H(O—R₁—O—C(=O))ₘ—O—R₂—OH (I); and 4) a catalyst. Each of R₁ in each (O—R₁—O—C(=O)) repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23. The polymerized reaction product of the photopolymerizable composition has a shape of the orthodontic article.

Embodiment 135 is a method of making an orthodontic article, the method including a) obtaining a photopolymerizable composition; b) selectively curing the photopolymerizable composition; and c) repeating steps a) and b) to form multiple layers and create the orthodontic article. The photopolymerizable composition includes i) a monofunctional (meth)acrylate monomer whose cured homopolymer has a $T_g$ of 90° C. or greater; ii) a photoinitiator; iii) a UV absorber comprising a compound of Formula (V)

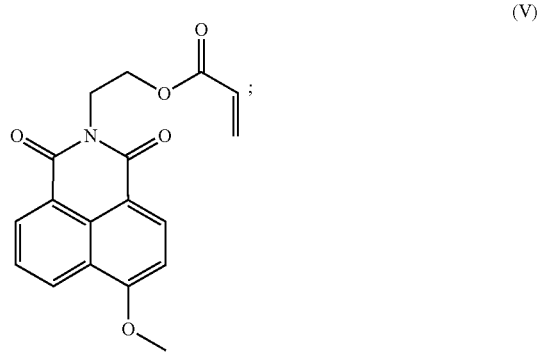 [SMILES: C=CC(=O)OCCN1C(=O)c2cccc3c(OC)ccc(c23)C1=O]

(V)

and
iv) a polymerization reaction product of components. The components include 1) an isocyanate; 2) a (meth)acrylate mono-ol; 3) a polycarbonate diol of Formula (I): H(O—$R_1$—O—C(=O))$_m$O—$R_2$—OH (I); and 4) a catalyst. Each of $R_1$ in each (O—$R_1$—O—C(=O)) repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23. The polymerized reaction product of the photopolymerizable composition has a shape of the orthodontic article.

Embodiment 136 is a non-transitory machine readable medium comprising data representing a three-dimensional model of an orthodontic article, when accessed by one or more processors interfacing with a 3D printer, causes the 3D printer to create an orthodontic article comprising a reaction product of a photopolymerizable composition. The photopolymerizable composition includes i) a monofunctional (meth)acrylate monomer whose cured homopolymer has a $T_g$ of 90° C. or greater; ii) a photoinitiator; and iii) a polymerization reaction product of components. The components include 1) an isocyanate; 2) a (meth)acrylate mono-ol; 3) a polycarbonate diol of Formula (I): H(O—$R_1$—O—C(=O))$_m$—O—$R_2$—OH (I); and 4) a catalyst. Each of $R_1$ in each (O—$R_1$—O—C(=O)) repeat unit and each $R_2$ are independently an aliphatic, cycloaliphatic, or aliphatic/cycloaliphatic alkylene group and an average of carbon atoms in a combination of all the $R_1$ and $R_2$ groups is 4 to 10, and m is 2 to 23. The polymerized reaction product of the photopolymerizable composition has a shape of the orthodontic article.

Embodiment 137 is a method including a) retrieving, from a non-transitory machine readable medium, data representing a 3D model of an article; b) executing, by one or more processors, a 3D printing application interfacing with a manufacturing device using the data; and c) generating, by the manufacturing device, a physical object of the orthodontic article. The orthodontic article includes a reaction product of a photopolymerizable composition. The photopolymerizable composition includes i) a monofunctional (meth)acrylate monomer whose cured homopolymer has a $T_g$ of 90° C. or greater; ii) a photoinitiator; and iii) a polymerization reaction product of components. The components include 1) an isocyanate; 2) a (meth)acrylate mono-ol; 3) a polycarbonate diol of Formula (I): H(O—$R_1$—O—C(=O))$_m$—O—$R_2$—OH (I); and 4) a catalyst. Each of $R_1$ in each (O—$R_1$—O—C(=O)) repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23. The polymerized reaction product of the photopolymerizable composition has a shape of the orthodontic article.

Embodiment 138 is a method including a) receiving, by a manufacturing device having one or more processors, a digital object comprising data specifying a plurality of layers of an orthodontic article; and b) generating, with the manufacturing device by an additive manufacturing process, the orthodontic article based on the digital object. The orthodontic article includes a reaction product of a photopolymerizable composition. The photopolymerizable composition includes i) a monofunctional (meth)acrylate monomer whose cured homopolymer has a $T_g$ of 90° C. or greater; ii) a photoinitiator; and iii) a polymerization reaction product of components. The components include 1) an isocyanate; 2) a (meth)acrylate mono-ol; 3) a polycarbonate diol of Formula (I): H(O—$R_1$—O—C(=O))$_m$—O—$R_2$—OH (I); and 4) a catalyst. Each of $R_1$ in each (O—$R_1$—O—C(=O)) repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23. The polymerized reaction product of the photopolymerizable composition has a shape of the orthodontic article.

Embodiment 139 is a system including a) a display that displays a 3D model of an orthodontic article; and b) one or more processors that, in response to the 3D model selected by a user, cause a 3D printer to create a physical object of an orthodontic article. The orthodontic article includes a reaction product of a photopolymerizable composition. The photopolymerizable composition includes i) a monofunctional (meth)acrylate monomer whose cured homopolymer has a $T_g$ of 90° C. or greater; ii) a photoinitiator; and iii) a polymerization reaction product of components. The components include 1) an isocyanate; 2) a (meth)acrylate mono-ol; 3) a polycarbonate diol of Formula (I): H(O—$R_1$—O—C(=O))$_m$—O—$R_2$—OH (I); and 4) a catalyst. Each of $R_1$ in each (O—$R_1$—O—C(=O)) repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23. The polymerized reaction product of the photopolymerizable composition has a shape of the orthodontic article.

Embodiment 140 is the article of any of embodiments 1 to 61, wherein the photopolymerizable composition comprises at least one hydrophilic monomer or polymer having a log P of less than 3, present in an amount of 1% to 25% by weight, based on the total weight of the photopolymerizable composition.

Embodiment 141 is the article of embodiment 140, wherein the photopolymerizable composition comprises at least one monofunctional (meth)acrylate monomer whose homopolymer has a $T_g$ of 150° C. or greater in an amount of 20% by weight or greater, based on the total weight of the photopolymerizable composition.

Embodiment 142 is the method of any of embodiments 62 to 131, wherein the photopolymerizable composition comprises at least one hydrophilic monomer or polymer having a log P of less than 3, present in an amount of 1% to 25% by weight, based on the total weight of the photopolymerizable composition.

Embodiment 143 is the method of embodiment 142, wherein the photopolymerizable composition comprises at least one monofunctional (meth)acrylate monomer whose homopolymer has a $T_g$ of 150° C. or greater in an amount of 20% by weight or greater, based on the total weight of the photopolymerizable composition.

EXAMPLES

Objects and advantages of this disclosure are further illustrated by the following examples, but the particular materials and amounts thereof recited in these examples, as well as other conditions and details, should not be construed to unduly limit this disclosure.

Materials

Unless otherwise noted, all parts, percentages, ratios, etc. in the examples and the rest of the specification are by weight. The Materials Table (below) lists materials used in the examples and their sources.

Materials Table

| Material designation | Description |
|---|---|
| 1-Adamantanol | Obtained from TCI America, Portland, OR. |
| 212-20 | A polycarbonate diol of about 1500 MW made with $CO_2$ and propylene oxide obtained as "CONVERGE POLYOL 212-20" from Aramco, Dhahran, Saudi Arabia. |
| 4-chloro-1,8-naphthalic anhydride | Obtained from Alfa Aesar, Haverhill, MA. |
| 4-hydroxy-TEMPO | 4-hydroxy-2,2,6,6-tetramethylpiperidine 1-oxyl, obtained from Sigma Aldrich, St. Louis, MO. |
| 4-tert-butylcyclohexanol | 4-tert-butylcyclohexanol, mixture of isomers, obtained from TCI America, Portland, OR. |
| Acetonitrile | Omnisolv HPLC grade obtained from EMD Millipore, a part of Merck KGaA, Darmstadt, Germany. |
| Acrylic acid | Obtained from Alfa Aesar, Haverill, MA. |
| Acryloyl chloride | Obtained from Sigma-Aldrich Chemical Company, St. Louis, MO. |
| Ammonium formate | Obtained as a 5M aqueous solution from Agilent Technologies, Waldbronn, Germany. |
| Anhydrous magnesium sulfate | Obtained from EMD Millipore, a part of Merck KGaA. |
| BHT | 2,6-di-t-butyl-4-methylphenol obtained from Alfa Aesar, Haverhill, MA. |
| BiN | Bismuth neodecanoate obtained from Sigma-Aldrich, St. Louis, MO. |
| C XP-2613 | A polycarbonate diol of about 2000 MW of what is believed to have about a 75:25 mole ratio of butane diol:hexane diol, obtained as "DESMOPHEN C XP-2613" from Covestro LLC., Leverkusen, Germany. |
| C-1090 | A polycarbonate diol of about 1000 MW made with about a 9:1 mole ratio of 3-methyl-1,5-pentanediol (MPD):hexane diol (HD), (i.e., 90% "MPD,) obtained as "KURARAY POLYOL C-1090 from Kuraray Co. Ltd., Tokyo, Japan. |
| C-2050 | A polycarbonate diol of about 2000 MW made with about a 50% (i.e., 5:5) mole ratio of (MPD):(HD), obtained as "KURARAY POLYOL C-2050" from Kuraray Co. Ltd. |
| C-2090 | A polycarbonate diol of about 2000 MW made with about a 9:1 mole ratio of (MPD):(HD), obtained as "KURARAY POLYOL C-2090" from Kuraray Co. Ltd. |
| C-2100 | A polycarbonate diol of about 1000 MW that it is believed uses HD as the diol, obtained as "DESMOPHEN C-2100" from Covestro LLC. |
| C-2200 | A polycarbonate diol of about 2000 MW that it is believed uses HD as the diol, obtained as "DESMOPHEN C-2200" from Covestro LLC. |
| C-3090 | A polycarbonate diol of about 3000 MW made with about a 9:1 mole ratio of (MPD):(HD), obtained as "KURARAY POLYOL C-3090" from Kuraray Co. Ltd. |
| C-590 | A polycarbonate diol of about 500 MW made with about a 9:1 mole ratio of (MPD):(HD) obtained as "KURARAY POLYOL C-590" from Kuraray Co. Ltd. |
| CEA | 2-Carboxyethyl acrylate, obtained from Sigma-Aldrich, St. Louis, MO. |
| Chloroform | Obtained from EMD Millipore, a part of Merck KGaA, Darmstadt, Germany. |
| CHMA | Cyclohexyl methacrylate, obtained from Alfa Aesar, Haverhill, MA. |
| DBTDL | Dibutyltin diacrylate, obtained from Sigma-Aldrich, St. Louis, MO. |
| DDDMA | 1,12-dodecanediol dimethacrylate obtained as "SR262" from Sartomer, Exton, PA. |
| Desmodur I (IPDI) | Isophorone diisocyanate, under trade designation "DESMODUR I" equivalent weight 111.11, molecular weight 222.22 g/mole, from Covestro LLC. |

-continued

Materials Table

| Material designation | Description |
| --- | --- |
| Desmodur W (H12MDI) | Hydrogenated methylene diisocyanate, under trade designation "DESMODUR W", equivalent weight 131.25, molecular weight 262.5 g/mole, from Covestro LLC. |
| DiCPMA | Dicyclopentanyl methacrylate Obtained from TCI America, Portland, OR. |
| DMAP | 4-dimethylaminopyridine, obtained from Alfa Aesar, Haverhill, MA. |
| EHMA | 2-Ethyl hexyl methacrylate, obtained from Alfa Aesar. |
| Ethanol | Obtained from Spectrum Chemicals, New Brunswick, NJ. |
| Ethanolamine | Obtained from Sigma Aldrich. |
| Ethyl acetate | Obtained from EMD Millipore, a part of Merck KGaA. |
| Exothane-10 | A urethane (meth)acrylate oligomer comprising a polyethylene oxide diol of about 400 MW, obtained as "EXOTHANE-10" from Esstech Inc., Essington, PA. |
| Exothane-108 | A urethane (meth)acrylate oligomer comprising a polytetramethylene oxide diol of about 650 MW, obtained as "EXOTHANE-108" from Esstech Inc. |
| G-AC-MAC | Glycerol acrylate methacrylate (1-(acryloyloxy)-3-(methacryloyloxy)-2-propanol, CAS 1709-71-3), obtained from TCI America, Portland, OR. |
| HCl | Hydrochloric acid, obtained from Sigma Aldrich. |
| HDDMA | 1,6-Hexanediol dimethacrylate (SR239), obtained from Sartomer. |
| HDI | 1,6-diisocyanatohexane, equivalent weight 84.1, molecular weight 168.2, available under trade designation "DESMODUR H", from Covestro LLC. |
| HEA | Hydroxyethyl acrylate, obtained from Alfa Aesar. |
| HEMA | Hydroxyethyl methacrylate, obtained from TCI America, Portland, OR. |
| Heptane | Heptane (Ultra resi-analyzed) was obtained from Avantor, Center Valley, PA. |
| Hydroquinone | Obtained from Alfa Aesar. |
| IBOA | Isobornyl acrylate, obtained from Alfa Aesar. |
| IBOMA | Isobornyl methacrylate obtained as "SR423A" from Sartomer. |
| IEM | Isocyanatoethyl methacrylate, MW 155.15, available under the trade designation "KARENZ MOI," from Showa Denko. |
| IEM-EO | Isocyanatoethoxyethyl methacrylate, MW 199.2, available under the trade designation "KARENZ MOI-EG," from Showa Denko. |
| iPrOH | Isopropyl alcohol, obtained from EMD Millipore, a part of Merck KGaA. |
| KOH | Potassium hydroxide, obtained from Sigma Aldrich. |
| MDI | Product trade designation "MONDUR MLQ," an approximate 80:20 mixture of 4,4' and 2,4' diphenylmethane diisocyanate, equivalent weight 125.125, molecular weight 250.25, from Covestro LLC. |
| MeOH | Methanol, obtained from EMD Millipore, a part of Merck KGaA. |
| Methacrylic acid | Obtained from Sigma Aldrich. |
| Methacrylic anhydride | Obtained from Sigma Aldrich. |
| $Na_2CO_3$ | Sodium Carbonate, obtained from Sigma Aldrich. |
| NL2030B | A polycarbonate diol of about 2000 MW made with about a 3:7 mole ratio of neopentyl glycol:butane diol, obtained as "NL2030B" from Mitsubishi Chemical Company, Tokyo, JP. |
| NL2005B | A polycarbonate diol of about 2000 MW made with about a 5:95 mole ratio of neopentyl glycol:butane diol, obtained as "NL2005B" from Mitsubishi Chemical Company. |
| NL2010DB | A polycarbonate diol of about 2000 MW made with about a 10:90 mole ratio of 1,10-decane diol:butane diol, obtained as "NL2010B" from Mitsubishi Chemical Company. |
| NVP | 1-vinyl-2-pyrolidone, obtained from TCI Chemicals, Portland, OR. |
| Omnirad 379 | 2-Dimethylamino-2-(4-methyl-benzyl)-1-(4-morpholin-4-yl-phenyl)-butan-1-one, photoinitiator, obtained from IGM Resins, Charlotte, NC. |
| P-1020 | A 3-methyl-1,5-pentane diol terephthalate diol of about 1000 MW obtained as "KURARAY POLYOL P-1020" from Kuraray. |
| PBS | Phosphate buffered saline (PBS, 10X), pH = 7.4, obtained from Alfa Aesar. |
| PEG600DMA | Polyethylene glycol 600 dimethacrylate, obtained from Sartomer. |
| PEMA | 2-Phenoxy ethyl methacrylate ("SR340"), obtained from Sartomer. |
| Petroleum ether | Obtained from EMD Millipore, a part of Merck KGaA. |
| Phenothiazine | Obtained from TCI America. |
| Propylene Carbonate | Obtained from Alfa Aesar. |
| PTMO-2000 | A poly(tetramethylene oxide) diol of about 2000 MW, obtained as "POLYTHF 1000" polyether from BASF, Florham Park, NJ. |

Materials Table

| Material designation | Description |
|---|---|
| p-toluenesulfonic acid | Obtained from TCI, America. |
| Sodium bicarbonate | Obtained from EMD Millipore, a part of Merck KGaA. |
| Sulfuric acid | Obtained from EMD Millipore, a part of Merck KGaA. |
| Tetrahydrofuran | Omnisolv HPLC grade from EMD Millipore, a part of Merck KGaA. |
| THFMA | Tetrahydrofurfuryl methacrylate, obtained from Sartomer. |
| Tinuvin 326 | Phenol, 2-(5-chloro-2H-benzotriazol-2-yl)-6-(1,1-dimethylethyl)-4-methyl, UV-absorber, obtained from BASF. |
| TMXDI | 1,3-Bis(1-isocyanato-1-methylethyl)benzene, equivalent weight 122.15, molecular weight 244.3, from Sigma-Aldrich. |
| TPO | 2,4,6-trimethylbenzoyldiphenylphosphine oxide photoinitiator obtained as "IRGACURE TPO" from BASF. |
| Triethylamine | Obtained from EMD Millipore, a part of Merck KGaA. |
| TMCHMA | 3,3,5-trimethylcylohexanemethacrylate, obtained from Sartomer. |
| XK-672 | Zn based catalyst obtained as "K-KAT XK-672" from King Industries, Norwalk, CT. |

Preparatory Examples

Preparation of Naphthalimide Acrylate (NapA)

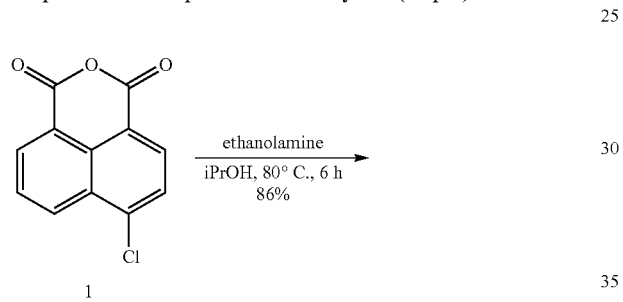

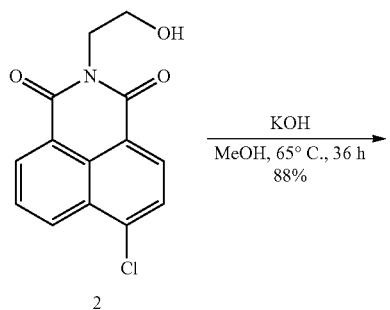

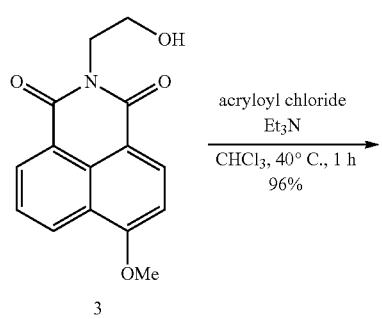

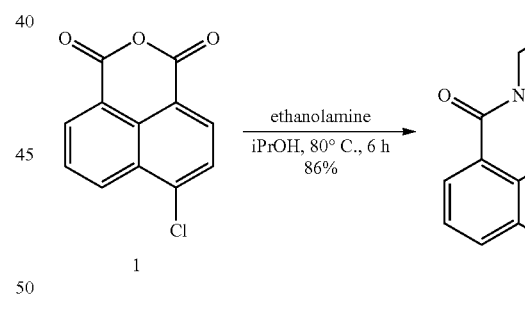

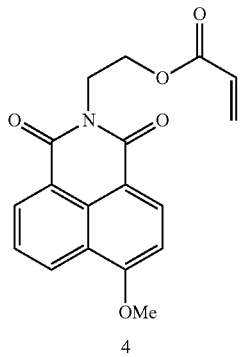

To a 1 L three-neck round-bottom flask was added 4-chloronaphthalic anhydride (100.0 g, 0.4299 moles, 1.0 equiv.), ethanolamine (26.26 g, 0.4299 moles, 1.0 equiv.), and iPrOH (516.7 g). The flask was outfitted with a temperature probe, overhead stirrer, and reflux condenser. The reaction mixture was heated to 80° C. with stirring for 6 hours, then cooled to 10° C. with an ice bath. The resulting yellow solid was collected via filtration and stirred with a mixture of water (300 g), iPrOH (300 g), and concentrated HCl (10 g). The resulting solid was filtered and washed with water/iPrOH (1:1, 500 g) and allowed to air dry. This afforded alcohol 2 (102 g, 86%).

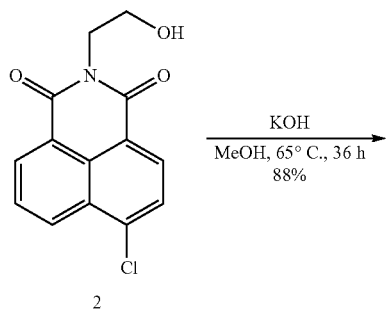

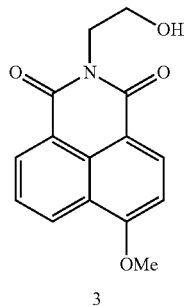

To a 2 L three-neck round-bottom flask was added alcohol 2 (100.0 g, 0.3627 moles, 1.0 equiv.), KOH (40.71 g, 0.7255 moles, 2.0 equiv.), and methanol (581 g). The flask was outfitted with a temperature probe, overhead stirrer, and reflux condenser. The reaction mixture was heated to 65° C. with stirring for 36 hours, then cooled to 10° C. with an ice bath. The resulting yellow solid was collected via filtration and stirred with a mixture of water (300 g), MeOH (300 g), and concentrated HCl (10 g). The resulting solid was filtered and washed with water/MeOH (1:1, 600 g) and allowed to air dry. This afforded alcohol 3 (86.5 g, 88%).

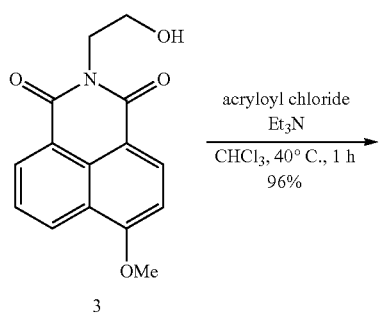

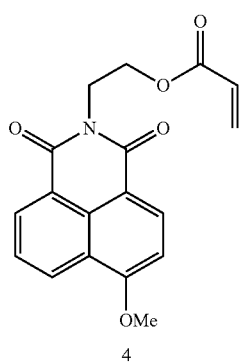

To a 1 L 3-neck round-bottom flask was added alcohol 3 (80.00 g, 0.2949 moles, 1.0 equiv.), chloroform (704 g), and triethylamine (35.81 g, 0.3539 moles, 1.2 equiv.). The flask was outfitted with a Claisen adapter, overhead stirrer, and a pressure-equalizing addition funnel. The Claisen adapter was outfitted with a temperature probe and a reflux condenser. The reaction mixture was stirred and heated to 40° C. Acryloyl chloride (29.36 g, 0.3244 moles, 1.1 equiv.) was added dropwise via the addition funnel such that the reaction temperature did not rise above 45° C. After addition was complete, the reaction was stirred for 30 minutes. Triethylamine (6.00 g, 0.0593 moles, 0.2 equiv.) was added, followed by acryloyl chloride (5.00 g, 0.0552 moles, 0.19 equiv.) dropwise. The reaction was stirred for an additional 30 minutes at 40° C. Next, the reaction flask was outfitted with a distillation head, condenser, and receiving flask. The reaction mixture was heated to strip most of the chloroform. EtOH (500 g) was added, and the strip continued until the distillation head temperature reached 78° C. The reaction mixture was cooled to 10° C. with an ice bath and filtered. The resulting solid was washed with water/HCl (10:1, 500 mL), water/$Na_2CO_3$ (10:1, 500 mL), and water/EtOH (1:1, 500 mL). The solid was allowed to dry to afford the product 4 as a pale yellow solid (92.5 g, 96%).

Preparation of Adamantyl-1-Methacrylate (AdMA)

A 2 L, 3 neck round-bottom flask was fitted with a dean-stark trap with a condenser, magnetic stir bar, and a thermometer. 1-Adamantanol (252 g 1.650 mol), hydroquinone (0.3 g), methacrylic acid (455 g, 5.28 mmol), and methylcyclohexane (400 g) were added and the mixture was stirred. Sulfuric acid (10.5 g) was then added to the mixture, and then dry air was slowly bubbled into the mixture. The mixture was heated to reflux under constant bubbling of air for 26 hours, during which time the reaction product water was removed using the trap. The mixture was then cooled to room temperature, and slowly added to a mechanically stirred, ice-bath cooled mixture of 350 g KOH (6.2 mol) in 1000 g of deionized water and 500 g hexanes. After the addition was complete, the resulting mixture was separated using a separatory funnel, and extracted 1×500 mL hexanes. The combined organic extracts were washed with a saturated aqueous sodium bicarbonate solution, and then 20 mg of phenothiazine was added to the organic phase. This was then dried over anhydrous magnesium sulfate, filtered, and concentrated by rotary evaporation. The concentrate was then distilled under vacuum (BP=87-90° C., 0.3 torr), where the receiver flask contained 15 mg of 4-hydroxy-TEMPO, and 320 g of liquid was obtained. BHT (48 mg) was then added and dry air was bubbled into the clear product for 30 seconds before storage. $^1$H NMR: 5.99 (m, 1H), 5.45 (m, 1H), 2.14 (m, 9H), 1.87 (m, 3H), 1.64 (m, 6H). $^{13}$C NMR: 168.5, 138.1, 124.3, 80.4, 41.3, 36.3, 30.9, 18.4. Purity by GC=98.4%.

Characterization of the Above Material by Nuclear Magnetic Resonance (NMR) Spectroscopy An Ultrashield 500 Plus FT NMR instrument from Bruker (Billerica, Mass.) was used to acquire $^1$H NMR (500 MHz) and $^{13}$C NMR (125 MHz) spectra. Chemical shifts (δ) are reported in ppm relative to $CDCl_3$. Abbreviations for splitting patterns are as follows; s (singlet); d (doublet); t (triplet); q (quartet); m (multiplet); br (broad); app (apparent) and combinations of these abbreviations.

Preparation of 4-Tert-Butylcyclohexyl Methacrylate (Mixture Cis/Trans) (tBuCHMA)

A 2 L, 3 neck round-bottom flask was fitted with a 250 mL addition funnel, magnetic stir bar, and a thermometer. 4-ter-tbutylcyclohexanol (150 g, 960 mmol), dichloromethane (600 g), triethylamine (178 g, 1760 mmol), and DMAP (6.4 g, 52 mmol) were added to the flask, and then methacrylic anhydride (263 g, 1710 mmol) was added dropwise keeping the temperature below 35° C. This mixture was stirred at room temperature for 24 hours, and then 150 mL water was added and stirred overnight. Dichloromethane (500 g) was then added, and the organic phase was washed with 200 mL water, 200 mL of 0.1 M HCl, and 200 mL saturated sodium bicarbonate. The organic phase was dried over anhydrous magnesium sulfate and 20 mg phenothiazine was added. This was filtered and concentrated by rotary evaporation. The concentrate was then distilled under vacuum (BP=73-90° C., 0.3 torr), where the receiver flask contained 7 mg of 4-hydroxy-TEMPO, and 170 g of liquid was obtained. BHT (26 mg) was then added and dry air was bubbled into the clear product for 30 seconds before storage. $^1$H NMR was consistent with a mixture of 72% trans and 28% cis isomer as described in Macromolecules, 1993, 26, 1659-1665. GC analysis showed a total of 96% of the two isomers with a ratio of 73% trans/27% cis.

Characterization of the Above Material by Gas Chromatography (GC)

Sample purity and product ratios were determined by gas chromatography (GC) and was performed using a Hewlett Packard (Palo Alto, Calif.) 6890 Series Plus gas chromatograph with a flame ionization detector and HP G1530A digital integrator. Sample injection was done with a 7683 series injector in conjunction with an injection volume of 2 microliters, injection port at a temperature of 250° C., and a split ratio of 20:1. A 30 m×0.53 mm×5 micrometer column obtained under the trade designation "RESTEX RTX-1" from Restek Corp. (Bellefonte, Pa.) was utilized with a flow rate of 12.4 mL/min He as the carrier gas with a temperature program of 50° C. to 230° C. at 15° C./min; 230° C. to 280° C. at 50° C./min; then hold at 280° C. for 2 min.

Preparation of Diol Diacrylates

Preparation of C-590 Diol Diacrylate

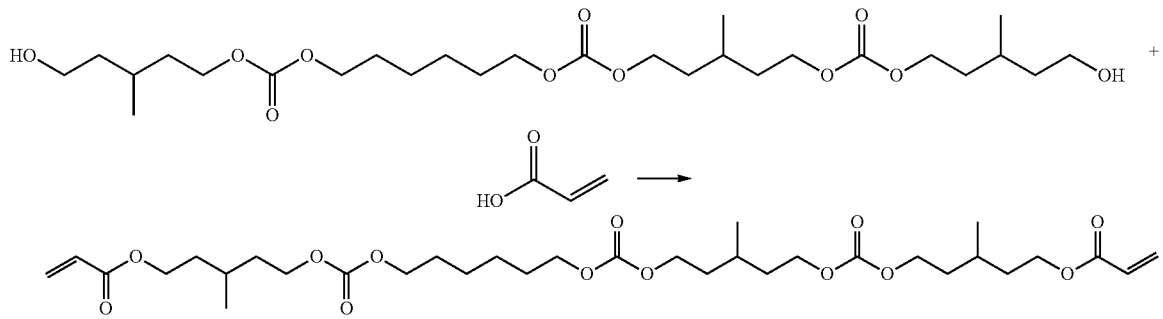

C-590 diol (50 g, 90.79 mmol) and acrylic acid (19.8 g, 275 mmol) and p-toluenesulfonic acid (1.96 g, 11.3 mmol) were charged into a 250 mL 3-neck flask equipped with a magnetic stirring bar, a thermocouple and a condenser. The mixture was heated at 85° C. Vacuum (15-20 torr) was applied for 2 minutes every 15-20 minutes in order to remove any formed water from the reaction. This was repeated for 4 hours at which time there were no signs of H$_2$O forming or condensing on the flask walls. The heat was turned off. After cooling to room temperature, the mixture was dissolved in a 130 mL ethyl acetate/petroleum ether mixture (10:3 ratio). The mixture was extracted with 10% aqueous NaOH (100 mL) then H$_2$O (200 mL). The organic layer was dried (over Na$_2$SO$_4$), then concentrated to give a clear liquid with 91% yield.

Preparation of C-590 Diol Dimethacrylate (C-590 Diol MA)

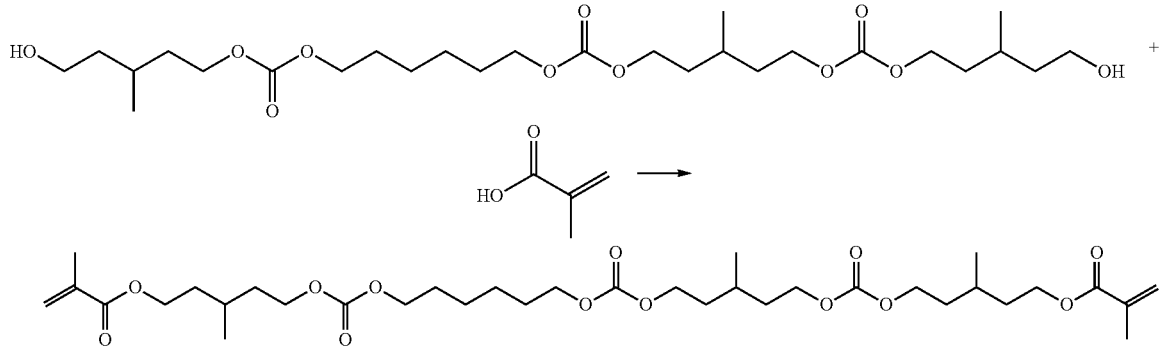

This material was prepared following the procedure described above for preparation of C-590 diol diacrylate, except that methacrylic acid was used instead of acrylic acid. The product was isolated as a low viscosity liquid in 88-93% yield.

Preparation of C-2050 Diol Dimethacrylate (C-2050 Diol MA)

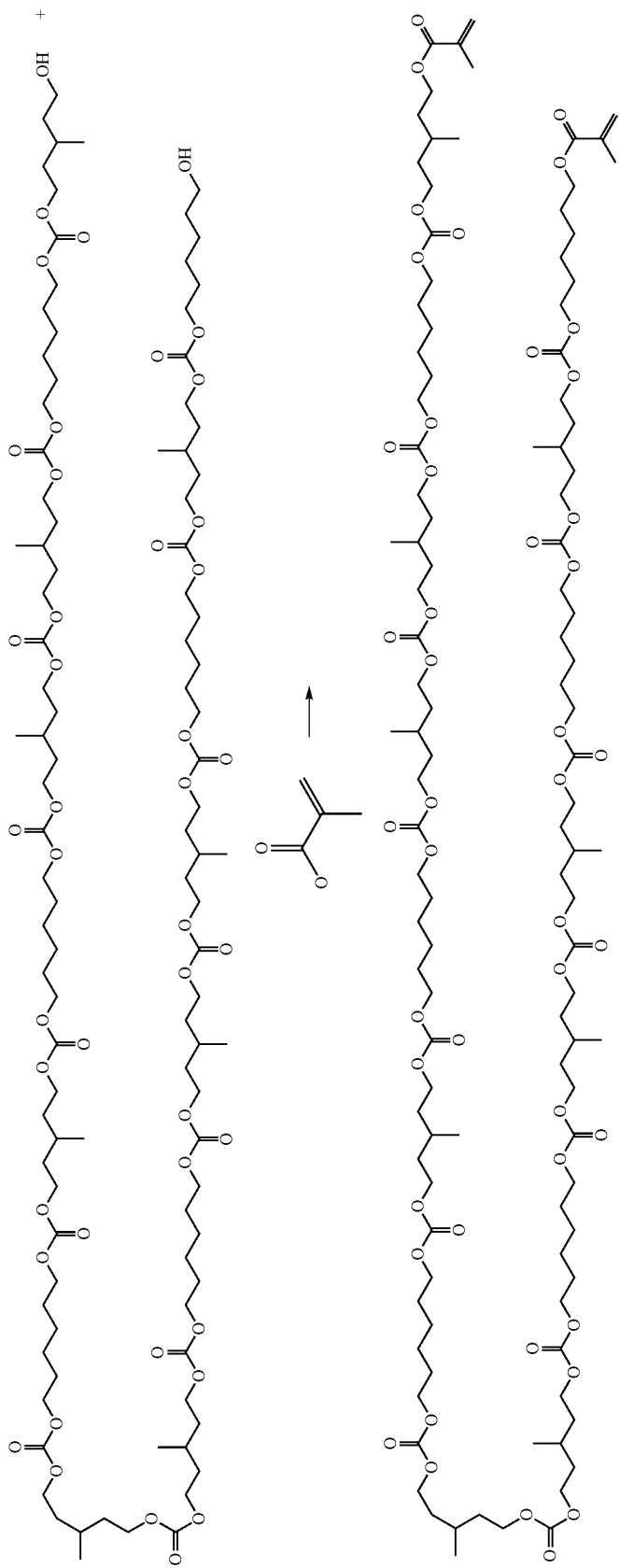

This material was prepared following the procedure described above for preparation of C-590 diol diacrylate, except that methacrylic acid was used instead of acrylic acid and C-2050 diol was used instead of C-590 diol.

Preparation of Polycarbonate Diol Based Urethane (Meth) acrylates

The urethane acrylates are of three main types:

1) Polycarbonate diols reacted with diisocyanates capped with (meth)acrylate mono-ols such as HEA and HEMA. Below is an idealized structure of such a material, illustrated with a hexane diol based polycarbonate diol:

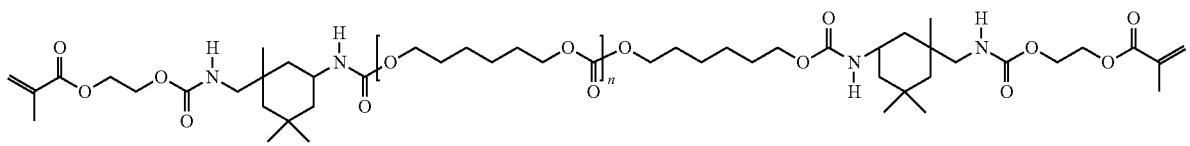

2) Polycarbonate diols capped with isocyanate-(meth)acrylates, illustrated with a hexane diol based polycarbonate diol and IEM:

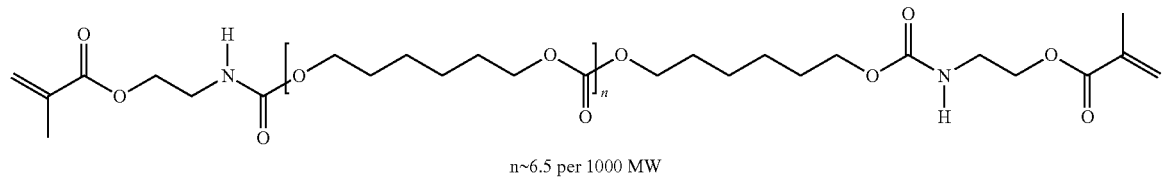

n~6.5 per 1000 MW

3) Diisocyanates capped with (meth)acrylate mono-ols:

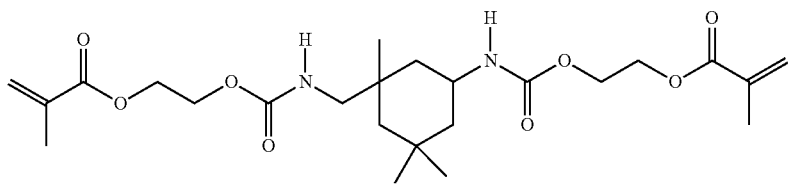 [SMILES: C=C(C)C(=O)OCCOC(=O)NCC1(C)CC(NC(=O)OCCOC(=O)C(=C)C)CC(C)(C)C1]

Type 1: 4 IPDI/2 C-2050/2 HEMA (PE-1)

A 1 L three-necked round-bottom flask was charged with 514.75 g C-2050 (0.52285 eq, 984.5 hydroxide equivalent weight (OH EW)), heated to about 45° C., then were added 116.19 g IPDI (1.0457 eq), 0.280 g BHT (400 ppm), and 0.175 DBTDL (250 ppm). The reaction was heated under dry air to an internal setpoint of 105° C. (temperature reached at about 20 min). At 1 hour and 20 minutes 69.06 g HEMA (0.5307 eq, 130.14 MW, a 1.5% excess) was added via an addition funnel at a steady rate over 1 hour and 10 minutes. The reaction was heated for about 2.5 hours at 105° C., then an aliquot was checked by Fourier transform infrared spectroscopy (FTIR) and found to have no —NCO peak at 2265 cm$^1$ and the product was isolated as a clear, viscous material.

Type 2: C-2050/2 IEM (PE-2)

A 1 L three-necked round-bottom flask was charged with 431.93 g C-2050 (0.43873 eq, 984.5 OH EW), 0.200 g BHT (400 ppm), and 0.125 g DBTDL (250 ppm) and heated to an internal temperature of about 60° C. under dry air. Then 68.07 g IEM (0.43873 eq, 155.15 MW) was added via an addition funnel over about 1 hour and 20 minutes. At 1 hour and 30 minutes an aliquot was checked by FTIR and found to have no —NCO peak at 2265 cm$^{-1}$. At 1 hour and 38 minutes 1.32 g more IEM was added, and an aliquot was checked by FTIR and found to have no —NCO peak at 2265 cm$^{-1}$. At 4 hours into the reaction, the reaction was stopped and the product was isolated as a clear, viscous material.

Type 3: IPDI/HEMA (PE-3)

A 1 L three-necked round-bottom flask was charged with 319.80 g IPDI (2.878 eq), 0.280 g BHT, and 0.175 g bismuth neodecanoate (250 ppm based on solids) and heated to an internal temperature of about 55° C. under dry air. Then 380.20 g (2.921 eq) HEMA was added over 1 hour and 45 minutes, with the internal temperature rising to a maximum of 90° C. At 2 hours and 25 minutes an aliquot was checked by FTIR and found to have no —NCO peak at 2265 cm$^{-1}$. The samples in Table 2 below were prepared by methods according to those of Types 1-3 described above, using the amounts and types of materials indicated in the table.

TABLE 2

Preparative Examples of Polycarbonate Diol Based Polyurethane (Meth) Acrylates

| Sample | Designation | Isocyanate Type | g | Diol Type | g | OH EW | (meth)-acrylate mono-ol Type | g | Catalyst Type | g | BHT g |
|---|---|---|---|---|---|---|---|---|---|---|---|
| PE-4 | 4 IPDI/2 P-1020/2 HEMA | IPDI | 39.02 | P-1020 | 87.79 | 500 | HEMA | 23.19 | DBTDL | 0.075 | 0 |
| PE-5 | 4 IPDI/2 C-2050/2 HEMA | IPDI | 82.99 | C-2050 | 367.68 | 984.2 | HEMA | 49.33 | DBTDL | 0.125 | 0.200 |
| PE-6 | 4 H12MDI/2 C-2050/2 HEMA | H12MDI | 95.17 | C-1090 | 356.94 | 984.2 | HEMA | 47.89 | DBTDL | 0.125 | 0.200 |
| PE-7 | 4 IPDI/2 C-2050/2 HEMA | IPDI | 82.99 | C-2050 | 367.68 | 984.2 | HEMA | 49.33 | DBTDL | 0.125 | 0.200 |
| PE-8 | 4 IPDI/2 C-2020/2 HEMA | IPDI | 83.81 | C-2020 | 366.37 | 971.42 | HEMA | 49.82 | DBTDL | 0.125 | 0.200 |
| PE-9 | C-2090/IEM | IEM | 69.63 | C-2090 | 430.37 | 959 | — | | DBTDL | 0.125 | 0.200 |
| PE-10 | C-2090/IEM-EO | IEM-EO | 86.00 | C-2050 | 414.00 | 959 | — | | DBTDL | 0.125 | 0.200 |
| PE-11 | C-2050/IEM | IEM | 18.91 | C-2050 | 120.00 | 984.2 | — | | DBTDL | 0.035 | 0.056 |
| PE-12 | C-2200/IEM | IEM | 68.86 | C-2200 | 431.14 | 971.42 | — | | DBTDL | 0.125 | 0.200 |
| PE-13 | 4 IPDI/2 C-3090/2 HEMA | IPDI | 60.57 | C-3090 | 403.43 | 1480.21 | HEMA | 36.00 | DBTDL | 0.125 | 0.200 |
| PE-14 | C-3090/IEM | IEM | 47.44 | C-3090 | 452.56 | 1480.21 | — | — | DBTDL | 0.125 | 0.200 |
| PE-15 | C-1090/IEM | IEM | 117.78 | C-1090 | 382.22 | 503.5 | — | — | DBTDL | 0.125 | 0.200 |
| PE-16 | C-590/IEM | IEM | 192.83 | C-590 | 307.17 | 247.14 | — | — | DBTDL | 0.125 | 0.200 |
| PE-17 | 4 IPDI/2 212-20/2 HEMA | IPDI | 98.96 | 212-20 | 342.22 | 768.49 | HEMA | 58.82 | DBTDL | 0.125 | 0.200 |
| PE-18 | 4 IPDI/2 PTMO-2000/2 HEMA | IPDI | 82.82 | PTMO-2000 | 367.95 | 997.0 | HEMA | 49.23 | DBTDL | 0.125 | 0.200 |
| PE-19 | 4 IPDI/1.5 C-2050/2.5 HEMA | IPDI | 98.70 | C-2050 | 327.96 | 984.2 | HEMA | 73.34 | DBTDL | 0.125 | 0.200 |
| PE-20 | 4 IPDI/2.5 C-2050/1.5 HEMA | IPDI | 71.6 | C-2050 | 396.49 | 984.2 | HEMA | 31.92 | DBTDL | 0.125 | 0.200 |
| PE-21 | 4 TMXDI/2 C-2050/2 HEMA | TMXDI | 89.78 | C-2050 | 361.68 | 984.2 | HEMA | 48.54 | DBTDL | 0.125 | 0.200 |
| PE-22 | 4 IPDI/2 C-2050/2 HEA | IPDI | 117.46 | C-2050 | 520.24 | 984.2 | HEA | 62.3 | DBTDL | 0.125 | 0.200 |
| PE-23 | 4 HDI/2 C-2050/2 HEMA | HDI | 65.47 | C-2050 | 383.11 | 984.2 | HEMA | 51.42 | DBTDL | 0.125 | 0.200 |
| PE-24 | 4 MDI/2 C-2050/2 HEMA | MDI | 91.56 | C-2050 | 360.11 | 984.2 | HEMA | 48.33 | DBTDL | 0.125 | 0.200 |
| PE-25 | 4 IPDI/2 C-1090/2 HEMA | IPDI | 131.81 | C-1090 | 289.85 | 488.67 | HEMA | 78.35 | DBTDL | 0.125 | 0.200 |
| PE-26 | 4 IPDI/2 C-2015N/2 HEMA | IPDI | 83.44 | C-2015N | 366.97 | 977.35 | HEMA | 49.60 | DBTDL | 0.125 | 0.200 |
| PE-27 | 4 IPDI/2 C-2050/2 HEMA | IPDI | 117.46 | C-2050 | 520.24 | 984.2 | HEMA | 69.82 | BiN | 0.177 | 0.283 |
| PE-28 | 4 IPDI/2 XP C2613/2 HEMA | IPDI | 82.91 | XP C2613 | 373.11 | 1000 | HEMA | 49.29 | DBTDL | 0.125 | 0.200 |
| PE-29 | 4 IPDI/2 C 7203/2 HEMA | IPDI | 81.08 | C 7203 | 370.73 | 1016.12 | HEMA | 48.19 | DBTDL | 0.125 | 0.200 |
| PE-30 | 4 IPDI/1.5 C-3090/2.5 HEMA | IPDI | 74.20 | C-3090 | 370.67 | 1480.21 | HEMA | 55.13 | DBTDL | 0.125 | 0.200 |
| PE-31 | 4 IPDI/1 C-3090/3 HEMA | IPDI | 95.75 | C-3090 | 318.88 | 1480.21 | HEMA | 85.37 | DBTDL | 0.125 | 0.200 |
| PE-32 | 4 IPDI/2 C-2050/2 HEMA | IPDI | 265.57 | C-2050 | 1176.6 | 984.2 | HEMA | 157.86 | BiN | 0.400 | 0.640 |
| PE-33 | IPDI/HEMA | IPDI | 319.8 | — | — | — | HEMA | 380.20 | BiN | 0.175 | 0.280 |
| PE-34 | 4 IPDI/2 C-2050/2 HEMA | IPDI | 83.01 | C-2050 | 367.65 | 984.2 | HEMA | 49.34 | XK-672 | 0.125 | 0.200 |
| PE-35 | 4 IPDI/2 C-2050/2 HEMA | IPDI | 83.01 | C-2050 | 367.65 | 984.2 | HEMA | 49.34 | XK-672 | 0.125 | 0.200 |
| PE-36 | 4 IPDI/2 C-2050/2 HEMA | IPDI | 83.01 | C-2050 | 367.65 | 984.2 | HEMA | 49.34 | XK-672 | 0.125 | 0.200 |
| PE-37 | 4 IPDI/2 C-2090/2 HEMA | IPDI | 125.16 | C-2090 | 550.45 | 977.35 | HEMA | 74.40 | XK-672 | 0.125 | 0.200 |
| PE-38 | 4 IPDI/2 C-3090/2 HEMA | IPDI | 90.85 | C-3090 | 605.15 | 1480.21 | HEMA | 54.00 | XK-672 | 0.125 | 0.200 |
| PE-39 | 4 IPDI/2.5 C-2090/1.5 HEMA | IPDI | 108.02 | C-2090 | 593.83 | 977.35 | HEMA | 48.15 | XK-672 | 0.125 | 0.200 |
| PE-40 | 4 IPDI/3 C-2090/1 HEMA | IPDI | 95.00 | C-2090 | 626.76 | 977.35 | HEMA | 28.24 | XK-672 | 0.125 | 0.200 |
| PE-41 | 4 IPDI/2 C-1090/2 HEMA | IPDI | 117.78 | C-1090 | 262.21 | 494.71 | HEMA | 70.01 | XK-672 | 0.113 | 0.180 |
| PE-42 | 4 IPDI/2.5 C-1090/1.5 HEMA | IPDI | 106.42 | C-1090 | 296.14 | 494.71 | HEMA | 47.44 | XK-672 | 0.113 | 0.180 |
| PE-43 | 4 IPDI/3 C-1090/1 HEMA | IPDI | 97.06 | C-1090 | 324.10 | 494.71 | HEMA | 28.85 | XK-672 | 0.113 | 0.180 |
| PE-44 | 4 IPDI/2 C-2050/2 HEMA | IPDI | 248.55 | C-2050 | 1100.80 | 984.2 | HEMA | 150.65 | XK-672 | 0.375 | 0.600 |
| PE-45 | 4 IPDI/2 NL2030B/2 HEMA | IPDI | 97.35 | NL2030B | 442.80 | 1010.8 | HEMA | 59.86 | XK-672 | 0.15 | 0.240 |
| PE-46 | 4 IPDI/2 NL2005B/2 HEMA | IPDI | 95.91 | NL2005B | 445.11 | 1031.25 | HEMA | 58.98 | XK-672 | 0.15 | 0.240 |
| PE-47 | 4 IPDI/2 NL2010DB/2 HEMA | IPDI | 98.25 | NL2010DB | 441.34 | 998.22 | HEMA | 60.41 | XK-672 | 0.15 | 0.240 |
| PE-48 | H12MDI/HEMA | H12MDI | 310.25 | | | | HEMA | 324.73 | XK-672 | 0.159 | 0.254 |
| PE-49 | 4 IPDI/2 C-3090/ 1 HEMA/1 G-AC-MAC | IPDI | 71.35 | C-3090 | 470.32 | 1464.75 | HEMA/G-AC-MAC | 22.04/36.28 | XK-672 | 0.159 | 0.254 |
| PE-50 | 4 IPDI/2 C-3090/2 G-AC-MAC | IPDI | 69.70 | C-3090 | 459.42 | 1467.75 | G-AC-MAC | 72.49 | XK-672 | 0.159 | 0.254 |

* add diol over 1.5 h

Determination of HEMA-IPDI-HEMA Oligomer Concentration.

Determination of a concentration of HEMA-IPDI-HEMA oligomer was performed by liquid chromatography-mass spectrometry (LC/MS) on an Agilent 1260 Infinity Series liquid chromatography system (Agilent Technologies, Waldbronn, Germany) using an Agilent Poroshell 120 SB-C8 2.1 mm×50 mm 2.7 micrometer column eluted at 40° C. with a flow rate of 0.5 mL per minute. 2 microliter samples were injected and eluted with a linear gradient as described below. The water was Omnisolv HPLC grade from EMD Millipore, a part of Merck KGaA. The re-equilibration time between experiments was 5 minutes. Detection was with an Agilent 6130 Quadrupole LC/MS detector with electrospray ionization. Sample quantification was done by integration of the chromatographic peak detected at 500.3 m/z (M-NH$_4^+$).

Mass spectrometer parameters were in atmospheric pressure ionization-electrospray (API-ES) mode: capillary voltage 4 kV, nebulizer gas pressure 50 psig (345 kPa gauge), drying gas flow rate 10 liters per minute, drying gas temperature 300° C.

TABLE 3

Solvent elution gradient

| Solvent | Time (min) |
|---|---|
| 6 mM ammonium formate in water | 0 |
| 6 mM ammonium formate in 98% acetonitrile/2% water | 3 |
| 6 mM ammonium formate in 98% acetonitrile/2% water | 5 |
| 89% acetonitrile 10% tetrahydrofuran 1% formic acid | 6 |

TABLE 3-continued

| Solvent elution gradient | |
|---|---|
| Solvent | Time (min) |
| 89% acetonitrile 10% tetrahydrofuran 1% formic acid | 8 |
| 6 mM ammonium formate in water | 9 |

Calibration samples were prepared by dissolution of 0.1009 g of material polyurethane acrylate PE-33 in a 100 mL volumetric flask using ethyl acetate. This solution was then diluted 1 mL into a 100 mL volumetric flask using acetonitrile to produce dilution 1. Dilution 1 was further diluted to ~2.02, 0.505, 0.101 and 0.0121 ppm concentrations in acetonitrile and filtered through 0.22 micron PTFE syringe filters (Fisher Brand, Thermo Fisher Scientific, Hampton, N.H.). The calibration curve was linear from 2.02-0.0121 ppm. Calibrations were performed directly preceding analytical samples.

Analytical samples were prepared by dissolution of 0.1-0.3 g of material in a 100 mL volumetric flask using ethyl acetate. This solution was then diluted 1 mL into a 100 mL volumetric flask using acetonitrile to produce dilution 1. Dilution 1 was filtered through 0.22 micron PTFE syringe filters (Fisher Brand) and analyzed as discussed above. The results for each sample are shown in Table 4 below.

TABLE 4

| Sample | Polyol | Catalyst | IPDI:Polyol:HEMA eq ratio | % HEMA-IDPI-HEMA in polymer (does not include IBOMA diluent if present) |
|---|---|---|---|---|
| PE-13 | C-3090 | DBTDL | 4:2:2 | 5.0% |
| PE-30 | C-3090 | DBTDL | 4:1.5:2.5 | 11.1% |
| PE-31 | C-3090 | DBTDL | 4:1:3 | 20.7% |
| PE-37 | C-2090 | XK-672 | 4:2:2 | 5.4% |
| PE-38 | C-3090 | XK-672 | 4:2:2 | 3.8% |
| PE-7 | C-2050 | DBTDL | 4:2:2 | 5.6% |
| PE-9 | C-2050 | DBTDL | 4:2:2 | 5.5% |
| PE-32 | C-2050 | BiN | 4:2:2 | 5.7% |
| PE-25 | C-1090 | DBTDL | 4:2:2 | 8.6% |
| PE-39 | C-2090 | XK-672 | 4:2.5:1.5 | 3.0% |
| PE-40 | C-2090 | XK-672 | 4:3:1 | 0.3% |
| PE-41 | C-1090 | XK-672 | 4:2:2 | 7.5% |
| PE-42 | C-1090 | XK-672 | 4:2.5:1.5 | 1.8% |
| PE-43 | C-1090 | XK-672 | 4:3:1 | 0.1% |
| PE-44 | C-2050 | XK-672 | 4:2:2 | 5.0% |

General Procedure for Formulation Preparation

Formulations were prepared by weighing the components (indicated in Tables 5-17) in an amber jar, followed by rolling on a roller (having the trade designation "OLDE MIDWAY PRO18" and manufactured by Olde Midway) at 60° C. until mixed.

TABLE 5

Example formulations (amounts in parts by weight)

| Component | EX-1 | EX-2 | EX-3 | EX-4 | EX-5 | EX-6 |
|---|---|---|---|---|---|---|
| PE-41 | 50 | | | | | |
| PE-42 | | 50 | | | | |
| PE-43 | | | 50 | | | |
| PE-37 | | | | 50 | | |
| PE-39 | | | | | 50 | |
| PE-40 | | | | | | 50 |
| IBOMA | 50 | 50 | 50 | 50 | 50 | 50 |
| TPO | 2 | 2 | 2 | 2 | 2 | 2 |

TABLE 6

Example formulations (amounts in parts by weight)

| Component | EX-7 | EX-8 | EX-9 | EX-10 | EX-11 | EX-12 | EX-13 | EX-14 |
|---|---|---|---|---|---|---|---|---|
| PE-19 | 50 | | | | | | | |
| PE-7 | | 50 | | | | | | |
| PE-22 | | | 50 | | | | | |
| PE-20 | | | | 50 | | | | |
| PE-21 | | | | | 50 | | | |
| PE-23 | | | | | | 50 | | |
| PE-24 | | | | | | | 50 | |
| PE-6 | | | | | | | | 50 |
| IBOMA | 50 | 50 | 50 | 50 | 50 | 50 | 50 | 50 |
| TPO | 2 | 2 | 2 | 2 | 2 | 2 | 2 | 2 |
| BHT | | 0.025 | | | | | | |

TABLE 7

Example formulations (amounts in parts by weight)

| Component | EX-15 | EX-16 | EX-17 | EX-18 | EX-19 |
|---|---|---|---|---|---|
| PE-38 | 50 | | | | |
| PE-31 | | 50 | | | |
| PE-26 | | | 50 | | |
| PE-8 | | | | 50 | |
| PE-28 | | | | | 50 |
| IBOMA | 50 | 50 | 50 | 50 | 50 |
| TPO | 2 | 2 | 2 | 2 | 2 |

TABLE 8

Example formulations (amounts in parts by weight)

| Component | EX-20 | EX-21 | EX-22 | EX-23 | EX-24 | EX-25 |
|---|---|---|---|---|---|---|
| PE-25 | 25 | 18 | | 10 | 15 | |
| PE-13 | 25 | 32 | 25 | | 35 | |
| PE-19 | | | 25 | | | |
| PE-26 | | | | 40 | | |
| PE-30 | | | | | | 40 |
| PE-14 | | | | | | 10 |
| AdMA | | | | | | 50 |

TABLE 8-continued

Example formulations (amounts in parts by weight)

| Component | EX-20 | EX-21 | EX-22 | EX-23 | EX-24 | EX-25 |
|---|---|---|---|---|---|---|
| IBOMA | 50 | 50 | 50 | 50 | 50 | |
| TPO | 2 | 2 | 2 | 2 | 2 | 2 |

TABLE 9

Example formulations (amounts in parts by weight)

| Component | EX-26 | EX-27 | EX-28 | EX-29 | EX-30 |
|---|---|---|---|---|---|
| PE-13 | 45 | 40 | | | |
| PE-30 | | | 47.5 | | |
| PE-32 | | | | 47.5 | |
| PE-33 | 5 | 10 | 2.5 | 2.5 | 5 |
| PE-11 | | | | | 45 |
| IBOMA | 50 | 50 | 50 | 50 | 50 |
| TPO | 2 | 2 | 2 | 2 | 2 |

TABLE 10

Example formulations (amounts in parts by weight)

| Component | EX-31 | EX-32 | EX-33 | EX-34 | EX-35 | EX-36 |
|---|---|---|---|---|---|---|
| PE-5 | 40 | 40 | 40 | 40 | | |
| PE-7 | | | | | 40 | 40 |
| PE-9 | 10 | | | | | |
| PE-10 | | 10 | | | | |
| PE-11 | | | 10 | | | |
| PE-12 | | | | 10 | | |
| PE-15 | | | | | 10 | |
| PE-16 | | | | | | 10 |
| IBOMA | 50 | 50 | 50 | 50 | 50 | 50 |
| TPO | 2 | 2 | 2 | 2 | 2 | 2 |

TABLE 11

Example formulations (amounts in parts by weight)

| Component | EX-37 | EX-38 | EX-39 | EX-40 |
|---|---|---|---|---|
| PE-7 | 40 | 40 | | |
| PE-5 | | | 45 | |
| PE-32 | | | | 50 |
| C-590 diol MA | 10 | | | |
| C-2050 diol MA | | 10 | | |
| DDDMA | | | 5 | |
| HDDMA | | | | 10 |
| IBOMA | 50 | 50 | 50 | 40 |
| TPO | 2 | 2 | 2 | 2 |

TABLE 12

Example formulations (amounts in parts by weight)

| Components | EX-41 | EX-42 | EX-43 | EX-44 | EX-45 | EX-46 | EX-47 | EX-48 | EX-49 |
|---|---|---|---|---|---|---|---|---|---|
| PE-19 | 50 | | | | | | | | |
| PE-5 | | 40 | 60 | | | | | | |
| PE-32 | | | | 50 | 50 | 50 | 50 | | |
| PE-14 | | | | | | | | 45 | |
| PE-33 | | | | | | | | 5 | |
| PE-7 | | | | | | | | | 50 |
| IBOMA | | 60 | 40 | | | | | 50 | |
| DiCPMA | 50 | | | | 50 | | | | |
| AdMA | | | | 50 | | | | | |
| tBuCHMA | | | | | | 50 | | | |
| CHMA | | | | | | | 50 | | |
| TMCHMA | | | | | | | | | 50 |
| TPO | 2 | 2 | 2 | 2 | 2 | 2 | 2 | 2 | 2 |

TABLE 13

Example formulations (amounts in parts by weight)

| Components | EX-50 | EX-51 | EX-52 | EX-53 | EX-54 | EX-55 |
|---|---|---|---|---|---|---|
| PE-19 | 50 | | | | | |
| PE-22 | | 50 | | | | |
| PE-27 | | | 50 | | | |
| PE-34 | | | | 50 | | |
| PE-35 | | | | | 50 | |
| PE-36 | | | | | | 50 |
| IBOMA | | | 50 | 50 | 50 | 50 |
| IBOA | 50 | 50 | | | | |
| TPO | 2 | 2 | 2 | 2 | 2 | 2 |

TABLE 14

Example formulations (amounts in parts by weight)

| Components | EX-79 | EX-80 | EX-81 | EX-82 | EX-83 | EX-84 | EX-85 |
|---|---|---|---|---|---|---|---|
| PE-13 | | | | 45 | | | |
| PE-32 | | | | | | | 50 |
| PE-45 | 50 | | | | | | |
| PE-46 | | 50 | | | | | |
| PE-47 | | | 50 | | | | |
| PE-48 | | | | 5 | | | |
| PE-49 | | | | | 50 | | |
| PE-50 | | | | | | 50 | |
| tBuCHMA | | | | | | | 50 |
| IBOMA | 50 | 50 | 50 | 50 | 50 | 50 | |
| TPO | 2 | 2 | 2 | 2 | 2 | 2 | 2 |

TABLE 15

Example formulations (amounts in parts by weight)

| Components | EX-87 | EX-88 | EX-89 |
|---|---|---|---|
| Exothane 10 | | | 10 |
| PE-44 | 50 | 50 | 40 |
| IBOMA | 40 | 30 | 50 |
| HEMA | 10 | 20 | |
| TPO | 2 | 2 | 2 |

TABLE 16

Comparative example formulations (amounts in parts by weight)

| Components | CE-1 | CE-2 | CE-3 | CE-4 | CE-5 | CE-6 |
|---|---|---|---|---|---|---|
| PE-32 | 50 | 50 | 50 | 50 | | |
| Exothane 10 | | | | | 30 | 50 |
| CEA | | | | | 50 | |
| NVP | | | | | 20 | |
| IBOMA | | | | | | 50 |
| EHMA | | | | 50 | | |
| PEMA | 50 | | | | | |
| PEG600DMA | | | 50 | | | |
| THFMA | | 50 | | | | |
| TPO | 2 | 2 | 2 | 2 | 2 | 2 |

TABLE 17

Comparative example formulations (amounts in parts by weight)

| Components | CE-7 | CE-8 | CE-9 | CE-10 | CE-11 | CE-12 |
|---|---|---|---|---|---|---|
| Exothane 108 | 50 | | | | | |
| PE-18 | | 50 | | | | |
| PE-17 | | | 50 | | | |
| PE-5 | | | | 30 | 70 | |
| PE-4 | | | | | | 50 |
| IBOMA | 50 | 50 | 50 | 70 | 30 | 50 |
| TPO | 2 | 2 | 2 | 2 | 2 | 2 |
| BHT | | 0.025 | | 0.025 | 0.025 | |

Polymer/Oligomer Molecular Weight Characterization Method:

The molecular weights of the oligomers and the polymers were characterized using gel permeation chromatography (GPC). The GPC equipment consisted of an e2695 Separation Module and a 2414 dRI detector, both from Waters Corporation (Milford, Mass.). It was operated at a flow rate of 0.6 mL/min using tetrahydrofuran as the eluent. The GPC column was a HSPgel HR MB-M column also from Waters Corporation. The column compartment and differential refractive index detector were set to 35° C. The molecular weight standards were EasiVial PMMA from Agilent Technologies (The $M_p$ values of the PMMA molecular weight standards used in the calibration curve ranged from 550 D to 1,568,000 g/mol.) The relative number average molecular weight (Mn) and weight average molecular weight (Mn) of selected oligomers/polymers are tabulated below in Table 18, in kiloDaltons (kD):

TABLE 18

| Sample | Mn (kD) | Mw (kD) | Polydispersity |
|---|---|---|---|
| PE-6 | 4.3 | 18.1 | 4.2 |
| PE-7 | 3.5 | 12.1 | 3.4 |
| PE-8 | 3.5 | 12.4 | 3.5 |
| PE-9 | 3.0 | 7.5 | 2.5 |
| PE-10 | 3.1 | 7.4 | 2.4 |
| PE-11 | 3.1 | 8.1 | 2.6 |
| PE-12 | 3.3 | 8.7 | 2.6 |
| PE-13 | 4.3 | 17.9 | 4.1 |
| PE-14 | 4.5 | 11.5 | 2.6 |
| PE-17 | 1.6 | 6.3 | 4.1 |
| PE-18 | 3.8 | 12.9 | 3.4 |
| PE-19 | 2.1 | 8.9 | 4.3 |
| PE-20 | 5.0 | 16.4 | 3.3 |
| PE-21 | 3.7 | 14.3 | 3.9 |
| PE-22 | 3.1 | 11.6 | 3.7 |
| PE-23 | 3.9 | 17.0 | 4.4 |
| PE-24 | 3.4 | 14.0 | 4.1 |
| PE-25 | 2.0 | 5.6 | 2.8 |
| PE-26 | 2.9 | 12.8 | 4.3 |
| PE-27 | 3.3 | 14.0 | 4.3 |
| PE-28 | 2.8 | 12.3 | 4.4 |

TABLE 18-continued

| Sample | Mn (kD) | Mw (kD) | Polydispersity |
|---|---|---|---|
| PE-29 | 3.6 | 11.5 | 3.2 |
| PE-30 | 2.9 | 12.9 | 4.4 |
| PE-31 | 2.0 | 9.8 | 4.9 |
| PE-32 | 3.9 | 12.1 | 3.1 |
| PE-33 | 4.1 | 14.4 | 3.5 |
| PE-35 | 3.5 | 12.9 | 3.7 |
| PE-36 | 3.6 | 12.0 | 3.4 |
| PE-39 | 7.4 | 21.8 | 3.0 |
| PE-40 | 11.3 | 30.5 | 2.7 |
| PE-41 | 2.8 | 6.3 | 2.2 |
| PE-42 | 3.9 | 9.1 | 2.3 |
| PE-43 | 6.3 | 15.8 | 2.5 |
| PE-44 | 4.6 | 12.8 | 2.8 |
| PE-45 | 14.3 | 24.6 | 1.7 |
| PE-46 | 15.6 | 25.8 | 1.8 |
| PE-47 | 18.3 | 32.1 | 1.8 |

General Procedure of Formulation Casting and Curing

Each formulation indicated in Tables 5-17 was poured into a silicone dogbone mold (Type V mold of 1 mm thickness, ASTM D638-14) for preparing tensile specimens, and a rectangular mold of dimensions (9.4 mm×25.4 mm×1 mm) for DMA 3-point bend test specimens. A 2 mil (0.05 mm) polyethylene terephthalate (PET) release liner (obtained under the trade designation "SCOTCHPAK" from 3M Company (St. Paul, Minn.)) was rolled on the filled mold, and the filled mold along with the liner was placed between two glass plates held by binder clips. The formulation was cured under a Asiga Pico Flash post-curing chamber (obtained from Asiga USA, Anaheim Hills, Calif.) for 30 minutes. The specimens were removed from the mold followed by additional light exposure for 30 minutes using the Asiga Pico Flash post-curing chamber. Specimens were then kept in an oven set at 100° C. for 30 minutes. The dogbone specimens were conditioned in Phosphate-buffered saline (PBS, 1×, pH=7.4) for 24 hours at 37° C. The DMA 3-point bend test specimens were conditioned in de-ionized (DI) water for 48 hours at room temperature.

General Procedure for Determination of Loss Modulus and Tan Delta Using Dynamic Mechanical Analysis Dynamic mechanical analysis (DMA) was performed on rectangular cured samples (approximately 25.4 mm×9.4 mm×1 mm) using a TA Instruments model Q800 dynamic mechanical analyzer (TA Instruments (Newcastle, Del.)) using a tension clamp in controlled strain mode, 0.2% strain, 0.02 N preload force, 125% force track, 1 Hz. Temperature was swept at a rate of 2° C./min from −40° C. to 200° C. Samples were immersed in deionized water at 37° C. for least 24 hours, at which time the samples were fully saturated with water prior to testing and tested immediately after removal from water.

TABLE 19

Measured physical properties of samples.

| Sample | Resin 1 | Resin 2 | Peak loss modulus (° C.) | Peak Tan delta (° C.) |
|---|---|---|---|---|
| EX-8 | PE-7 | IBOMA | 2 | 121 |
| EX-47 | PE-32 | CHMA | 0 | 73 |
| CE-12 | PE-4 | IBOMA | 44 | 129 |
| EX-44 | PE-32 | AdMA | 5 | 117 |
| CE-1 | PE-32 | PEMA | −7 | 31 |
| CE-4 | PE-32 | EHMA | −21 | 26 |

TABLE 19-continued

Measured physical properties of samples.

| Sample | Resin 1 | Resin 2 | Peak loss modulus (° C.) | Peak Tan delta (° C.) |
|---|---|---|---|---|
| EX-51 | PE-22 | IBOA | −14 | 67 |
| CE-6 | Exothane 10 | IBOMA | 31 | 124 |

Additive Manufacturing of Formulated Resins

Unless otherwise noted, all 3D-printed examples were manufactured either on an Asiga Pico 2 HD or Asiga Max, a vat polymerization 3D printer available from Asiga USA, Anaheim Hills, Calif. Each formulation listed in Tables 20-23 was photopolymerized on an Asiga 3D printer with a LED light source of 385 nm. Tensile test bars of Type V according to ASTM D638-14 (2014) and DMA 3-point bend test specimens were manufactured. The resin bath of the printer was heated to 35-50° C. before photopolymerization to reduce the viscosity to be able to manufacture the tensile test bars. The following settings were used for the printing: slice thickness=50 µm; burn in layers=1; separation velocity=1.5 mm/s, separation distance=10 mm, approach velocity=1.5 mm/s. On the Asiga Pico 2 HD, 1 slide per layer was used at a speed of 7 mm/min. In addition, Table 24 describes the printer type, and the exposure time, burn-in time, and temperature used for printing the formulations indicated in Tables 20-23. The printed parts were washed using propylene carbonate followed by isopropanol to remove unreacted resin. The printed part was then post-cured using Asiga Pico Flash post-curing chamber for 90 minutes on each side followed by heating in an oven at 100° C. for 30 minutes. The dogbone specimens were conditioned in phosphate-buffered saline (PBS, 1×, pH=7.4) for 24 hours at 37° C. The DMA 3-point bend test specimens were conditioned in DI water for 48 hours at room temperature.

TABLE 20

Example formulations for additive manufacturing (amounts in parts by weight)

| Components | EX-56 | EX-57 | EX-58 | EX-59 | EX-60 |
|---|---|---|---|---|---|
| PE-43 | 50 | | | | |
| PE-44 | | 50 | 50 | 50 | |
| PE-32 | | | | | 50 |
| IBOMA | 50 | 50 | 50 | 50 | 50 |
| TPO | 2 | 2 | 0.5 | 0.5 | |
| BHT | 0.025 | 0.025 | 0.025 | 0.025 | 0.025 |
| Omnirad 379 | | | | | 0.75 |
| NapA | 0.025 | 0.025 | 0.1 | | 0.0175 |
| Tinuvin 326 | | | | 0.025 | |

TABLE 21

Example formulations for additive manufacturing (amounts in parts by weight)

| Components | EX-61 | EX-62 | EX-63 | EX-64 | EX-65 | EX-66 | EX-67 |
|---|---|---|---|---|---|---|---|
| PE-7 | 47 | | | | | | |
| PE-5 | | 44 | | | | | |
| PE-6 | | | 50 | | | | |
| PE-37 | | | | 50 | | | |
| PE-25 | | | | | 25 | | |
| PE-13 | | | | | 25 | 25 | 20 |
| PE-19 | | | | | | 25 | 30 |
| IBOMA | 53 | 56 | 50 | 50 | 50 | 50 | 50 |
| TPO | 2 | 2 | 2 | 2 | 2 | 2 | 2 |
| BHT | 0.025 | 0.025 | 0.025 | 0.025 | 0.025 | 0.025 | 0.025 |
| NapA | 0.025 | 0.025 | 0.025 | 0.025 | 0.025 | 0.025 | 0.025 |

TABLE 22

Example formulations for additive manufacturing (amounts in parts by weight)

| Components | EX-68 | EX-69 | EX-70 | EX-71 | EX-72 | EX-73 | EX-74 |
|---|---|---|---|---|---|---|---|
| PE-5 | | | | | | | |
| PE-19 | 50 | | | | | | |
| PE-44 | | 49.42 | 45.22 | 44.69 | 44.16 | 39.96 | |
| PE-33 | | 5.58 | 9.78 | 7.81 | 5.84 | 10.04 | 5 |
| PE-13 | | | | | | | 45 |
| IBOMA | 40 | 45 | 45 | 47.5 | 50 | 50 | 50 |
| HDDMA | 10 | | | | | | |
| TPO | 0.5 | 2 | 2 | 2 | 2 | 2 | 2 |
| BHT | 0.025 | 0.025 | 0.025 | 0.025 | 0.025 | 0.025 | 0.025 |
| NapA | 0.1 | 0.025 | 0.025 | 0.025 | 0.025 | 0.025 | 0.025 |

TABLE 23

Example formulations for additive manufacturing (amounts in parts by weight)

| Components | EX-75 | EX-76 | EX-77 | EX-78 | EX-86 |
|---|---|---|---|---|---|
| PE-19 | 50 | | | | |
| PE-32 | | 50 | | | |
| PE-13 | | | 50 | | |
| PE-30 | | | | 40 | |
| PE-14 | | | | 10 | |
| PE-47 | | | | | 50 |
| DiCPMA | 50 | | | | |
| AdMA | | 50 | 50 | 50 | |
| IBOMA | | | | | 50 |
| TPO | 2 | 2 | 2 | 2 | 2 |
| BHT | 0.025 | 0.025 | 0.025 | 0.025 | 0.025 |
| NapA | 0.025 | 0.025 | 0.025 | 0.025 | |
| Tinuvin 326 | | | | | 0.025 |

TABLE 24

Additive manufacturing conditions.

| Example | Printer | Exposure Time (sec) | Burn-in Time (sec) | Temperature (° C.) |
|---|---|---|---|---|
| EX-56 | Asiga Pico 2 HD | 2.25 | 15 | 50 |
| EX-57 | Asiga Max | 3 | 10 | 40 |
| EX-58 | Asiga Max | 5 | 10 | 40 |
| EX-59 | Asiga Pico 2 HD | 3.75 | 20 | 50 |
| EX-60 | Asiga Max | 4.5 | 10 | 40 |
| EX-61 | Asiga Pico 2 HD | 2 | 8 | 50 |
| EX-62 | Asiga Pico 2 HD | 2.5 | 8 | 50 |
| EX-63 | Asiga Max | 2.5 | 10 | 40 |
| EX-64 | Asiga Pico 2 HD | 2 | 8 | 50 |
| EX-65 | Asiga Pico 2 HD | 2 | 8 | 50 |
| EX-66 | Asiga Max | 3 | 10 | 40 |
| EX-67 | Asiga Pico 2 HD | 2 | 8 | 50 |
| EX-68 | Asiga Pico 2 HD | 2 | 8 | 50 |
| EX-69 | Asiga Max | 3 | 10 | 40 |
| EX-70 | Asiga Max | 3 | 10 | 40 |
| EX-71 | Asiga Max | 3 | 10 | 40 |
| EX-72 | Asiga Max | 3 | 10 | 40 |
| EX-73 | Asiga Max | 3 | 10 | 40 |
| EX-74 | Asiga Pico 2 HD | 2 | 8 | 50 |
| EX-75 | Asiga Pico 2 HD | 2 | 8 | 50 |
| EX-76 | Asiga Pico 2 HD | 2 | 8 | 50 |
| EX-77 | Asiga Pico 2 HD | 2 | 8 | 50 |
| EX-78 | Asiga Pico 2 HD | 2 | 8 | 50 |
| EX-86 | Asiga Max | 5 | 10 | 40 |

General Procedure for Tensile Testing

PBS conditioned dogbones were tested on an Instron 5944 (Instron, Norwood, Mass.) with a 500 N load cell. The test speed was 5 mm/minute and the initial grip separation was 1 inch (2.5 cm). The gauge length was set to 1 inch (2.5 cm). Five replicate samples for each formulation were tested, and the average value are reported. The tensile strength at yield was determined according to ASTM D638-14 (2014) and shown in Table 25 and Table 26 below. For specimens that did not yield, maximum tensile strength was determined. Elongation at break was determined from the crosshead movement of the grips.

General Procedure for the Determination of Relaxation Modulus Using Dynamic Mechanical Analysis Rectangular specimens were water conditioned by soaking in deionized water for 48 hours at room temperature at 22 to 25° C. and were tested in a TA Q800 DMA equipped with a submersion 3-point bending clamp. The water conditioned rectangular specimens were placed in water filled submersion fixture. The specimens were equilibrated for 10 minutes at 37° C., followed by applying a 2% strain. Relaxation modulus was measured for 30 minutes using TA Advantage software, and is reported in Tables 25 and 26.

TABLE 25

Yield strength, elongation and relaxation modulus of cast formulations.

| Sample | Strength at Yield (MPa) | Elongation at Break (%) | Initial Relaxation Modulus (MPa) | Relaxation Modulus at 30 Minutes (MPa) | Percent Loss of Relaxation Modulus After 30 Minutes |
|---|---|---|---|---|---|
| CE-1 | 9.3* | 167.5 | N.M1 | N.M1 | N.M1 |
| CE-2 | 8.6* | 181.1 | N.M1 | N.M1 | N.M1 |
| CE-3 | 1.3* | 5.8 | N.M1 | N.M1 | N.M1 |
| CE-4 | 2.9* | 87.7 | N.M1 | N.M1 | N.M1 |
| CE-5 | 1.2* | 32.0 | N.M2 | N.M2 | N.M2 |
| CE-6 | 46.9 | 2.9 | 1662.0 | 712.5 | 57.1 |
| CE-7 | 26.1 | 9.3 | 1027.0 | 265.8 | 74.1 |
| CE-8 | 15.2 | 122.7 | 401.5 | 51.2 | 87.2 |
| CE-9 | 15.7* | 1.0 | N.M2 | N.M2 | N.M2 |
| CE-10 | 29.3* | 1.7 | N.M2 | N.M2 | N.M2 |
| CE-11 | 25.2* | 130.9 | 106.2 | 17.2 | 83.8 |
| CE-12 | 64.8* | 2.8 | 2829.0 | 1859.0 | 34.3 |
| EX-1 | 56.2 | 7.6 | 1442.0 | 720.9 | 50.0 |
| EX-2 | 42.0 | 12.9 | 798.4 | 313.4 | 60.7 |
| EX-3 | 28.7 | 84.2 | 594.3 | 212.9 | 64.2 |
| EX-4 | 30.7 | 38.9 | 794.8 | 312.4 | 60.7 |
| EX-5 | 22.1 | 80.8 | 540.8 | 214.2 | 60.4 |
| EX-6 | 17.6 | 113.9 | 498.5 | 198.8 | 60.1 |
| EX-7 | 39.1 | 17.1 | 1213.0 | 545.1 | 55.1 |
| EX-42 | 39.7 | 16.5 | 1096.0 | 557.9 | 49.1 |
| EX-43 | 17.4 | 92.7 | 438.1 | 84.1 | 80.8 |
| EX-9 | 22.2 | 36.4 | 632.3 | 174.3 | 72.4 |
| EX-10 | 20.2 | 90.3 | 565.6 | 182.2 | 67.8 |
| EX-11 | 22.5 | 70.0 | 740.8 | 219.8 | 70.3 |
| EX-12 | 14.7 | 75.8 | 500.1 | 143.2 | 71.4 |
| EX-13 | 27.7 | 46.3 | 922.2 | 365.7 | 60.3 |
| EX-14 | 28.5 | 46.7 | 867.1 | 380.8 | 56.1 |
| EX-15 | 23.1 | 90.7 | 655.8 | 258.5 | 60.6 |
| EX-16 | 38.3 | 12.2 | 949.6 | 458.8 | 51.7 |
| EX-50 | 17.2 | 64.1 | 263.4 | 17.6 | 93.3 |
| EX-17 | 26.8 | 44.7 | 763.1 | 219.6 | 71.2 |
| EX-18 | 21.1 | 65.5 | 498.0 | 147.6 | 70.4 |
| EX-19 | 23.5 | 15.5 | 772.8 | 295.0 | 61.8 |
| EX-20 | 35.5 | 25.1 | 1020.0 | 434.7 | 57.4 |
| EX-21 | 33.2 | 30.9 | 977.7 | 391.6 | 59.9 |
| EX-24 | 27.3 | 66.6 | 780.3 | 287.9 | 63.1 |
| EX-23 | 32.9 | 54.9 | 1173.0 | 397.1 | 66.1 |
| EX-22 | 30.4 | 48.0 | 859.1 | 368.4 | 57.1 |
| EX-44 | 33.3 | 27.5 | 837.5 | 325.0 | 61.2 |
| EX-45 | 21.5 | 67.9 | 369.7 | 71.9 | 80.6 |
| EX-41 | 32.8 | 35.2 | 808.1 | 229.3 | 71.6 |
| EX-46 | 16.6 | 66.6 | 345.8 | 73.6 | 78.7 |
| EX-47 | 14.0 | 125.6 | 169.0 | 13.9 | 91.8 |
| EX-29 | 28.4 | 37.8 | 746.3 | 267.7 | 64.1 |
| EX-28 | 29.0 | 34.7 | 879.7 | 362.3 | 58.8 |
| EX-26 | 30.8 | 47.5 | 824.4 | 366.9 | 55.4 |
| EX-27 | 37.8 | 12.5 | 985.1 | 476.6 | 51.6 |
| EX-31 | 24.1 | 63.7 | 612.6 | 201.5 | 67.1 |
| EX-32 | 24.7 | 58.1 | 602.8 | 197.0 | 67.3 |
| EX-33 | 26.8 | 53.9 | 691.4 | 246.8 | 64.3 |
| EX-34 | 26.3 | 57.1 | 577.6 | 172.8 | 70.1 |
| EX-35 | 27.8 | 53.0 | 698.4 | 220.0 | 68.5 |
| EX-36 | 34.4 | 28.4 | 882.6 | 327.2 | 62.9 |
| EX-25 | 28.7 | 56.3 | 738.1 | 285.1 | 61.4 |
| EX-30 | 23.3 | 51.0 | 458.0 | 109.0 | 76.2 |
| EX-48 | 24.1 | 28.2 | 591.9 | 177.3 | 70.0 |
| EX-37 | 30.0 | 29.2 | 691.0 | 251.7 | 63.6 |
| EX-38 | 24.6 | 66.0 | 640.6 | 196.0 | 69.4 |
| EX-39 | 32.8 | 30.5 | 916.3 | 410.2 | 55.2 |
| EX-40 | 21.3 | 66.2 | 570.5 | 156.7 | 72.5 |
| EX-8 | 26.9 | 54.4 | 765.0 | 264.7 | 65.4 |
| EX-49 | 22.2* | 75.5 | 261.1 | 56.1 | 78.5 |

TABLE 25-continued

Yield strength, elongation and relaxation modulus of cast formulations.

| Sample | Strength at Yield (MPa) | Elongation at Break (%) | Initial Relaxation Modulus (MPa) | Relaxation Modulus at 30 Minutes (MPa) | Percent Loss of Relaxation Modulus After 30 Minutes |
|---|---|---|---|---|---|
| EX-52 | 27.8 | 63.4 | 749.0 | 282.4 | 62.3 |
| EX-53 | 25.1 | 53.0 | 636.2 | 236.1 | 62.9 |
| EX-54 | 27.9 | 53.5 | 761.9 | 264.1 | 65.3 |
| EX-55 | 26.1 | 49.9 | 746.3 | 258.6 | 65.3 |
| EX-51 | 18.8* | 101.0 | 121.1 | 20.5 | 83.1 |
| EX-79 | 35.0 | 14.9 | 1051.0 | 457.8 | 56.4 |
| EX-80 | 19.6* | 28.5 | 486.0 | 190.0 | 60.9 |
| EX-81 | 30.1 | 33.3 | 891.0 | 369.7 | 58.5 |
| EX-82 | 32.7 | 24.2 | 924.5 | 441.3 | 52.3 |
| EX-83 | 26.3 | 50.2 | 741.5 | 335.4 | 54.8 |
| EX-84 | 29.7 | 30.4 | 649.4 | 311.8 | 52.0 |
| EX-85 | 16.6 | 66.6 | 345.8 | 73.6 | 78.7 |
| EX-87 | 26.6 | 66.6 | 486.2 | 74.5 | 84.7 |
| EX-88 | 16.6 | 91.9 | 316.7 | 21.7 | 93.14 |
| EX-89 | 36 | 23.3 | 926.9 | 346.3 | 62.64 |

N.M1. Not measured since these samples were very flexible and soft, and couldn't be successfully clamped for DMA testing.
N.M2. Not measured since these specimens were very brittle.
*maximum tensile strength is reported for specimens that did not yield.

TABLE 26

Yield strength, elongation and relaxation modulus of printed formulations.

| Sample | Strength at Yield (MPa) | Elongation at Break (%) | Initial Relaxation Modulus (MPa) | Relaxation Modulus at 30 Minutes (MPa) | Percent Loss of Relaxation Modulus After 30 Minutes |
|---|---|---|---|---|---|
| EX-56 | 24.1 | 91.2 | 536.0 | 187.6 | 65.0 |
| EX-57 | 25.0 | 103.0 | 722.5 | 252.7 | 65.0 |
| EX-58 | 21.6 | 83.8 | 666.1 | 227.7 | 65.8 |
| EX-59 | 21.9 | 126.4 | 612.7 | 194.4 | 68.3 |
| EX-60 | 23.8 | 93.2 | 675.7 | 226.5 | 66.5 |
| EX-61 | 28.3 | 96.7 | 857.5 | 325.0 | 62.1 |
| EX-62 | 36.5 | 24.7 | 1175.0 | 460.1 | 60.8 |
| EX-63 | 29.0 | 76.4 | 710.8 | 277.7 | 60.9 |
| EX-64 | 27.1 | 126.0 | 805.2 | 303.4 | 62.3 |
| EX-65 | 31.3 | 70.4 | 978.2 | 383.7 | 60.8 |
| EX-66 | 25.0 | 111.1 | 406.3 | 157.2 | 61.3 |
| EX-67 | 29.4 | 75.0 | 879.5 | 368.8 | 58.1 |
| EX-68 | 24.2 | 32.8 | 620.9 | 211.2 | 66.0 |
| EX-69 | 26.7 | 65.5 | 696.4 | 249.4 | 64.2 |
| EX-70 | 35.6 | 41.2 | 1007.0 | 436.1 | 56.7 |
| EX-71 | 35.7 | 43.5 | 983.0 | 441.2 | 55.1 |
| EX-72 | 36.6 | 42.9 | 925.3 | 413.6 | 55.3 |
| EX-73 | 43.7 | 20.6 | 1199.0 | 564.8 | 52.9 |
| EX-74 | 23.8 | 98.7 | 649.0 | 261.8 | 59.7 |
| EX-75 | 28.9 | 74.7 | 800.3 | 249.1 | 68.9 |
| EX-76 | 30.3 | 88.7 | 789.4 | 288.3 | 63.5 |
| EX-77 | 22.7 | 144.9 | 738.1 | 285.1 | 61.4 |
| EX-78 | 27.6 | 95.9 | 707.1 | 265.0 | 62.5 |
| EX-86 | 28.9 | 28.3 | 715.4 | 322.7 | 54.9 |

Additive Manufacturing of Aligner Articles from the Formulated Resin

The formulation of EX-57 was photopolymerized on the Asiga Max printer with a LED light source of 385 nm. A stereolithography file format (STL file) of the aligner was loaded into the Asiga Composer software, and support structures were generated. The resin bath of the printer was heated to 40° C. before photopolymerization to reduce the viscosity to be able to manufacture the article. The following settings were used for the printing: slice thickness=50 μm; burn in layers=1; separation velocity=1.5 mm/min, burn-in exposure time=10 sec; exposure time=3 sec. The printed part was washed using propylene carbonate followed by isopropanol to remove unreacted resin. The printed specimen was then post-cured using an Asiga Pico Flash post-curing chamber for 90 minutes on each side. The photopolymerized aligners fit the models, showing precision of the additive manufacture part. The aligner had acceptable strength and flexibility.

Test Procedure for Gravimetric Analysis of Extractable from Printed Articles

Articles shaped as a continuous 5-tooth row (30.4 mm×9.24 mm×8.17 mm) using formulations of EX-57 and EX-58 were printed and post processed according to the procedure described above. The thickness of the article was 0.49 mm. 3×5-tooth articles (total surface area of 45 cm$^2$) were placed in a 40 mL glass vial and weighed. 15 mL of solvent (either heptane or 5% ethanol/Milli-Q water) was added to the vial, with one 15 mL blank (vial without articles) for each solvent. The vials were covered with TEFLON caps, and the samples were kept at 37° C. for 24 hours while shaking at 80 RPM in a LabLine Bench top incubated shaker Model 4628. The samples were allowed to cool before transferring the extraction solution to a new 20 mL glass vial. A 5 mL aliquot was transferred to a preweighed 8 mL glass vial and set to evaporate under a nitrogen purge. The vials were weighed once the solvent dried off, until a constant weight was reached. % Residue was calculated using the following formula shown below. The test was completed in triplicates, all run at the same time, and result shown is the average of the three replicates.

$$\% \text{ Residue} = \left[ \frac{(\text{Vial after evaporation(g)} - \text{Vial tare(g)}) * \frac{15 \text{ mL solvent}}{5 \text{ mL solvent analyzed}}}{\text{Mass of article (g)}} \right] * 100$$

TABLE 27

| Sample | % Extractable in Heptane | % Extractable in 5% EtOH/H$_2$O |
|---|---|---|
| EX-57 | 0.444 | 0.129 |
| EX-58 | 0.280 | 0.072 |

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

The invention claimed is:

1. An orthodontic article comprising:
 a) a polymerized reaction product of a photopolymerizable composition comprising:
  i) a monofunctional (meth)acrylate monomer whose cured homopolymer has a T$_g$ of 90° C. or greater;
  ii) a photoinitiator; and
  iii) a polymerization reaction product of components, the components comprising:
   1) an isocyanate;
   2) a (meth)acrylate mono-ol;
   3) a polycarbonate diol of Formula (I):

$$H(O\!-\!R_1\!-\!O\!-\!C(\!=\!O))_m\!-\!O\!-\!R_2\!-\!OH \quad (I)$$

wherein each of R$_1$ in each (O—R$_1$—O—C(=O)) repeat unit and each R$_2$ are independently an aliphatic, cycloaliphatic, or aliphatic/cycloaliphatic alkylene group and an average number of carbon atoms in a combination of all the R$_1$ and R$_2$ groups is 4 to 10, and m is 2 to 23; and
  4) a catalyst;
 wherein the polymerized reaction product of the photopolymerizable composition has a shape of the orthodontic article.

2. The orthodontic article of claim 1, wherein the (meth)acrylate mono-ol is of Formula (II):

$$\text{HO-Q-(A)}_p \quad (II)$$

wherein Q is a polyvalent organic linking group, A is a (meth)acryl functional group of the formula —XC(=O)C(R$_3$)=CH$_2$, wherein X is O, S, or NR$_4$, R$_4$ is H or an alkyl of 1 to 4 carbon atoms, R$_3$ is a lower alkyl of 1 to 4 carbon atoms or H, and wherein p is 1 or 2.

3. The orthodontic article of claim 1, wherein the photopolymerizable composition further comprises a compound of Formula (III):

$$(H_2C\!=\!C(R_3)C(\!=\!O)\!-\!X)_p\text{-Q-OC}(\!=\!O)NH\!-\!R_{di}\!-\!\\ NHC(\!=\!O)O\text{-Q-}(X\!-\!C(\!=\!O)(R_3)C\!=\!CH_2)_p \quad (III),$$

wherein X, Q, p, and R$_3$ are as defined for Formula (II), and R$_{di}$ is the residue of a diisocyanate.

4. The orthodontic article of claim 3, wherein the compound of Formula (III) is added to the photopolymerizable composition.

5. The orthodontic article of claim 3, wherein the compound of Formula (III) is present in an amount of 5 to 20 wt. %, based on the weight of the polymerizable composition.

6. The orthodontic article of claim 3, wherein the compound of Formula (III) is of Formula (IV):
 (IV).

7. The orthodontic article of claim 1, wherein the monofunctional (meth)acrylate monomer is selected from the group consisting of dicyclopentadienyl acrylate, isobornyl acrylate, dicyclopentanyl acrylate, dimethyl-1-adamantyl acrylate, cyclohexyl methacrylate, tert-butyl methacrylate, 3,3,5-trimethylcyclohexyl methacrylate, cis-4-tert-butyl-cyclohexylmethacrylate, 2-decahydronapthyl methacrylate, 1-adamantyl acrylate, 73/27 trans/cis-4-tert-butylcyclohexylmethacrylate, dicyclopentadienyl methacrylate, dicyclopentanyl methacrylate, trans-4-tert-butylcyclohexyl methacrylate, d,l-isobornyl methacrylate, dimethyl-1-adamantyl methacrylate, d,l-bornyl methacrylate, 3-tetracyclo[4.4.0.1.1]dodecyl methacrylate, 1-adamantyl methacrylate, or combinations thereof.

8. The orthodontic article of claim 1, wherein the polycarbonate diol has a molecular weight of 800 g/mol to 2,200 g/mol, or 1,800 g/mol to 2,200 g/mol.

9. The orthodontic article of claim 1, wherein the photopolymerizable composition further comprises a UV absorber comprising an optical brightener in an amount of 0.001 to 5% by weight, based on the total weight of the photopolymerizable composition.

10. The orthodontic article of claim 9, wherein the optical brightener comprises a compound of Formula (V):
 (V).

11. The orthodontic article of claim 1, wherein the polyurethane (meth)acrylate polymer has a molecular weight of 6,000 g/mol to 35,000 g/mol.

12. The orthodontic article of claim 1, wherein a cured homopolymer of the monofunctional (meth)acrylate monomer has a T$_g$ of 100° C. or greater, 170° C. or greater, or 180° C. or greater.

13. The orthodontic article of claim 1, exhibiting at least two properties selected from the group consisting of an initial relaxation modulus of 100 megapascals (MPa) or greater measured at 2% strain at 37° C., a percent loss of relaxation modulus of 70% or less, a 30 minute relaxation modulus of 100 MPa or greater, an elongation at break of a printed article of 20% or greater, and a tensile strength at yield of 14 MPa or greater.

14. The orthodontic article of claim 1, exhibiting a peak in loss modulus of 20° C. or less and a tan delta peak of 80° C. or greater.

15. The orthodontic article of claim 1, further comprising an inhibitor in an amount of 0.001 to 1 wt. %, based on the total weight of the photopolymerizable composition.

16. The orthodontic article of claim 1, wherein the photoinitiator is present in an amount of 0.2 wt. % to 5 wt. %.

17. The orthodontic article of claim 1, wherein the monofunctional (meth)acrylate monomer has a log of octanol/water partition coefficient (log P) value of greater than 3, greater than 2, or greater than 1.

18. A method of making an orthodontic article, the method comprising:
 a) obtaining a photopolymerizable composition comprising:
  i) a monofunctional (meth)acrylate monomer whose cured homopolymer has a $T_g$ of 90° C. or greater;
  ii) a photoinitiator; and
  iii) a polymerization reaction product of components, the components comprising:
   1) an isocyanate;
   2) a (meth)acrylate mono-ol;
   3) a polycarbonate diol of Formula (I):

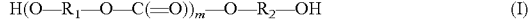

$$H(O-R_1-O-C(=O))_m-O-R_2-OH \qquad (I)$$

wherein each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23; and
   4) a catalyst;
 b) selectively curing the photopolymerizable composition; and
 c) repeating steps a) and b) to form multiple layers and create the orthodontic article.

19. The method of claim 18, wherein the photopolymerizable composition is cured using actinic radiation comprising UV radiation, e-beam radiation, visible radiation, or a combination thereof.

20. The method of claim 18, further comprising subjecting the orthodontic article to a heat treatment.

21. A non-transitory machine readable medium comprising data representing a three-dimensional model of an orthodontic article, when accessed by one or more processors interfacing with a 3D printer, causes the 3D printer to create an orthodontic article comprising a reaction product of a photopolymerizable composition comprising a blend of:
 a) a monofunctional (meth)acrylate monomer whose cured homopolymer has a $T_g$ of 90° C. or greater;
 b) a photoinitiator; and
 c) a polymerization reaction product of components, the components comprising:
  i) an isocyanate;
  ii) a (meth)acrylate mono-ol;
  iii) a polycarbonate diol of Formula (I):

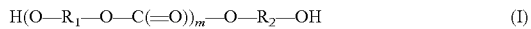

$$H(O-R_1-O-C(=O))_m-O-R_2-OH \qquad (I)$$

wherein each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23; and
  iv) a catalyst.

22. A method comprising:
a) retrieving, from a non-transitory machine readable medium, data representing a 3D model of an article;
b) executing, by one or more processors, a 3D printing application interfacing with a manufacturing device using the data; and
c) generating, by the manufacturing device, a physical object of the orthodontic article, the orthodontic article comprising a reaction product of a photopolymerizable composition, the photopolymerizable composition comprising a blend of:
 i) a monofunctional (meth)acrylate monomer whose cured homopolymer has a $T_g$ of 90° C. or greater;
 ii) a photoinitiator; and
 iii) a polymerization reaction product of components, the components comprising:
  1) an isocyanate;
  2) a (meth)acrylate mono-ol;
  3) a polycarbonate diol of Formula (I):

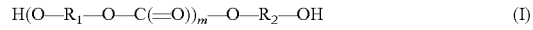

$$H(O-R_1-O-C(=O))_m-O-R_2-OH \qquad (I)$$

wherein each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23; and
  4) a catalyst.

23. A method comprising:
a) receiving, by a manufacturing device having one or more processors, a digital object comprising data specifying a plurality of layers of an orthodontic article; and
b) generating, with the manufacturing device by an additive manufacturing process, the orthodontic article based on the digital object, the orthodontic article comprising a reaction product of a photopolymerizable composition, the photopolymerizable composition comprising a blend of:
 i) a monofunctional (meth)acrylate monomer whose cured homopolymer has a $T_g$ of 90° C. or greater;
 ii) a photoinitiator; and
 iii) a polymerization reaction product of components, the components comprising:
  1) an isocyanate;
  2) a (meth)acrylate mono-ol;
  3) a polycarbonate diol of Formula (I):

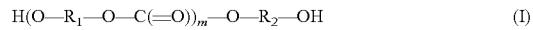

$$H(O-R_1-O-C(=O))_m-O-R_2-OH \qquad (I)$$

wherein each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23; and
  4) a catalyst.

24. A system comprising:
a) a display that displays a 3D model of an orthodontic article; and
b) one or more processors that, in response to the 3D model selected by a user, cause a 3D printer to create a physical object of an orthodontic article, the orthodontic article comprising a reaction product of a photopolymerizable composition, the photopolymerizable composition comprising a blend of:
  i) a monofunctional (meth)acrylate monomer whose cured homopolymer has a $T_g$ of 90° C. or greater;
  ii) a photoinitiator; and
  iii) a polymerization reaction product of components, the components comprising:
    1) an isocyanate;
    2) a (meth)acrylate mono-ol;
    3) a polycarbonate diol of Formula (I):

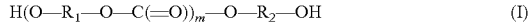

$$H(O-R_1-O-C(=O))_m-O-R_2-OH \quad (I)$$

wherein each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23; and
    4) a catalyst.

25. The orthodontic article of claim 1, wherein the photopolymerizable composition is essentially free of any monofunctional (meth)acrylate monomer having a log P value of less than 3, less than 2, or less than 1.

26. The orthodontic article of claim 1, wherein the diisocyanate comprises an aliphatic isocyanate.

27. The orthodontic article of claim 1, wherein the photopolymerizable composition exhibits a dynamic viscosity of 1 to 10 Pa·s at 40 degrees Celsius.

28. The orthodontic article of claim 1, wherein the polycarbonate diol has a number average molecular weight (Mn) of 450 grams per mole (g/mol) to 3,200 g/mol.

29. The orthodontic article of claim 1, wherein the photopolymerizable composition further comprises a UV absorber in an amount of 0.001 to 5% by weight, based on the total weight of the photopolymerizable composition.

30. The orthodontic article of claim 1, wherein the catalyst is free of tin.

31. The orthodontic article of claim 1, wherein a ratio of the diisocyanate to the polycarbonate diol is 4 molar equivalents of the isocyanate to 2 molar equivalents of the alcohol of the polycarbonate diol.

32. The orthodontic article of claim 1, wherein the photopolymerizable composition further comprises a difunctional monomer in an amount of up to 15 wt. %, based on the total weight of the photopolymerizable composition, and wherein the difunctional monomer comprises a compound of Formula (X) or Formula (XI):

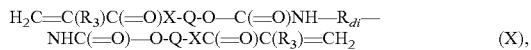

$$H_2C=C(R_3)C(=O)X-Q-O-C(=O)NH-R_{di}-NHC(=O)-O-Q-XC(=O)C(R_3)=CH_2 \quad (X),$$

wherein $R_{di}$ is the residue of a diisocyanate, Q, X, and $R_3$ are as defined for Formula (II);

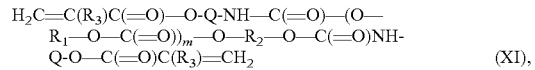

$$H_2C=C(R_3)C(=O)-O-Q-NH-C(=O)-(O-R_1-O-C(=O))_m-O-R_2-O-C(=O)NH-Q-O-C(=O)C(R_3)=CH_2 \quad (XI),$$

wherein Q and $R_3$ are as defined for Formula (II) and $R_1$ and $R_2$ are as defined for Formula (I).

33. The orthodontic article of claim 1, wherein the photopolymerizable composition further comprises a second polymerization reaction product of components, wherein the components comprise:
  1) an isocyanate functional (meth)acrylate compound of Formula (VII):

$$(A)_p\text{-Q-NCO} \quad (VII),$$

wherein A, p, and Q are as defined for Formula (II);
  2) a polycarbonate diol of Formula (I):

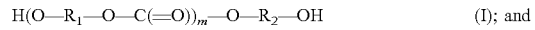

$$H(O-R_1-O-C(=O))_m-O-R_2-OH \quad (I); \text{ and}$$

3) a catalyst,
wherein each of $R_1$ in each $(O-R_1-O-C(=O))$ repeat unit and each $R_2$ are independently an aliphatic, cycloaliphatic, or aliphatic/cycloaliphatic alkylene group and an average number of carbon atoms in a combination of all the $R_1$ and $R_2$ groups is 4 to 10, and m is 2 to 23.

34. The orthodontic article of claim 1, wherein the photopolymerizable composition further comprises a second polymerization reaction product comprising a compound of Formula (VIII):

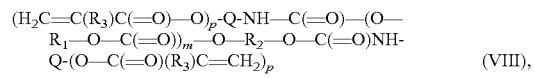

$$(H_2C=C(R_3)C(=O)-O)_p\text{-Q-NH-C}(=O)-(O-R_1-O-C(=O))_m-O-R_2-O-C(=O)NH-Q-(O-C(=O)(R_3)C=CH_2)_p \quad (VIII),$$

wherein Q, p, and $R_3$ are as defined for Formula and $R_1$ and $R_2$ are as defined for Formula (I).

35. The orthodontic article of claim 1, wherein the monofunctional acrylate monomer comprises a cycloaliphatic monofunctional (meth)acrylate.

36. The orthodontic article of claim 1, exhibiting an elongation at break of a printed article of 70% or greater.

37. The orthodontic article of claim 1, comprising 1 wt. % or less extractable components.

38. The method of claim 18, further comprising post curing the article using actinic radiation.

39. The method of claim 18, wherein the method comprises vat polymerization of the photopolymerizable composition.

* * * * *

UNITED STATES PATENT AND TRADEMARK OFFICE
CERTIFICATE OF CORRECTION

PATENT NO. : 11,104,758 B2
APPLICATION NO. : 17/042384
DATED : August 31, 2021
INVENTOR(S) : Thomas Klun et al.

It is certified that error appears in the above-identified patent and that said Letters Patent is hereby corrected as shown below:

In the Claims

Column 80

Line 11, In Claim 2, delete "HO-Q-(A)$_p$" and insert -- HO—Q—(A)$_p$ --, therefor.

Line 20, In Claim 3, delete "(H$_2$C=C(R$_3$)C(=O)—X)$_p$-Q-OC(=O)NH—R$_{di}$—NHC(=O)O-Q-(X—C(=O)(R$_3$)C=CH$_2$)$_p$" and insert -- (H$_2$C=C(R$_3$)C(=O)—X)$_p$—Q—OC(=O)NH—R$_{di}$—NHC(=O)O—Q—(X—C(=O)(R$_3$)C=CH$_2$)$_p$ --, therefor.

Line 33, In Claim 6, after "Formula (IV):", insert

-- 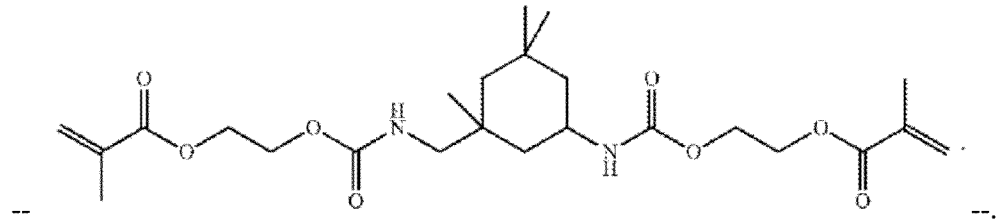 --.

Signed and Sealed this
Fifth Day of April, 2022

Drew Hirshfeld
*Performing the Functions and Duties of the
Under Secretary of Commerce for Intellectual Property and
Director of the United States Patent and Trademark Office*

Line 57, In Claim 10, after "Formula (V):", insert -- 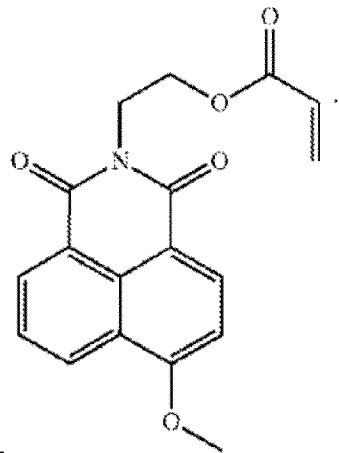 --.

Column 83

Line 48, In Claim 32, delete "H₂C=C(R₃)C(=O)X-Q-O—C(=O)NH—R_di—NHC(=O)—O-Q-XC(=O)C(R₃)=CH₂" and insert -- H₂C=C(R₃)C(=O)X—Q—O—C(=O)NH—R_di—NHC(=O)—O—Q—XC(=O)C(R₃)=CH₂ --, therefor.

Column 84

Line 3, In Claim 32, delete "H₂C=C(R₃)C(=O)—O-Q-NH—C(=O)—(O—R₁—O—C(=O))_m—O—R₂—O—C(=O)NH-Q-O—C(=O)C(R₃)=CH₂" and insert -- H₂C=C(R₃)C(=O)—O—Q—NH—C(=O)—(O—R₁—O—C(=O))_m—O—R₂—O—C(=O)NH—Q—O—C(=O)C(R₃)=CH₂ --, therefor.

Line 15, In Claim 33, delete "(A)_p-Q-NCO" and insert -- (A)_p—Q—NCO --, therefor.

Line 31, In Claim 34, delete "(H₂C=C(R₃)C(=O)—O)_p-Q-NH—C(=O)—(O—R₁—O—C(=O))_m—O—R₂—O—C(=O)NH-Q-(O—C(=O)(R₃)C=CH₂)_p" and insert -- (H₂C=C(R₃)C(=O)—O)_p—Q—NH—C(=O)—(O—R₁—O—C(=O))_m—O—R₂—O—C(=O)NH—Q— (O—C(=O)(R₃)C=CH₂)_p --, therefor.